(12) United States Patent
Sloan et al.

(10) Patent No.: US 9,908,113 B2
(45) Date of Patent: Mar. 6, 2018

(54) METHODS AND DEVICES FOR SAMPLE COLLECTION AND SAMPLE SEPARATION

(71) Applicant: Theranos, Inc., Palo Alto, CA (US)

(72) Inventors: Deborah Sloan, Palo Alto, CA (US); Elizabeth A. Holmes, Palo Alto, CA (US); Pey-Jiun Ko, Palo Alto, CA (US); Edwina Lai, Palo Alto, CA (US)

(73) Assignee: Theranos IP Company, LLC, Newark, CA (US)

( * ) Notice: Subject to any disclaimer, the term of this patent is extended or adjusted under 35 U.S.C. 154(b) by 0 days.

(21) Appl. No.: 14/629,069

(22) Filed: Feb. 23, 2015

(65) Prior Publication Data

US 2015/0231627 A1    Aug. 20, 2015

Related U.S. Application Data

(63) Continuation of application No. PCT/US2014/030070, filed on Mar. 15, 2014.

(60) Provisional application No. 61/786,351, filed on Mar. 15, 2013, provisional application No. 61/799,221, filed on Mar. 15, 2013, provisional application No. 61/948,542, filed on Mar. 5, 2014, provisional application No. 61/952,112, filed on Mar. 12, 2014.

(51) Int. Cl.
*B01L 3/00* (2006.01)

(52) U.S. Cl.
CPC ....... *B01L 3/502* (2013.01); *B01L 2200/0631* (2013.01); *B01L 2300/0681* (2013.01); *B01L 2300/12* (2013.01)

(58) Field of Classification Search
CPC .... G01N 33/525; G01N 33/521; B01L 3/502; B01L 2233/0631; B01L 2300/0681
See application file for complete search history.

(56) References Cited

U.S. PATENT DOCUMENTS

| | | |
|---|---|---|
| 3,405,706 A | 10/1968 | Paul |
| 3,848,581 A | 11/1974 | Cinqualbre et al. |
| 3,960,139 A | 6/1976 | Bailey |
| 4,150,089 A | 4/1979 | Linet |
| 4,210,156 A | 7/1980 | Bennett |
| 4,271,119 A | 6/1981 | Columbus |
| 4,292,817 A | 10/1981 | Loucks |

(Continued)

FOREIGN PATENT DOCUMENTS

| | | |
|---|---|---|
| CN | 101533005 A | 9/2009 |
| CN | 202376524 U | 8/2012 |

(Continued)

OTHER PUBLICATIONS

International Report and Written Opinion dated Nov. 20, 2014 for PCT/US2014/030070.

(Continued)

*Primary Examiner* — Brian R. Gordon

(57) ABSTRACT

Methods and devices are provided for sample collection and sample separation. In one embodiment, a device is provided for use with a formed component liquid sample, the device comprising at least one sample inlet for receiving said sample; at least a first outlet for outputting only a liquid portion of the formed component liquid sample; at least a second outlet for outputting the formed component liquid sample at least a first material mixed therein.

16 Claims, 44 Drawing Sheets

(56) References Cited

U.S. PATENT DOCUMENTS

| | | | |
|---|---|---|---|
| 4,434,802 A | 3/1984 | Rilliet | |
| 4,474,033 A | 10/1984 | Baker | |
| 4,492,634 A | 1/1985 | Villa-Real | |
| 4,650,662 A | 3/1987 | Goldfinger et al. | |
| 4,676,256 A | 6/1987 | Golden | |
| 4,703,762 A | 11/1987 | Rathbone et al. | |
| 4,949,722 A | 8/1990 | Bean et al. | |
| 4,951,685 A | 8/1990 | Blair | |
| 4,976,271 A | 12/1990 | Blair | |
| 4,980,297 A | 12/1990 | Haynes et al. | |
| 5,000,854 A | 3/1991 | Yang | |
| 5,033,476 A | 7/1991 | Kasai | |
| 5,086,780 A | 2/1992 | Schmitt | |
| 5,100,626 A * | 3/1992 | Levin | G01N 33/54366 422/420 |
| 5,104,375 A | 4/1992 | Wolf et al. | |
| 5,139,031 A | 8/1992 | Guirguis | |
| 5,145,565 A | 9/1992 | Kater et al. | |
| 5,222,502 A | 6/1993 | Kurose | |
| 5,249,584 A | 10/1993 | Karkar et al. | |
| 5,277,198 A | 1/1994 | Kanner et al. | |
| 5,314,412 A | 5/1994 | Rex | |
| 5,360,423 A | 11/1994 | McCormick | |
| 5,364,533 A | 11/1994 | Ogura et al. | |
| 5,447,417 A | 9/1995 | Kuhl et al. | |
| 5,505,721 A | 4/1996 | Leach et al. | |
| 5,569,210 A | 10/1996 | Moen | |
| 5,707,876 A | 1/1998 | Levine | |
| 5,785,662 A | 7/1998 | Alexander | |
| 5,833,630 A | 11/1998 | Kloth | |
| 5,897,508 A | 4/1999 | Konrad | |
| 5,922,210 A | 7/1999 | Brody et al. | |
| 6,008,059 A | 12/1999 | Schrier et al. | |
| 6,056,925 A | 5/2000 | Sarstedt | |
| 6,221,672 B1 | 4/2001 | Baugh et al. | |
| 6,391,265 B1 | 5/2002 | Buechler et al. | |
| 6,521,460 B1 | 2/2003 | Strasser et al. | |
| 6,531,098 B1 | 3/2003 | Kenney | |
| 6,541,243 B1 | 4/2003 | Harris et al. | |
| 6,555,064 B2 | 4/2003 | Baugh et al. | |
| 6,555,066 B2 | 4/2003 | Baugh et al. | |
| 6,555,381 B2 | 4/2003 | Baugh et al. | |
| 6,626,863 B1 | 9/2003 | Berler | |
| 6,852,290 B2 | 2/2005 | Hager et al. | |
| 6,899,227 B2 | 5/2005 | Mierisch | |
| 7,118,538 B2 | 10/2006 | Konrad | |
| 7,279,134 B2 * | 10/2007 | Chan | B01D 61/022 216/2 |
| 7,305,896 B2 | 12/2007 | Howell et al. | |
| 7,335,188 B2 | 2/2008 | Graf | |
| 7,378,054 B2 | 5/2008 | Karmali | |
| 7,413,910 B2 | 8/2008 | Kearney et al. | |
| 7,699,966 B2 | 4/2010 | Qin et al. | |
| 7,785,773 B1 | 8/2010 | Anderson et al. | |
| 7,810,348 B2 | 10/2010 | Shewchuk | |
| 8,158,062 B2 | 4/2012 | Dykes et al. | |
| 8,273,312 B2 * | 9/2012 | Porat | B01L 3/502 210/455 |
| 8,801,918 B2 | 8/2014 | Qin et al. | |
| 8,841,118 B2 | 9/2014 | Robinson et al. | |
| 2001/0031932 A1 | 10/2001 | Blake et al. | |
| 2002/0004647 A1 | 1/2002 | Leong | |
| 2003/0159999 A1 | 8/2003 | Oakey et al. | |
| 2003/0166291 A1 * | 9/2003 | Jones | G01N 33/5302 436/71 |
| 2003/0185707 A1 | 10/2003 | Iwaki et al. | |
| 2003/0206828 A1 | 11/2003 | Bell | |
| 2004/0051154 A1 | 3/2004 | Yamakawa et al. | |
| 2004/0053422 A1 * | 3/2004 | Chan | B01D 61/022 436/180 |
| 2004/0089057 A1 | 5/2004 | Hobbs et al. | |
| 2004/0129678 A1 | 7/2004 | Crowley et al. | |
| 2004/0191124 A1 * | 9/2004 | Noetzel | B01L 3/502746 422/69 |
| 2004/0245102 A1 | 12/2004 | Gilbert et al. | |
| 2005/0036907 A1 | 2/2005 | Shoji | |
| 2005/0059163 A1 | 3/2005 | Dastane et al. | |
| 2005/0106066 A1 * | 5/2005 | Saltsman | B01F 5/0473 422/504 |
| 2005/0139547 A1 | 6/2005 | Manoussakis et al. | |
| 2005/0243304 A1 | 11/2005 | Padmanabhan et al. | |
| 2006/0228258 A1 | 10/2006 | Samsoondar | |
| 2006/0228259 A1 * | 10/2006 | Samsoondar | B01L 3/502715 422/82.05 |
| 2006/0254962 A1 * | 11/2006 | Samsoondar | A61B 5/14546 210/85 |
| 2007/0104616 A1 | 5/2007 | Keenan et al. | |
| 2007/0154895 A1 | 7/2007 | Spaid et al. | |
| 2007/0227967 A1 | 10/2007 | Sakaino et al. | |
| 2007/0269893 A1 | 11/2007 | Blankenstein et al. | |
| 2008/0076190 A1 | 3/2008 | Carlisle et al. | |
| 2008/0312555 A1 | 12/2008 | Boecker | |
| 2009/0088336 A1 | 4/2009 | Burd et al. | |
| 2009/0107909 A1 | 4/2009 | Kotera et al. | |
| 2009/0120865 A1 | 5/2009 | Chung et al. | |
| 2009/0136982 A1 | 5/2009 | Tang et al. | |
| 2009/0139925 A1 | 6/2009 | Sternberg | |
| 2009/0162941 A1 | 6/2009 | Winkler et al. | |
| 2009/0181411 A1 * | 7/2009 | Battrell | B01F 11/0071 435/7.92 |
| 2009/0208923 A1 | 8/2009 | Gelfand et al. | |
| 2009/0226957 A1 | 9/2009 | Paterlini-Brechot | |
| 2009/0240165 A1 | 9/2009 | Yoneya et al. | |
| 2009/0259145 A1 | 10/2009 | Bartfeld et al. | |
| 2009/0306543 A1 | 12/2009 | Slowey et al. | |
| 2010/0184056 A1 | 7/2010 | Weinberger et al. | |
| 2010/0185322 A1 | 7/2010 | Bylsma et al. | |
| 2010/0224551 A1 | 9/2010 | Hongo et al. | |
| 2010/0249652 A1 | 9/2010 | Rush et al. | |
| 2010/0261223 A1 | 10/2010 | Margraf et al. | |
| 2010/0284861 A1 * | 11/2010 | Horiike | G01N 30/96 422/70 |
| 2011/0011781 A1 | 1/2011 | Blankenstein et al. | |
| 2011/0124025 A1 | 5/2011 | Castracane et al. | |
| 2011/0284110 A1 | 11/2011 | Gagnon | |
| 2011/0312481 A1 | 12/2011 | Nguyen et al. | |
| 2012/0029384 A1 | 2/2012 | Crosman | |
| 2012/0085648 A1 | 4/2012 | Kartalov et al. | |
| 2012/0101407 A1 | 4/2012 | Chan | |
| 2012/0177537 A1 | 7/2012 | Aota et al. | |
| 2012/0220047 A1 * | 8/2012 | Seifried | B01L 3/502753 436/178 |
| 2012/0256027 A1 | 10/2012 | Yang et al. | |
| 2012/0258459 A1 | 10/2012 | Huang | |
| 2012/0277629 A1 | 11/2012 | Bernstein et al. | |
| 2012/0305500 A1 | 12/2012 | Bormann et al. | |
| 2013/0068310 A1 | 3/2013 | Sip et al. | |
| 2013/0079248 A1 | 3/2013 | Kim et al. | |
| 2013/0172780 A1 | 7/2013 | Kuenstner | |
| 2013/0175213 A1 | 7/2013 | Dorrer et al. | |
| 2013/0264205 A1 | 10/2013 | Hwang et al. | |
| 2013/0264266 A1 | 10/2013 | Shick et al. | |
| 2013/0264295 A1 | 10/2013 | Lee et al. | |
| 2014/0004501 A1 | 1/2014 | Talebpour et al. | |
| 2014/0073990 A1 | 3/2014 | Holmes et al. | |
| 2014/0323911 A1 | 3/2014 | Sloan | |
| 2014/0134595 A1 | 5/2014 | Kurowski et al. | |
| 2014/0138260 A1 * | 5/2014 | Briman | G01N 27/48 205/775 |
| 2014/0171829 A1 | 6/2014 | Holmes et al. | |
| 2014/0219886 A1 | 8/2014 | Choi et al. | |
| 2014/0316300 A1 | 10/2014 | Holmes et al. | |
| 2014/0323913 A1 | 10/2014 | Holmes et al. | |
| 2014/0339161 A1 | 11/2014 | Leonard et al. | |
| 2014/0342371 A1 | 11/2014 | Holmes | |
| 2014/0356884 A1 | 12/2014 | Mittal et al. | |
| 2014/0358036 A1 | 12/2014 | Holmes | |

(56) References Cited

U.S. PATENT DOCUMENTS

| | | |
|---|---|---|
| 2015/0060353 A1 | 3/2015 | Neijzen et al. |
| 2015/0192504 A1 | 7/2015 | Cho et al. |

FOREIGN PATENT DOCUMENTS

| | | |
|---|---|---|
| EA | 200600893 A1 | 12/2006 |
| EP | 0203930 B1 | 7/1990 |
| EP | 0550950 A2 | 7/1993 |
| EP | 2052807 A1 | 4/2009 |
| GB | 2409411 | 6/2005 |
| JP | 2004184099 A | 7/2004 |
| JP | 2008039615 A | 2/2008 |
| SU | 1088789 A | 4/1984 |
| WO | 1986003008 A1 | 5/1986 |
| WO | 2005076733 A2 | 8/2005 |
| WO | 2005088300 A1 | 9/2005 |
| WO | 2009053432 A | 4/2009 |
| WO | 2011079217 A1 | 6/2011 |
| WO | 2014039909 A | 3/2014 |
| WO | 2014088606 A | 6/2014 |
| WO | 2014145330 A2 | 9/2014 |
| WO | 2014145935 A1 | 9/2014 |
| WO | 2015134809 A1 | 9/2015 |

OTHER PUBLICATIONS

International Search Report and Written Opinion dated Aug. 28, 2014 for Application No. PCT/US2014/030792.
Office Action dated Nov. 28, 2014 for U.S. Appl. No. 14/320,471.
Office Action dated Mar. 20, 2015 for U.S. Appl. No. 14/320,471.
Office Action dated Jun. 16, 2015 for U.S. Appl. No. 14/020,435.
The International Search Report and the Written Opinion dated Feb. 13, 2014 for Application No. PCT/US2013/058627.
U.S. Appl. No. 61/697,797, filed Sep. 6, 2012.
U.S. Appl. No. 61/786,351, filed Mar. 15, 2013.
U.S. Appl. No. 61/852,489, filed Mar. 15, 2013.
U.S. Appl. No. 61/952,125, filed Mar. 12, 2014.
U.S. Appl. No. 61/952,130, filed Mar. 12, 2014.
BD Diagnostics. product catalogue 2010/2011.
Biosigma. Disposable Labware for Life Science. catalogue 2009.
Centers for Disease Control and Prevention. "Capillary Blood Sampling Protocol" 1997.
Deschka. "Blood Collection in Practice. A guideline for phlebotomists", Sep. 2009.
Home Blood Tests UK. "Home blood test kits. Collect at home, send to our laboratory." dated Jun. 13, 2012.
Massachusetts Department of Public Health. "Instructions for fingerstick sample collection for lead testing", Sep. 2012.
Medichecks. "Collection of a finger prick blood sample", Sep. 2012.
Office Action dated Jan. 11, 2016 for U.S. Appl. No. 14/447,099.
Office Action dated Oct. 14, 2014 for U.S. Appl. No. 14/447,099.
Office Action dated Nov. 4, 2015 for U.S. Appl. No. 14/020,435.
Office Action dated Mar. 25, 2015 for U.S. Appl. No. 14/447,099.
Office Action dated Apr. 6, 2015 for U.S. Appl. No. 14/446,080.
Office Action dated Jul. 30, 2015 for U.S. Appl. No. 14/446,080.
Office Action dated Aug. 5, 2015 for U.S. Appl. No. 14/098,177.
RAM Scientific. Safe-T-Fill Capillary Blood Collection Tubes. 2006.
Sarstedt. comprehensive catalogue. Cover page and pp. 1-43. last modified 2007.
Sarstedt. comprehensive catalogue. last modified 2007.
The International Search Report and the Written Opinion dated Jun. 10, 2014 for Application No. PCT/US13/00268.
U.S. Appl. No. 61/733,886, filed Dec. 5, 2012.
U.S. Appl. No. 61/798,873, filed Mar. 15, 2013.
U.S. Appl. No. 61/875,030, filed Sep. 7, 2013.
U.S. Appl. No. 61/948,542, filed Mar. 5, 2014.
U.S. Appl. No. 61/952,112, filed Mar. 12, 2014.
U.S. Appl. No. 62/011,023, filed Jun. 11, 2014.
Office Action dated Mar. 22, 2016 for U.S. Appl. No. 14/020,435.
Notice of Allowance dated Jun. 13, 2016 for U.S. Appl. No. 14/320,471.
Office Action dated May 5, 2016 for U.S. Appl. No. 14/214,774.
Office Action dated Jul. 22, 2016 for U.S. Appl. No. 14/214,771.
Office Action dated Sep. 22, 2016 for U.S. Appl. No. 14/020,435.
International Search Report dated Dec. 22, 2016 for PCT/US2016/051158.
Notice of Allowance dated Feb. 17, 2017 for U.S. Appl. No. 14/020,435.
Office Action dated Mar. 23, 2017 for U.S. Appl. No. 14/639,986.
Office Action dated May 5, 2017 for U.S. Appl. No. 14/214,771.
Notice of Allowance dated Aug. 10, 2015 for U.S. Appl. No. 14/320,471.
Notice of Allowance dated Jan. 27, 2017 for U.S. Appl. No. 13/214,774.
Office Action dated Dec. 29, 2016 for U.S. Appl. No. 14/446,080.
Office Action dated Jan. 12, 2018 for U.S. Appl. No. 14/639,986.

* cited by examiner

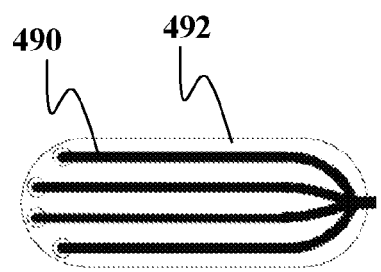
FIG. 47A  FIG. 47B
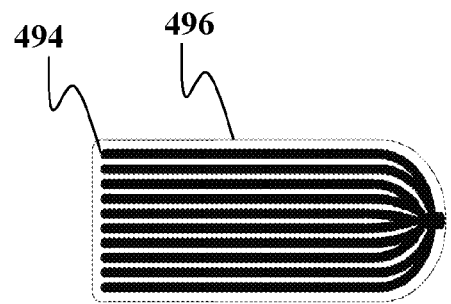
FIG. 48A  FIG. 48B

METHODS AND DEVICES FOR SAMPLE COLLECTION AND SAMPLE SEPARATION

BACKGROUND

A blood sample for use in laboratory testing is often obtained by way of venipuncture, which typically involves inserting a hypodermic needle into a vein on the subject. Blood extracted by the hypodermic needle may be drawn directly into a syringe or into one or more sealed vials for subsequent processing. When a venipuncture may be difficult or impractical such as on a newborn infant, a non-venous puncture such as a heel stick or other alternate site puncture may be used to extract a blood sample for testing. After the blood sample is collected, the extracted sample is typically packaged and transferred to a processing center for analysis.

Unfortunately, conventional sample collection and testing techniques of bodily fluid samples have drawbacks. For instance, except for the most basic tests, blood tests that are currently available typically require a substantially high volume of blood to be extracted from the subject. Because of the high volume of blood, extraction of blood from alternate sample sites on a subject, which may be less painful and/or less invasive, are often disfavored as they do not yield the blood volumes needed for conventional testing methodologies. In some cases, patient apprehension associated with venipuncture may reduce patient compliance with testing protocol. Furthermore, the traditional collection technique adds unnecessary complexity when trying to separate a single blood sample into different containers for different pre-analytical processing.

SUMMARY

At least some of the disadvantages associated with the prior art are overcome by one or more embodiments of the devices, systems, or methods described herein.

In one embodiment, a device is provided for use with a formed component liquid sample, the device comprising at least one sample inlet for receiving said sample; at least a first outlet for outputting only a liquid portion of the formed component liquid sample; at least a second outlet for outputting the formed component liquid sample at least a first material mixed therein.

It should be understood that one or more of the following features may be adapted for use with any of the embodiments described herein. By way of non-limiting example, the body may a first pathway fluidically couples the sample inlet with the first outlet. Optionally, a second pathway fluidically couples the sample inlet with the second outlet. Optionally, a separation material along the first pathway configured to remove said formed component from the sample prior to outputting at the first outlet. Optionally, the separation material and a distributor are configured to have an interface that provides a multi-mode sample propagation pattern wherein at least a first portion is propagating laterally within the separator and a second portion is propagating through the channels of the distributor over the separator. Optionally, there is at least 50 mm$^2$ surface area of separator per 30 uL of sample to filter. Optionally, there is at least 60 mm$^2$ surface area of separator per 30 uL of sample to filter. Optionally, there is at least 70 mm$^2$ surface area of separator per 30 uL of sample to filter. Optionally, the inlet directs the sample to primarily contact a planar portion of separator surface, and not a lateral edge of the separator. Optionally, the amount of time for sample to fill the first pathway and reach the first outlet is substantially equal to the time for sample to fill the second pathway and reach the second outlet. Optionally, the first pathway comprises a portion configured in a distributed pattern of channels over the filtration material to preferentially direct the sample over the surface of the separation material in a pre-determined configuration. Optionally, at least a portion of the separation material is coupled to a vent which contacts the membrane in a manner that the vent is only accessible fluidically by passing through the separation material. Optionally, containers have interiors under vacuum pressure that draw sample therein. Optionally, the separation material is held in the device under compression. Optionally, the separation material comprises an asymmetric porous membrane. Optionally, the separation material is a mesh. Optionally, the separation material comprises polyethylene (coated by ethylene vinyl alcohol copolymer). Optionally, at least a portion of the separation material comprises a polyethersulfone. Optionally, at least a portion of the separation material comprises an asymmetric polyethersulfone. Optionally, at least a portion of the separation material comprises polyarylethersulfone. Optionally, at least a portion of the separation material comprises an asymmetric polyarylethersulfone. Optionally, at least a portion of the separation material comprises a polysulfone. Optionally, the separation material comprises an asymmetric polysulfone. Optionally, the separation material comprises a cellulose or cellulose derivative material. Optionally, the separation material comprises polypropylene (PP). Optionally, the separation material comprises polymethylmethacrylate (PMMA). In one non-limiting example, the separation material comprises a polymer membrane wherein filtrate exit surface of the membrane comprises a relatively open pore structure and the opposite surface comprises a more open pore structure and wherein the supporting structure comprises asymmetry through at least 50% of the supporting structure but no more than 95% of the supporting structure, the membrane having surface pores at the minimum surface of a mean diameter of at least about 1 micron and having a flow rate of greater than about 4 cm/min/psi. Optionally, the flow rate of the material, unassisted, is between 1 cm/min/psi and 4.3 2 cm/min/psi.

In one embodiment described herein, a device for collecting a bodily fluid sample from a subject is provided comprising: at least two sample collection pathways configured to draw the bodily fluid sample into the device from a single end of the device in contact with the subject, thereby separating the fluid sample into two separate samples; a second portion comprising a plurality of sample containers for receiving the bodily fluid sample collected in the sample collection pathways, the sample containers operably engagable to be in fluid communication with the sample collection pathways, whereupon when fluid communication is established, the containers provide a motive force to move a majority of the two separate samples from the pathways into the containers. Optionally, the device includes a separation material along one of the sample collection pathways, the material configured to remove formed components from the sample when outputting to at least one of the sample containers.

In another embodiment described herein, a device for collecting a bodily fluid sample is provided comprising: a first portion comprising at least one fluid collection location leading to at least two sample collection pathways configured to draw the fluid sample therein via a first type of motive force; a second portion comprising a plurality of sample containers for receiving the bodily fluid sample collected in the sample collection pathways, the sample containers operably engagable to be in fluid communication with the sample collection pathways, whereupon when fluid communication is established, the containers provide a second motive force different from the first motive force to move a majority of the bodily fluid sample from the pathways into the containers; wherein at least one of the sample collection pathways comprises a fill indicator to indicate when a minimum fill level has been reached and that at least one of the sample containers can be engaged to be in fluid communication with at least one of the sample collection pathways. Optionally, the device includes a separation material along one of the sample collection pathways, the material configured to remove formed components from the sample when outputting to at least one of the sample containers.

In another embodiment described herein, a device for collecting a bodily fluid sample is provided comprising a first portion comprising at least two sample collection channels configured to draw the fluid sample into the sample collection channels via a first type of motive force, wherein one of the sample collection channels has an interior coating designed to mix with the fluid sample and another of the sample collection channels has another interior coating chemically different from said interior coating; a second portion comprising a plurality of sample containers for receiving the bodily fluid sample collected in the sample collection channels, the sample containers operably engagable to be in fluid communication with the collection channels, whereupon when fluid communication is established, the containers provide a second motive force different from the first motive force to move a majority of the bodily fluid sample from the channels into the containers; wherein containers are arranged such that mixing of the fluid sample between the containers does not occur. Optionally, the device includes a separator along one of the sample collection channels, the separator configured to remove formed component from the sample when outputting to at least one of the sample containers.

In another embodiment described herein, a device for collecting a bodily fluid sample is provided comprising: a first portion comprising a plurality of sample collection channels, wherein at least two of the channels are configured to simultaneously draw the fluid sample into each of the at least two sample collection channels via a first type of motive force; a second portion comprising a plurality of sample containers for receiving the bodily fluid sample collected in the sample collection channels, wherein the sample containers have a first condition where the sample containers are not in fluid communication with the sample collection channels, and a second condition where the sample containers are operably engagable to be in fluid communication with the collection channels, whereupon when fluid communication is established, the containers provide a second motive force different from the first motive force to move bodily fluid sample from the channels into the containers. Optionally, the device includes a separator along one of the sample collection channels, the separator configured to remove formed component from the sample when outputting to at least one of the sample containers.

In another embodiment described herein, a sample collection device is provided comprising: (a) a collection channel comprising a first opening and a second opening, and being configured to draw a bodily fluid sample via capillary action from the first opening towards the second opening; and (b) a sample container for receiving the bodily fluid sample, the container being engagable with the collection channel, having an interior with a vacuum therein, and having a cap configured to receive a channel; wherein the second opening is defined by a portion the collection channel configured to penetrate the cap of the sample container, and to provide a fluid flow path between the collection channel and the sample container, and the sample container has an interior volume no greater than ten times larger than the interior volume of the collection channel. Optionally, the device comprises a separator along one of the sample collection channel, the separator configured to remove formed component from the sample prior to and when outputting to the sample container.

In another embodiment described herein, a sample collection device is provided comprising: (a) a collection channel comprising a first opening and a second opening, and being configured to draw a bodily fluid sample via capillary action from the first opening towards the second opening; (b) a sample container for receiving the bodily fluid sample, the container being engagable with the collection channel, having an interior with a vacuum therein, and having a cap configured to receive a channel; and (c) an adaptor channel configured to provide a fluid flow path between the collection channel and the sample container, having a first opening and a second opening, the first opening being configured to contact the second opening of the collection channel, the second opening being configured to penetrate the cap of the sample container. Optionally, the device comprises a separator along one of the sample collection channel, the separator configured to remove formed component from the sample prior to and when outputting to the sample container.

In another embodiment described herein, a sample collection device is provided comprising: (a) a body, containing a collection channel, the collection channel comprising a first opening and a second opening, and being configured to draw a bodily fluid via capillary action from the first opening towards the second opening; (b) a base, containing a sample container for receiving the bodily fluid sample, the sample container being engagable with the collection channel, having an interior with a vacuum therein, and having a cap configured to receive a channel; and (c) a support, wherein, the body and the base are connected to opposite ends of the support, and are configured to be movable relative to each other, such that sample collection device is configured to have an extended state and a compressed state, wherein at least a portion of the base is closer to the body in the extended state of the device than in the compressed state, the second opening of the collection channel is configured to penetrate the cap of the sample container, in the extended state of the device, the second opening of the collection channel is not in contact with the interior of the sample container, and in the compressed state of the device, the second opening of the collection channel extends into the interior of the sample container through the cap of the container, thereby providing fluidic communication between the collection channel and the sample container. Optionally, the device comprises a separator along one of the sample collection channel, the separator configured to remove formed component from the sample prior to and when outputting to the sample container.

In another embodiment described herein, a sample collection device is provided comprising: (a) a body, containing a collection channel, the collection channel comprising a first opening and a second opening, and being configured to draw a bodily fluid via capillary action from the first opening towards the second opening; (b) a base, containing a sample container for receiving the bodily fluid sample, the sample container being engagable with the collection channel, having an interior with a vacuum therein and having a cap configured to receive a channel; (c) a support, and (d) an adaptor channel, having a first opening and a second opening, the first opening being configured to contact the second opening of the collection channel, and the second opening being configured to penetrate the cap of the sample container, wherein, the body and the base are connected to opposite ends of the support, and are configured to be movable relative to each other, such that sample collection device is configured to have an extended state and a compressed state, wherein at least a portion of the base is closer to the body in the extended state of the device than in the compressed state, in the extended state of the device, the adaptor channel is not in contact with one or both of the collection channel and the interior of the sample container, and in the compressed state of the device, the first opening of the adaptor channel is in contact with the second opening of the collection channel, and the second opening of the adaptor channel extends into the interior of the sample container through the cap of the container, thereby providing fluidic communication between the collection channel and the sample container. Optionally, the device comprises a separator along one of the sample collection channel, the separator configured to remove formed component from the sample prior to and when outputting to the sample container.

In another embodiment described herein, a device for collecting a fluid sample from a subject is provided comprising: (a) a body containing a collection channel, the collection channel comprising a first opening and a second opening, and being configured to draw a bodily fluid via capillary action from the first opening towards the second opening; (b) a base, engagable with the body, wherein the base supports a sample container, the container being engagable with the collection channel, having an interior with a vacuum therein, and having a cap configured to receive a channel; wherein the second opening of the collection channel is configured to penetrate the cap of the sample container, and to provide a fluid flow path between the collection channel and the sample container. Optionally, the device comprises a separator along one of the sample collection channel, the separator configured to remove formed component from the sample prior to and when outputting to the sample container.

In another embodiment described herein, a device for collecting a fluid sample from a subject is provided comprising: (a) a body containing a collection channel, the collection channel comprising a first opening and a second opening, and being configured to draw a bodily fluid via capillary action from the first opening towards the second opening; (b) a base, engagable with the body, wherein the base supports a sample container, the sample container being engagable with the collection channel, having an interior with a vacuum therein and having a cap configured to receive a channel; and (c) an adaptor channel, having a first opening and a second opening, the first opening being configured to contact the second opening of the collection channel, and the second opening being configured to penetrate the cap of the sample container. Optionally, the device comprises a separator along one of the sample collection channel, the separator configured to remove formed component from the sample prior to and when outputting to the sample container.

It should be understood that one or more of the following features may be adapted for use with any of the embodiments described herein. By way of non-limiting example, the body may comprise of two collection channels. Optionally, the interior of the collection channel(s) are coated with an anticoagulant. Optionally, the body comprises a first collection channel and a second collection channel, and the interior of the first collection channel is coated with a different anticoagulant than the interior of the second collection channel. Optionally, the first anticoagulant is ethylenediaminetetraacetic acid (EDTA) and the second anticoagulant is different from EDTA. Optionally, the first anticoagulant is citrate and the second anticoagulant is different from citrate. Optionally, the first anticoagulant is heparin and the second anticoagulant is different from heparin. Optionally, one anticoagulant is heparin and the second anticoagulant is EDTA. Optionally, one anticoagulant is heparin and the second anticoagulant is citrate. Optionally, one anticoagulant is citrate and the second anticoagulant is EDTA. Optionally, the body is formed from an optically transmissive material. Optionally, the device includes the same number of sample containers as collection channels. Optionally, the device includes the same number of adaptor channels as collection channels. Optionally, the base contains an optical indicator that provides a visual indication of whether the sample has reached the sample container in the base. Optionally, the base is a window that allows a user to see the container in the base. Optionally, the support comprises a spring, and spring exerts a force so that the device is at the extended state when the device is at its natural state. Optionally, the second opening of the collection channel or the adaptor channel is capped by a sleeve, wherein said sleeve does not prevent movement of bodily fluid via capillary action from the first opening towards the second opening. Optionally, the sleeve contains a vent. Optionally, each collection channel can hold a volume of no greater than 500 uL. Optionally, each collection channel can hold a volume of no greater than 200 uL. Optionally, each collection channel can hold a volume of no greater than 100 uL. Optionally, each collection channel can hold a volume of no greater than 70 uL. Optionally, each collection channel can hold a volume of no greater than 500 uL. Optionally, each collection channel can hold a volume of no greater than 30 uL. Optionally, the internal circumferential perimeter of a cross-section of each collection channel is no greater than 16 mm. Optionally, the internal circumferential perimeter of a cross-section of each collection channel is no greater than 8 mm. Optionally, the internal circumferential perimeter of a cross-section of each collection channel is no greater than 4 mm. Optionally, the internal circumferential perimeter is a circumference. Optionally, the device comprises a first and a second collection channel, and the opening of the first channel is adjacent to an opening of said second channel, and the openings are configured to draw blood simultaneously from a single drop of blood. Optionally, the opening of the first channel and the opening of the second channel have a center-to-center spacing of less than or equal to about 5 mm. Optionally, each sample container has an interior volume no greater than twenty times larger than the interior volume of the collection channel with which it is engagable. Optionally, each sample container has an interior volume no greater than ten times larger than the interior volume of the collection channel with which it is engagable. Optionally, each sample container has an interior volume no greater than five times larger than the interior volume of the collection channel with which it is engagable. Optionally, each sample container has an interior volume no greater than two times larger than the interior volume of the collection channel with which it is engagable. Optionally, establishment of fluidic communication between the collection channel and the sample container results in transfer of at least 90% of the bodily fluid sample in the collection channel into the sample container.

It should be understood that one or more of the following features may be adapted for use with any of the embodiments described herein. Optionally, establishment of fluidic communication between the collection channel and the sample container results in transfer of at least 95% of the bodily fluid sample in the collection channel into the sample container. Optionally, establishment of fluidic communication between of the collection channel and the sample container results in transfer of at least 98% of the bodily fluid sample in the collection channel into the sample container. Optionally, establishment of fluidic communication between the collection channel and the sample container results in transfer of the bodily fluid sample into the sample container and in no more than ten uL of bodily fluid sample remaining in the collection channel. Optionally, establishment of fluidic communication between the collection channel and the sample container results in transfer of the bodily fluid sample into the sample container and in no more than five uL of bodily fluid sample remaining in the collection channel. Optionally, engagement of the collection channel with the sample container results in transfer of the bodily fluid sample into the sample container and in no more than 2 uL of bodily fluid sample remaining in the collection channel.

In another embodiment described herein, a method is provided comprising contacting one end of a sample collection device to a bodily fluid sample to split the sample into at least two portions by drawing the sample into at least two collection channels of the sample collection device by way of a first type of motive force; establishing fluid communication between the sample collection channels and the sample containers after a desired amount of sample fluid has been confirmed to be in at least one of the collection channels, whereupon the containers provide a second motive force different from the first motive force to move each of the portions of bodily fluid sample into their respective containers.

In another embodiment described herein, a method is provided comprising metering a minimum amount of sample into at least two channels by using a sample collection device with at least two of the sample collection channels configured to simultaneously draw the fluid sample into each of the at least two sample collection channels via a first type of motive force; after a desired amount of sample fluid has been confirmed to be in the collection channels, fluid communication is established between the sample collection channels and the sample containers, whereupon the containers provide a second motive force different from the first motive force use to collect the samples to move bodily fluid sample from the channels into the containers.

In another embodiment described herein, a method of collecting a bodily fluid sample is provided comprising (a) contacting a bodily fluid sample with a device comprising a collection channel, the collection channel comprising a first opening and a second opening, and being configured to draw a bodily fluid via capillary action from the first opening towards the second opening, such that the bodily fluid sample fills the collection channel from the first opening through the second opening; (b) establishing a fluid flow path between the collection channel and the interior of a sample container, said sample container having an interior volume no greater than ten times larger than the interior volume of the collection channel and having a vacuum prior to establishment of the fluid flow path between the collection channel and the interior of the sample container, such that establishment of the fluid flow path between the collection channel and the interior of the sample container generates a negative pressure at the second opening of the collection channel, and the fluidic sample is transferred from the collection channel to the interior of the sample container.

In another embodiment described herein, a method of collecting a bodily fluid sample is provided comprising (a) contacting a bodily fluid sample with any collection device as described herein, such that the bodily fluid sample fills the collection channel from the first opening through the second opening of at least one of the collection channel(s) in the device; and (b) establishing a fluid flow path between the collection channel and the interior of the sample container, such that establishing a fluid flow path between the collection channel and the interior of the sample container generates a negative pressure at the second opening of the collection channel, and the fluidic sample is transferred from the collection channel to the interior of the sample container.

It should be understood that one or more of the following features may be adapted for use with any of the embodiments described herein. Optionally, the collection channel and the interior of the sample container are not brought into fluid communication until the bodily fluid reaches the second opening of the collection channel. Optionally, the device comprises two collection channels, and the collection channels and the interior of the sample containers are not brought into fluidic communication until the bodily fluid reaches the second opening of both collection channels. Optionally, the second opening of the collection channel in the device is configured to penetrate the cap of the sample container, and wherein a fluidic flow path between the second opening of the collection channel and the sample container is established by providing relative movement between the second opening of the collection channel and the sample container, such that the second opening of the collection channel penetrates the cap of the sample container. Optionally, the device comprises an adaptor channel for each collection channel in the device, the adaptor channel having a first opening and a second opening, the first opening being configured to contact the second opening of the collection channel, and the second opening being configured to penetrate the cap of the sample container, and wherein a fluidic flow path between the collection channel and the sample container is established by providing relative movement between two or more of: (a) the second opening of the collection channel, (b) the adaptor channel, and (c) the sample container, such that the second opening of the adaptor channel penetrates the cap of the sample container.

In another embodiment described herein, a method for collecting a bodily fluid sample from a subject is provided comprising: (a) bringing a device comprising a first channel and a second channel into fluidic communication with a bodily fluid from the subject, each channel having an input opening configured for fluidic communication with said bodily fluid, each channel having an output opening downstream of the input opening of each channel, and each channel being configured to draw a bodily fluid via capillary action from the input opening towards the output opening; (b) bringing, through the output opening of each of the first channel and the second channel, said first channel and said second channel into fluidic communication with a first container and a second container, respectively; and (c) directing said bodily fluid within each of said first channel and second channel to each of said first container and second container with the aid of: (i) negative pressure relative to ambient pressure in said first container or said second container, wherein said negative pressure is sufficient to effect flow of said bodily fluid through said first channel or said second channel into its corresponding container, or (ii) positive pressure relative to ambient pressure upstream of said first channel or said second channel, wherein said positive pressure is sufficient to effect flow of said whole blood sample through said first channel or said second channel into its corresponding container.

In another embodiment described herein, a method of manufacturing a sample collection device is provided comprising forming one portion of a sample collection device having at least two channels configured to simultaneously draw the fluid sample into each of the at least two sample collection channels via a first type of motive force; forming sample containers, whereupon the containers are configured to be coupled to the sample collection device to the provide a second motive force different from the first motive force use to collect the samples to move bodily fluid sample from the channels into the containers.

In another embodiment described herein, computer executable instructions are provided for performing a method comprising: forming one portion of a sample collection device having at least two channels configured to simultaneously draw the fluid sample into each of the at least two sample collection channels via a first type of motive force.

In another embodiment described herein, computer executable instructions for performing a method comprising: forming sample containers, whereupon the containers are configured to be coupled to the sample collection device to provide a second motive force different from the first motive force use to collect the samples to move bodily fluid sample from the channels into the containers.

In yet another embodiment described herein, a device for collecting a bodily fluid sample from a subject, the device comprising: means for drawing the bodily fluid sample into the device from a single end of the device in contact with the subject, thereby separating the fluid sample into two separate samples; means for transferring the fluid sample into a plurality of sample containers, wherein the containers provide a motive force to move a majority of the two separate samples from the pathways into the containers.

In one embodiment, the desired range of channel surface area relative to the surface area of the separator on that side of the separator is in the range of about 35% to 70%. Optionally, the desired range of channel surface area relative to the surface area of the separator on that side of the separator is in the range of about 40% to 70%. Optionally, the desired range of channel surface area relative to the surface area of the separator on that side of the separator is in the range of about 50% to 60%.

In yet another embodiment, a method is provided comprising collecting a bodily fluid sample into a collection channel, the collection channel comprising a first opening and a second opening, and being configured to draw the bodily fluid via capillary action from the first opening towards the second opening; and using a separator along the sample collection channel to remove formed component from the sample prior to and when outputting to the sample container.

In yet another embodiment, a method is provided comprising collecting a bodily fluid sample into device having a first collection channel and a second collection channel, the collection channel comprising a first opening and a second opening, and being configured to draw the bodily fluid via capillary action from the first opening towards the second opening; using a separator along the first sample collection channel to remove formed component from the sample prior to and when outputting to the sample container; wherein when the bodily fluid sample is blood, the device outputs both blood and plasma, each from separate outlets, from the one sample collected into the device.

In one embodiment described herein, it is desirable to use separation materials on a bodily fluid to allow for plasma-based assays. The desired list of assays includes not only large molecules such as proteins and lipids, but also smaller metabolites such as those that are part of the complete metabolic panel and examples include but are not limited to glucose, calcium, magnesium, etc. . . . Since the plasma separation materials were not primarily designed for these assays but for use in select types of test-strip based assays, the hemolysis-preventing agent used in these materials can interfere with other assay chemistries.

In the case of at least some bodily fluid separation materials described herein, the separation material may have a coating of a protective material such as but not limited to an anti-hemolytic material like single and/or double alkyl chain N-oxides of tertiary amines (NTA). Alternatively, separation material coating can constitute a combination of an anti-hemolytic (such as surfactant, protein, sugar, or a combination of these), alongside an anti-coagulant (such as EDTA and its derivatives or Heparin). NTA generally does not interfere with several large molecule assays. NTA, however, is a chelating agent that strongly binds to di-valent cations such as calcium and magnesium ions. Unfortunately, this results in a very strong interference in certain assays used to measure, for example and not limitation, calcium and magnesium concentrations and also for assays where Ca and Mg are co-factors for enzymes which are part of the reaction. This can result in significant errors for such assays.

One or more of the embodiments described herein provide the benefits of the anti-hemolytic material but also provide a much reduced downside effect of the anti-hemolytic material leaching into the bodily fluid and altering the assay results. It should be understood that the coating, in some embodiments, can be one or more of the following: anti-coagulant, anti-hemolytic, and molecules for surface coverage. Any of these may interfere with assays. Some embodiments disclosed herein are directed toward multi-region separation material structures with capture region(s) and pass-through region(s) with different surface treatments.

Optionally, these separation materials may be asymmetric or non-asymmetric separation materials. Some embodiments have bi-layer, tri-layer, or other multi-layer configurations. Some embodiments may be continuously asymmetric with the asymmetric region extending from an upper surface of the material to a lower surface of the material. Optionally, some embodiment may have only one or more portions of the material that are asymmetric while one or more other regions are isotropic in terms of pore size. Some embodiments may have an asymmetric material that is then bonded to at least another material that is isotropic to create a desired pore size distribution profile. In such an embodiment, the asymmetric region may have the larger pore sizes and be coated with anti-hemolytic material. Some embodiments can have separation materials with gradation in coating material thickness and/or coverage to position material such as the hemolysis-preventing material in areas where the material is likely to be in contact with formed components captured by the separation material.

By way of non-limiting example, some separation materials may be washed in a manner the preferentially removes the anti-hemolytic material from at least one region of the separation material, such as the inner portions of the separation material, but not the exterior portions that are more likely to come into direct contact with formed components of the bodily fluid. Other variations or alternative coating schemes to create separation materials or filter structures with areas of leaching and non-leaching materials are not excluded. Optionally, separation materials can also be coated with at least two different materials that may both leach into the bodily fluid, but at least one of these materials that may leach into the fluid does not impact assay measurements and can be used to overcoat the other material and thus decrease the surface area exposure of the other material to the bodily fluid.

Optionally, the separation material comprises an asymmetric porous membrane. Optionally, the separation material is a mesh. Optionally, the separation material comprises polyethylene (coated by ethylene vinyl alcohol copolymer). Optionally, at least a portion of the separation material comprises a polyethersulfone. Optionally, at least a portion of the separation material comprises an asymmetric polyethersulfone. Optionally, at least a portion of the separation material comprises polyarylethersulfone. Optionally, at least a portion of the separation material comprises an asymmetric polyarylethersulfone. Optionally, at least a portion of the separation material comprises a polysulfone. Optionally, the separation material comprises an asymmetric polysulfone. Optionally, the separation material comprises a cellulose or cellulose derivative material. Optionally, the separation material comprises polypropylene (PP). Optionally, the separation material comprises polymethylmethacrylate (PMMA).

In one non-limiting example, a bodily fluid separation material is provided comprising a formed component capture region having an anti-hemolytic surface layer; a bodily fluid pass-through region comprising pass-through openings sized so that formed components do not enter the bodily fluid pass-through region and a reduced amount of fluid leaching material relative to than the capture region, wherein during separation material use, bodily fluid enters the capture region prior to entering the pass-through region.

In one non-limiting example, a bodily fluid separation material is provided comprising an anti-hemolytic, formed component capture region; a bodily fluid pass-through region comprising pass-through openings sized so that formed components do not enter the bodily fluid pass-through region and having a reduced amount of anti-hemolytic material relative to the capture region, wherein during separation material use, bodily fluid enters the capture region prior to entering the pass-through region.

In one non-limiting example, a bodily fluid separation material is provided comprising a first filter region of the separation material having an anti-hemolytic coating and pore spacing sized to constrain formed blood components therein; a second filter region of the separation material having pore spacing smaller than pore spacing of the first filter region with pores sized so that formed components do not enter the second filter region and configured to have an amount of anti-hemolytic coating less than that of the first region.

In one non-limiting example, a bodily fluid separation material is provided comprising a percolating network configured to capture formed blood components: a first region of the percolating network with an anti-hemolytic coating on structures in the region, said network with openings sized and spaced to allow formed blood components to enter the first region but constraining blood components therein from passing completely through the first region; a second region of the percolating network with a reduced anti-hemolytic coating on structures sized and spaced to prevent formed blood components from entering the second region; wherein bodily fluid passes through the first region prior to reaching the second region.

One or more of the embodiments described herein may include one or more of the following features. By way of non-limiting example, a separation material may be a mesh. Optionally, at least a portion of the separation material comprises a polyethersulfone. Optionally, at least a portion of the separation material comprises an asymmetric polyethersulfone. Optionally, at least a portion of the separation material comprises polyarylethersulfone. Optionally, at least a portion of the separation material comprises an asymmetric polyarylethersulfone. Optionally, at least a portion of the separation material comprises a polysulfone. Optionally, the separation material comprises an asymmetric polysulfone. Optionally, the anti-hemolytic material on the separation material comprises single and/or double alkyl chain N-oxides of tertiary amines (NTA). Optionally, the first region comprises a first separation material layer and the second region comprises a second separation material layer. Optionally, the separation material comprises a first separation material coupled to a second separation material. Optionally, the separation material comprises at least two separate separation materials. Optionally, at least another region of the separation material between the first region and the second region. Optionally, the first region is in fluid communication with the second region. Optionally, the first region is spaced apart from the second region.

In one non-limiting example, a method of forming a bodily fluid separation material is provided comprising coating the separation material with an anti-hemolytic coating on a first region and a second region of the separation material; reducing anti-hemolytic effect of the second region of the separation material relative to the first region, wherein when the separation material is in operation, bodily fluid passes through the first region prior to reaching the second region.

In one non-limiting example, a method of forming a bodily fluid separation material is provided comprising coating at least a first region of the separation material with an anti-hemolytic coating; not coating at least second region of the separation material with the anti-hemolytic coating.

One or more of the embodiments described herein may include one or more of the following features. By way of non-limiting example, reducing the anti-hemolytic effect may comprise washing off at least a portion of the anti-hemolytic coating on the second region. Optionally, washing off comprises directing solvent through the separation material. Optionally, washing off comprises soaking only a portion of the separation material in a solvent. Optionally, the anti-hemolytic effect comprises adding another coating of a different material over the anti-hemolytic coating on the second region. Optionally, reducing the anti-hemolytic effect comprises treating the separation material to bring its electrical charge state to a neutral state and thus reduce the attraction of ions that increase the anti-hemolytic effect.

In one non-limiting example, a device is provided for collecting a sample from a subject and outputting a filtrate from the sample.

In one non-limiting example, a device is provided device for collecting a sample from a subject and forming a filtrate from at least a portion of the sample.

In one non-limiting example, a method is provided of using a device for collecting a sample from a subject and outputting a filtrate from the sample.

In one non-limiting example, a method is provided of processing a formed component separation membrane.

In one non-limiting example, a method is provided of processing a formed component separation material.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

INCORPORATION BY REFERENCE

All publications, patents, and patent applications mentioned in this specification are herein incorporated by reference to the same extent as if each individual publication, patent, or patent application was specifically and individually indicated to be incorporated by reference. However, in the event of a conflict between the content of the present express disclosure and the content of a document incorporated by reference herein, the content of the present express disclosure controls.

COPYRIGHT

This document contains material subject to copyright protection. The copyright owner (Applicant herein) has no objection to facsimile reproduction of the patent documents and disclosures, as they appear in the US Patent and Trademark Office patent file or records, but otherwise reserves all copyright rights whatsoever. The following notice shall apply: Copyright 2013-14 Theranos, Inc.

BRIEF DESCRIPTION OF THE DRAWINGS

FIGS. 47A-48B show various views of sample wetting of a separator according to embodiments described herein.

DESCRIPTION OF THE SPECIFIC EMBODIMENTS

Figure 1:
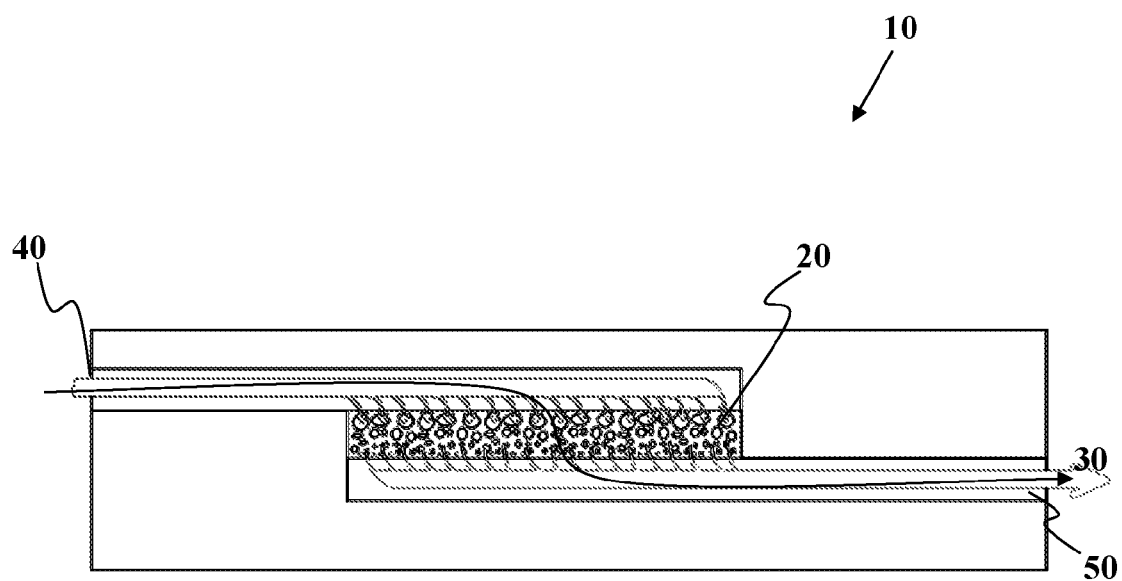
FIG. 1 shows a schematic view of a device according to one embodiment described herein.

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a compound" may include multiple compounds, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for a sample collection unit, this means that the sample collection unit may or may not be present, and, thus, the description includes both structures wherein a device possesses the sample collection unit and structures wherein sample collection unit is not present.

As used herein, the terms "substantial" means more than a minimal or insignificant amount; and "substantially" means more than a minimally or insignificantly. Thus, for example, the phrase "substantially different", as used herein, denotes a sufficiently high degree of difference between two numeric values such that one of skill in the art would consider the difference between the two values to be of statistical significance within the context of the characteristic measured by said values. Thus, the difference between two values that are substantially different from each other is typically greater than about 10%, and may be greater than about 20%, preferably greater than about 30%, preferably greater than about 40%, preferably greater than about 50% as a function of the reference value or comparator value.

As used herein, a "sample" may be but is not limited to a blood sample, or a portion of a blood sample, may be of any suitable size or volume, and is preferably of small size or volume. In some embodiments of the assays and methods disclosed herein, measurements may be made using a small volume blood sample, or no more than a small volume portion of a blood sample, where a small volume comprises no more than about 5 mL; or comprises no more than about 3 mL; or comprises no more than about 2 mL; or comprises no more than about 1 mL; or comprises no more than about 500 µL; or comprises no more than about 250 µL; or comprises no more than about 100 µL; or comprises no more than about 75 µL; or comprises no more than about 50 µL; or comprises no more than about 35 µL; or comprises no more than about 25 µL; or comprises no more than about 20 µL; or comprises no more than about 15 µL; or comprises no more than about 10 µL; or comprises no more than about 8 µL; or comprises no more than about 6 µL; or comprises no more than about 5 µL; or comprises no more than about 4 µL; or comprises no more than about 3 µL; or comprises no more than about 2 µL; or comprises no more than about 1 µL; or comprises no more than about 0.8 µL; or comprises no more than about 0.5 µL; or comprises no more than about 0.3 µL; or comprises no more than about 0.2 µL; or comprises no more than about 0.1 µL; or comprises no more than about 0.05 µL; or comprises no more than about 0.01 µL.

As used herein, the term "point of service location" may include locations where a subject may receive a service (e.g. testing, monitoring, treatment, diagnosis, guidance, sample collection, ID verification, medical services, non-medical services, etc.), and may include, without limitation, a subject's home, a subject's business, the location of a healthcare provider (e.g., doctor), hospitals, emergency rooms, operating rooms, clinics, health care professionals' offices, laboratories, retailers [e.g. pharmacies (e.g., retail pharmacy, clinical pharmacy, hospital pharmacy), drugstores, supermarkets, grocers, etc.], transportation vehicles (e.g. car, boat, truck, bus, airplane, motorcycle, ambulance, mobile unit, fire engine/truck, emergency vehicle, law enforcement vehicle, police car, or other vehicle configured to transport a subject from one point to another, etc.), traveling medical care units, mobile units, schools, day-care centers, security screening locations, combat locations, health assisted living residences, government offices, office buildings, tents, bodily fluid sample acquisition sites (e.g. blood collection centers), sites at or near an entrance to a location that a subject may wish to access, sites on or near a device that a subject may wish to access (e.g., the location of a computer if the subject wishes to access the computer), a location where a sample processing device receives a sample, or any other point of service location described elsewhere herein.

As used herein, the term "separator" may include a mesh, a filter, a membrane, a porous membrane, an asymmetric porous membrane, a semipermeable hollow fiber membrane, a percolating network structure, a material that can be used for size-exclusion of objects greater than a certain dimension, or other filtering material. Materials useful for the preparation of the separating material may be selected from the group comprising polyethylene (coated by ethylene vinyl alcohol copolymer), polyacrylates, polystyrene, polyethylene oxide, cellulose, cellulose derivatives, polyethersulfone (PES), polypropylene (PP), polysulfone (PSU), polymethylmethacylate (PMMA), polycarbonate (PC), polyacrylonitrile (PAN), polyamide (PA), polytetrafluorethylene (PTFE), cellulose acetate (CA), regenerated cellulose, and blends or copolymers of the foregoing, or blends or copolymers with hydrophilizing polymers, including with polyvinylpyrollidone (PVP) or polyethyleneoxide (PEO). Suppliers of such materials and/or membranes include but are not limited to BASF, Advanced Microdevices P. Ltd., International Point of Care Inc., Gambro Lundia AB, Asahi Kasei Kuraray Medical Co., Ltd., GE Healthcare (Whatman division), or the like.

As used herein, the terms "sample" and "biological sample" refer to a blood, urine, sputum, tears, material(s) from a nasal swab, throat swab, cheek swab, or other bodily fluid, excretion, secretion, or tissue obtained from a subject. These terms are inclusive of an entire sample and of a portion of a sample. As used herein, reference to a fluid sample includes reference to a sample and a biological sample. Such samples may include fluids into which material has been deposited, where such material may be obtained from a nasal swab, throat swab, cheek swab, or other sample which may include solid or semi-solid material, whether along with or without natural fluids. Such fluids and samples comprise fluid samples and sample solutions.

As used herein, the term "formed component" may include solid, semi-solid, or cellular structures such as but not limited to red blood cells, white blood cells, platelet, or other components that may be found in a sample, a biological sample, bodily fluid, or natural fluid.

As used herein, the terms "fill" and "filled" and their grammatical equivalents, e.g., as used in phrases such as "a vessel may be filled with a sample solution" refer to the transfer of any amount, including partial filling and complete filling. These terms as used herein do not require that such filling completely fill a container, but include any lesser amount of filling as well.

It should be understood that the devices herein can be configured for use with sample applied to the device, sample drawn into the device by capillary force, sample delivered into the device by way of venipuncture, sample delivered into the device by way of arterial puncture, nasal swab, tear collection, collection from any open wound, biopsy, or other sample delivery or acquisition technique and is not limited to any specific example described herein.

Referring now to FIG. 1, one embodiment of a formed component separation device will now be described. FIG. 1 shows a side cross-sectional view of a device 10 having a formed component separator 20 positioned along a pathway as indicated by arrow 30. In this non-limiting example, the device 10 has at least one sample inlet 40 for receiving a liquid sample that has the formed components there and at least a first outlet 50 for outputting only a liquid portion of the formed component liquid sample. As seen in FIG. 1, the pathway 30 fluidically couples the sample inlet with the first outlet. FIG. 1 also shows that sample such as but not limited to blood flows from the inlet 40 and into and/or over the formed component separator 20. In this non-limiting example, blood enters the formed component separator 20, where blood cells are trapped based on the principle of size exclusion. The formed component separator 20, in one embodiment, may have a plurality of pores wherein those on one surface are significantly smaller than those on another surface of the separator 20. In this manner, the cells in the blood can enter the separator 20 through the larger pores but cannot pass completely through the separator due to the much smaller pores on the output side of the separator 20.

As the sample flows across the separator 20, the liquid portion of the sample such as but not limited to plasma is pulled away from the back of the separator 20 via a combination of capillary action and/or applied pressure differential. Plasma flows away from the separator 20 as indicated by arrow 30. In one embodiment, the walls within the device 10 may be coated with material such as but not limited to anti-coagulant for mixing with the sample during filling.

Figure 2:
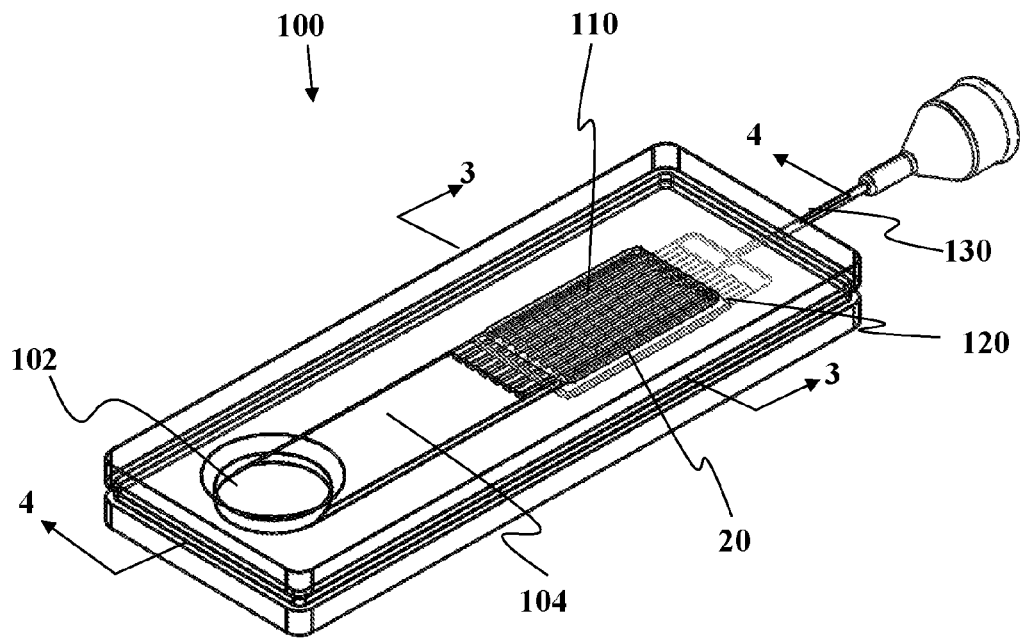
FIGS. 2 to 4 show various views of a device according to one embodiment described herein.

Referring now to FIG. 2, another embodiment of a formed component separation device will now be described. In this non-limiting example, the device 100 has an inlet 102 that is open towards a top surface of the device 100. The inlet 102 is connected by a channel 104 to a distributor 110 that preferentially spreads the sample over the separator 20. The liquid portion of the sample is outputted to the collector 120 which may be directed to an external channel 130 such as a needle or adapter channel. It should be understood that the distributor 110 is not restricted to any particular structure or material and may be a plurality of capillary channels or tubes that distribute the sample over the membrane. In some embodiments, it may be a hydrophilic coating that may be a continuous coating or a patterned coating to draw sample to flow over the membrane.

Figure 3:
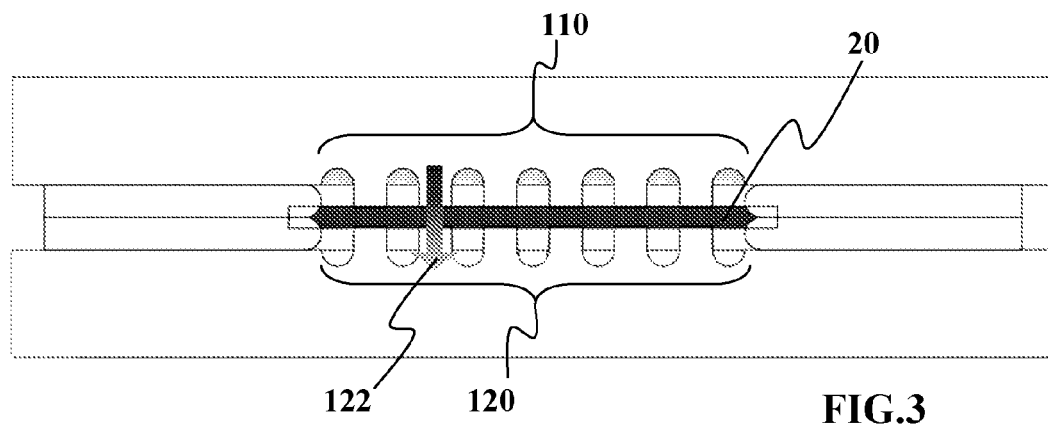
Figure 4:
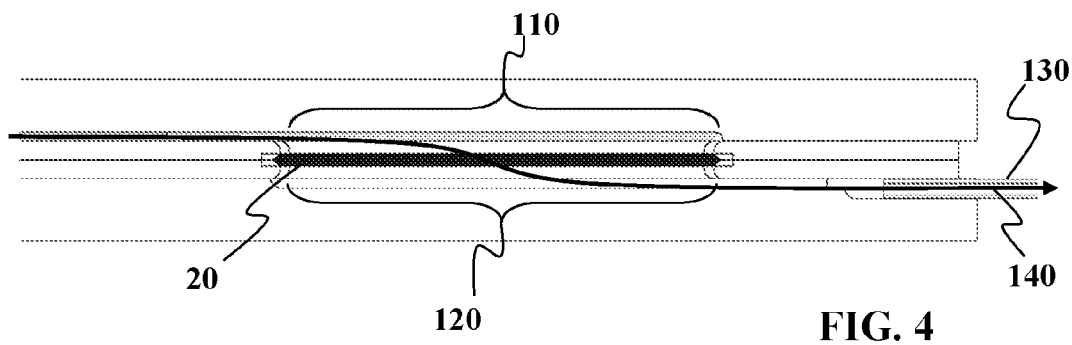

Referring now to FIG. 3, a cross-sectional view of one portion of the device 100 (as indicated by arrows 3-3 in FIG. 2) shows some of the details regarding this embodiment of the distributor 110 that preferentially spreads the sample over the separator 20, and the collector 120 which draws liquid away from the separator 20. Sample will flow across the separator 20 as indicated by arrow 122. In this non-limiting example, the lead-in channel 130 wicks blood in from the inlet 102 and transports it into the distribution channel network of distributor 110 via capillary action. The distribution channel network comprises a network of capillaries on the blood side of the separator 20. This distributor 110 pulls sample away from the lead-in channel and distributes it evenly over the membrane. In one embodiment, the separator 20 separates plasma from whole blood via a two-step process. One process uses a passive mechanism: gravity and capillary force gradient. A second process uses an active mechanism: application of a pressure differential. These processes can act in a sequential manner or in a simultaneous manner. Capillaries of collector 120 also route the liquid portion of the sample into the extraction port when the pressure differential is applied. Sample flow through the device 100 is indicated by arrow 140.

Figure 5A:
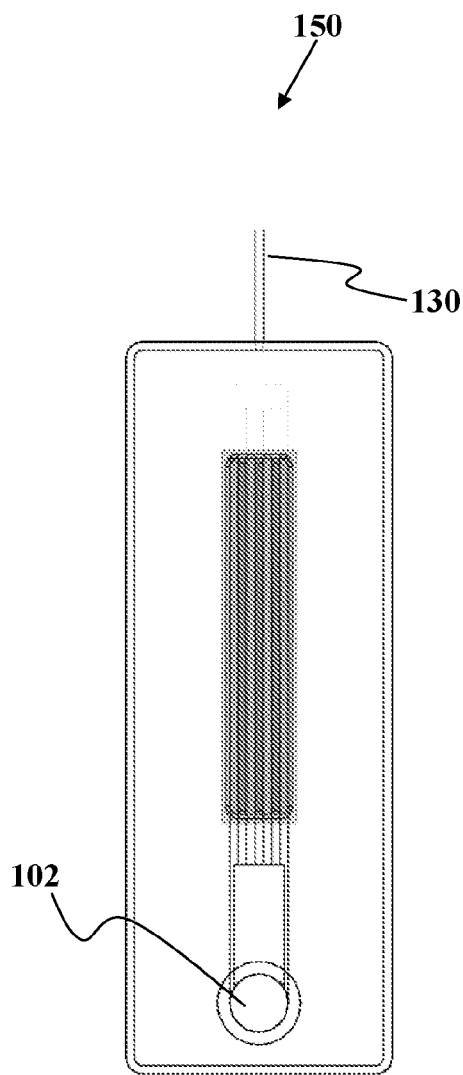
FIGS. 5A-5B show top-down plan views of devices according to embodiments described herein.
Figure 5B:
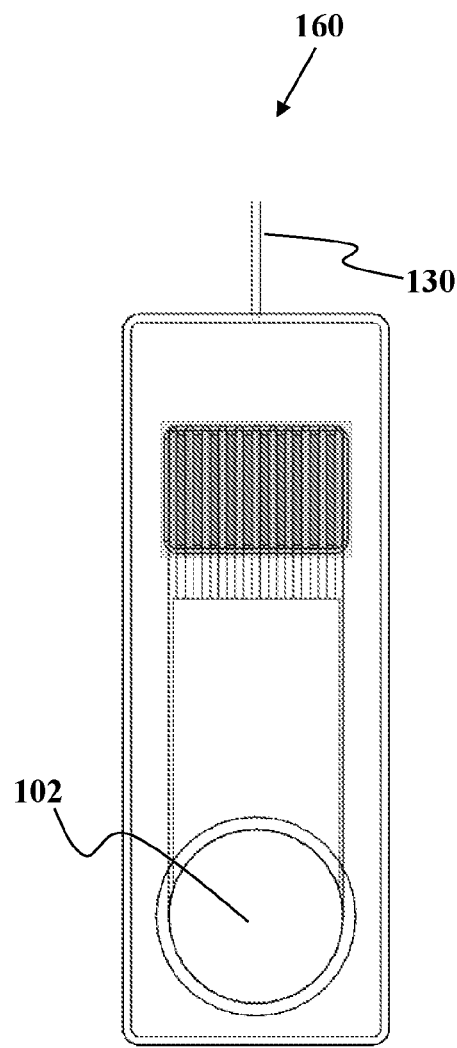

Referring now to FIGS. 5A and 5B, various embodiments of collection devices will now be described. FIG. 5A shows a sample separation device 150 that has an aspect ratio that provides for fewer numbers of channels but increases the length of each of the channels. The length of the membrane along a longitudinal axis of the device, relative to the width may be in a range of about 3:1 to about 5:1. FIG. 5B shows another embodiment of a separation device 160 that has a different aspect ratio which an increased number of capillary channels, but reduced length for each. The length of the membrane along a longitudinal axis of the device, relative to the width may be in a range of about 1:1 to about 1:3. It should also be understood that the cross-sectional size of channels over separator 20 and those beneath the separator 20 can also be different. In one embodiment, the channels in the collector 120 that are beneath the separator 20 are at least 2× smaller in cross-sectional area than those over the channel. In one embodiment, the channels in the collector 120 that are beneath the separator 20 are at least 5× smaller in cross-sectional area than those over the channel. In one embodiment, the channels in the collector 120 that are beneath the separator 20 are at least 10× smaller in cross-sectional area than those over the channel. The decreased size of the channels will increase the capillary pressure and thus preferentially direct liquid portions of the sample towards the output of the device.

Figure 6:
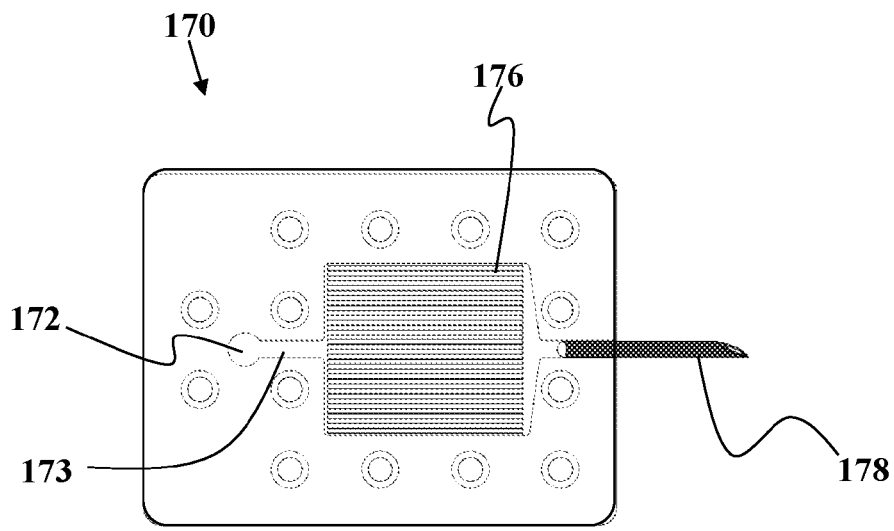
FIGS. 6-7 show various views of a device according to one embodiment described herein.
Figure 7:
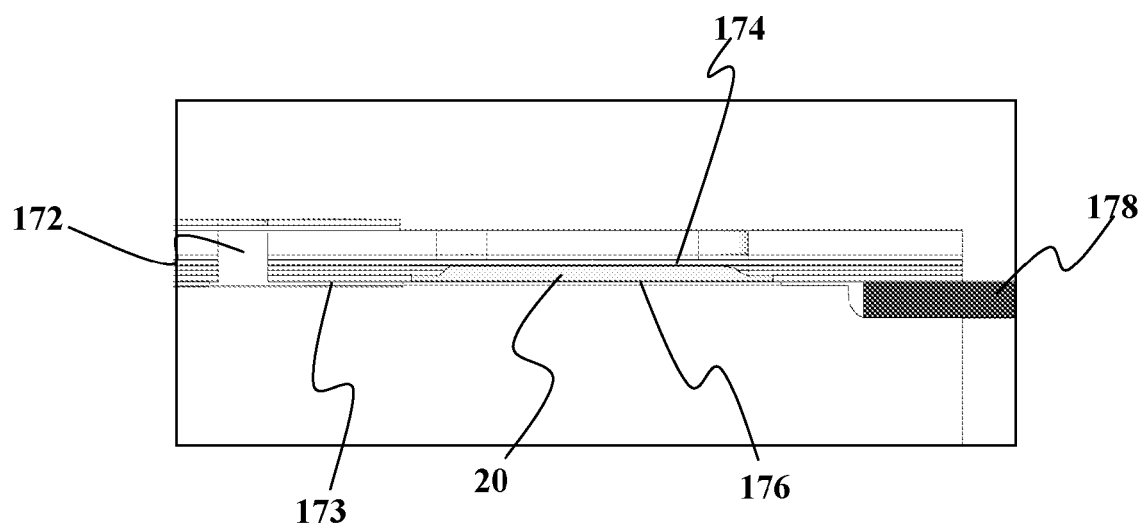

Referring now to FIGS. 6 and 7, yet another embodiment of a sample separation device 170 is shown. FIG. 6 shows a top-down view of a bottom portion of the separation device 170 is shown with a vent 172, a vent inlet channel 173, and a collector 176 is shown with a plurality of channels to draw sample from an underside of the separator 20 (more clearly shown in FIG. 7). An outlet tube 178 such as but not limited to a needle can be used to engage a container such as but not limited to a sealed container with piercable septum or cap, wherein the interior or the container is under vacuum pressure therein to pull liquid sample into the container when it is fluidically engaged by the needle of the outlet tube 178. Optionally, the container may take the form of a test tube-like device in the nature of those marketed under the trademark "Vacutainer" by Becton-Dickinson Company of East Rutherford, N.J.

FIG. 7 shows, in one embodiment, a side cross-sectional view of the device 170. As can be seen, the separator 20 is "sandwiched" between the distributor 174 and the collector 176. The separation material along the first pathway configured to remove formed components from the sample prior to outputting at the first outlet. Processed sample will be outputted through the outlet tube 178 into a container or other receptacle. Some embodiments as seen here may have a funneled portion in the collector 176 to direct sample that has been processed towards the outlet tube 178. By way of example and not limitation, the sample can be applied directly to the distributor 174 or directly to the separator 20.

Figure 8:
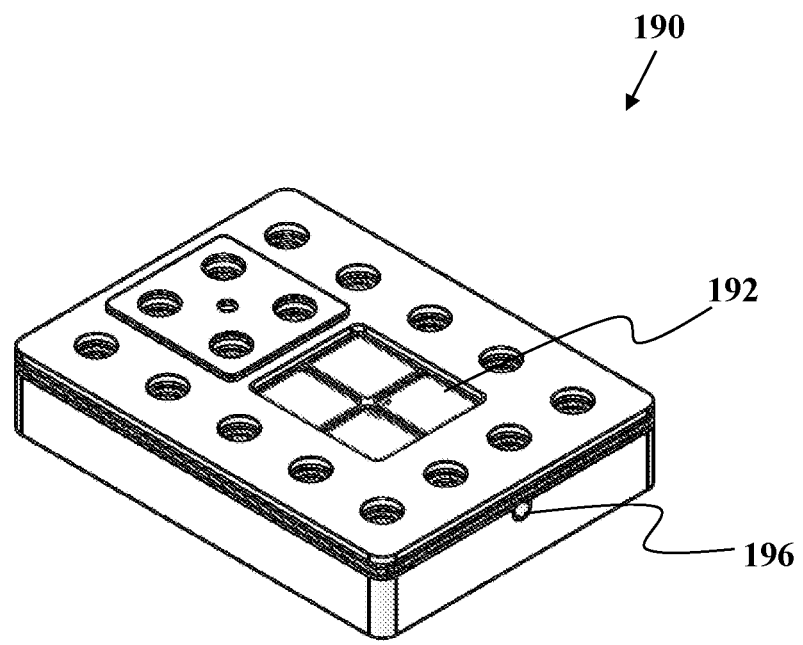
FIGS. 8-9 show various views of a device according to one embodiment described herein.
Figure 9:
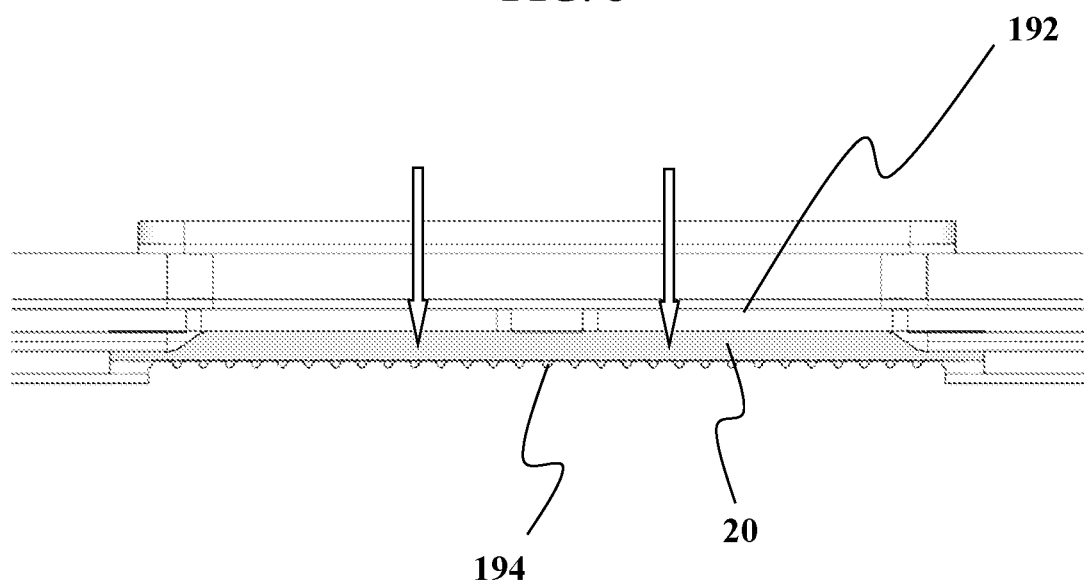

Referring now to FIGS. 8 and 9, a still further embodiment will now be described. FIG. 8 is a perspective view of a sample separation device 190. This embodiment of the sample separation device 190 is configured to allow for direct application of the sample onto the separator by way of opening 192 over the separator. Processed liquid will be drawn by the collector 194 to be output through the outlet 196.

Figure 10:
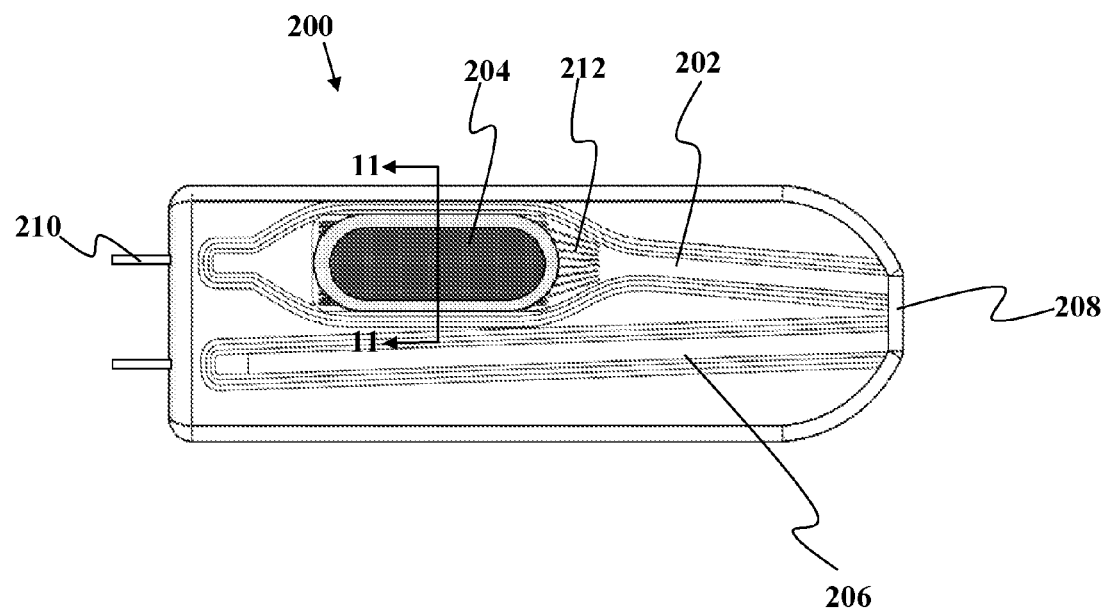
FIGS. 10-11 show various views of a device having at least two sample pathways according to one embodiment described herein.

Referring now to FIG. 10, a sample collection device 200 according to one embodiment herein will now be described. In this non-limiting example, the sample collection device 200 includes a first pathway 202 that is configured to direct sample to a separator 204. The sample collection device 200 also includes a second pathway 206 that collects sample but does not direct it through a formed component separator 204. Both pathways 202 and 206 have openings that are co-located, adjacent, coaxial, or otherwise closely positioned at a distal end 208 of the device 200 that will be in contact with the subject. Optionally, some embodiments may share a common pathway that has a single opening at the distal end 208. The collected sample may exit from one or more adapter channels 210 to one or more sample containers (not shown for ease of illustration). FIG. 10 shows that the distributor 212 may have features that extend beyond the area of the separator 204. These off-membrane features are helpful in drawing the sample towards and over the membrane, particularly as the channel widens to accommodate the membrane.

Figure 11:
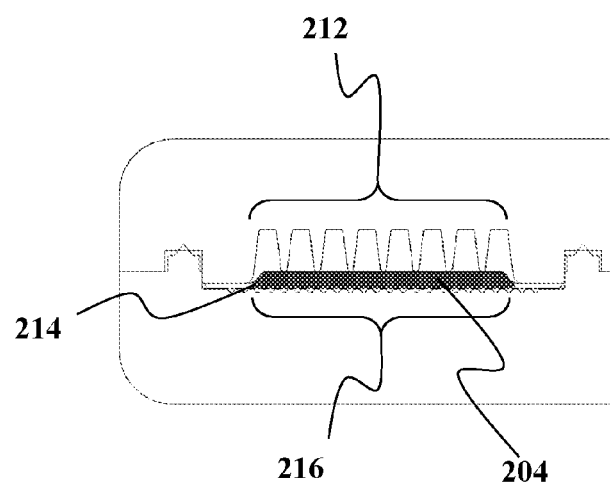

FIG. 11 is a cross-sectional view of one embodiment of the distributor 212 over the separator 204 as indicated by arrows 11-11 in FIG. 10. As seen in FIG. 11, at least a portion of the separator 204 may have reduced thickness area 214 where the material may be thinner or optionally where the material is compressed from its normal thickness to hold the material in place. In one non-limiting example, one purpose of this compressed region is to compress the pores in the membrane and thereby create a seal that is impassable by the formed components. In one non-limiting example, normal separator thickness may be in range of about 100 to about 1000 microns. Optionally, normal separator thickness may be in range of about 200 to about 900 microns. Optionally, normal separator thickness may be in range of about 200 to about 500 microns. Optionally, normal separator thickness may be in range of about 300 to about 500 microns. Optionally, normal separator thickness may be in range of about 300 to about 800 microns. Optionally, normal separator thickness may be in range of about 400 to about 700 microns. Optionally, normal separator thickness may be in range of about 500 to about 600 microns. FIG. 11 also shows that the collector 216 may be a plurality of capillary channels that have a v-shaped cross-section. These are used to draw the liquid only sample to the outputs of the device at adapter channel 210.

Figure 12:
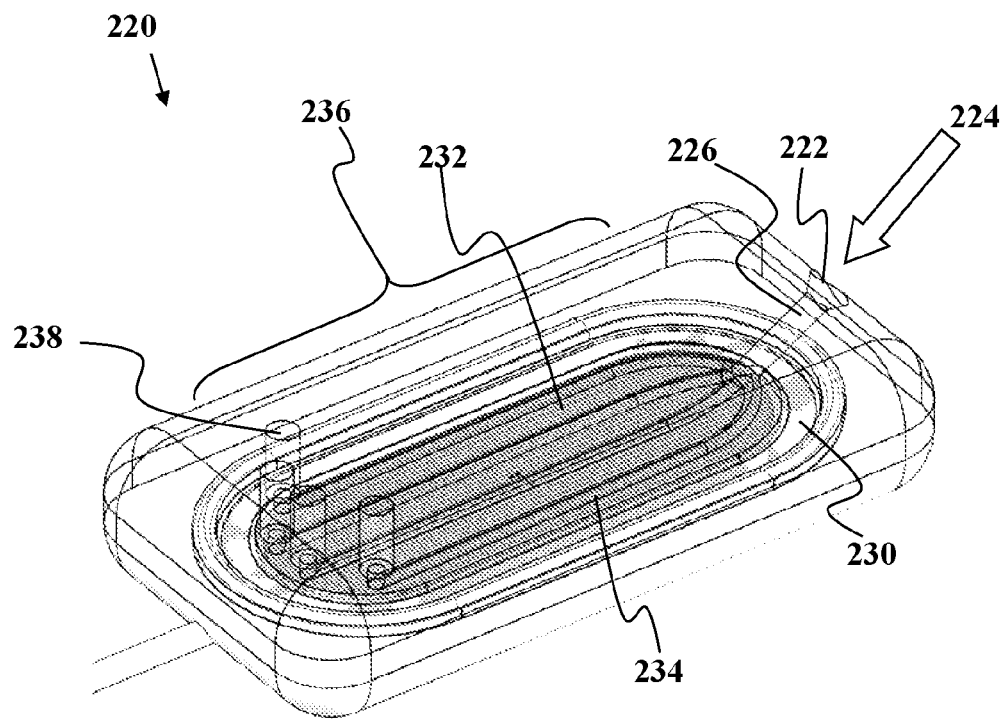
FIGS. 12-13 show various views of a device according to one embodiment described herein.
Figure 13:
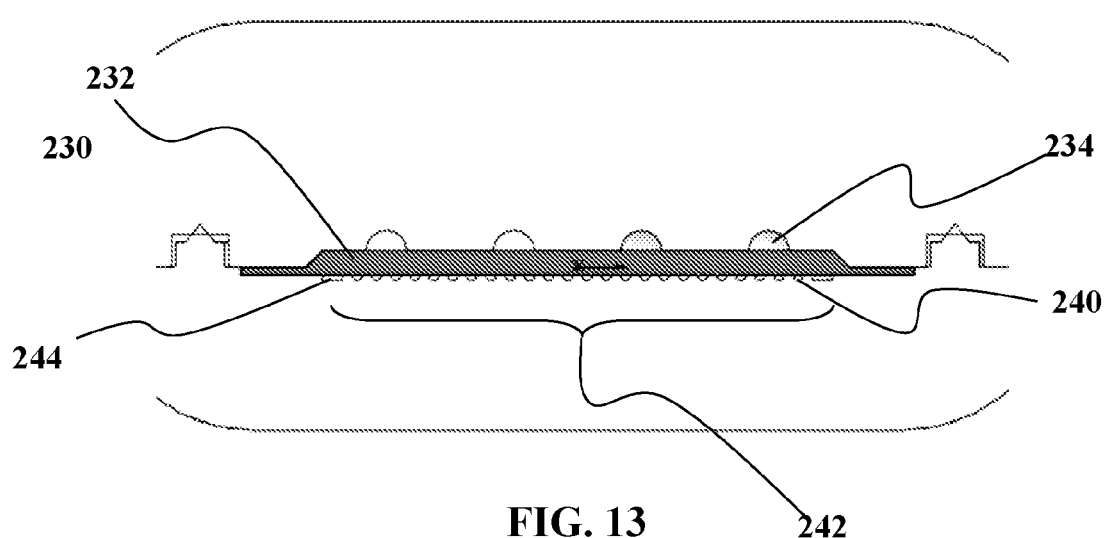

Referring now to FIGS. 12 and 13, a still further embodiment of a sample collection and separator device 220 will now be described. FIG. 12 shows the device 220 as having an inlet 222 for receiving sample as indicated by arrow 224. The sample received at inlet 222 enters a channel 226 that is aligned along an axis configured to intersect the plane in which the separator 228 is positioned. In this manner, the sample when it contacts the separator 228 is placed onto primarily a planar surface of the separator 228. In one embodiment, the peripheral portion 230 of separator 228 is compressed to hold the separator in place and to prevent sample from exiting along the edge of the membrane, instead of through the back and into the collector 232.

At the point of sample contact with the separator 228 and the end of channel 226, the sample contact both the separator 228 and channels 234 of the distributor 236. In this manner as will be discussed in more detail elsewhere herein, the sample is drawn by both the separator and the distributor 236 to be distributed over and/or through the separator. Optionally, this can be beneficial to prevent clogging of sample at any one location or junction point on the separator. Optionally, the distributor may be used to facilitate longitudinal uniformity of the sample with respect to concentration of formed components in the liquid portion of the sample. Optionally, use of the distributor 236 can also speed the filling process. The channels 234 may be coupled to one or more vents 238 that allow for gas or air to be displaced when sample enters the distributor 236. FIG. 12 shows that each channel 234 may have its own individual vent 238. Optionally, some embodiment may have two or more channels 234 couple to share a vent by way of common manifold configuration or the like. As seen, the vents are positioned at the ends of the channels 234 to allow for the channels to fully fill.

FIG. 13 shows a lateral cross-sectional view of one embodiment the device 220 wherein the channels 234 of the distributor 236 are shown over the capillary collection channels 240 of the collector 242. FIG. 13 also shows that not ever channel in the collector 242 has the same cross-sectional shape. By way of non-limiting example, the channels 244 along a perimeter of the collector 242 may have a different shape such as but not limited to a rectangular cross-section that is different from other channels in the collector 242.

Figure 14:
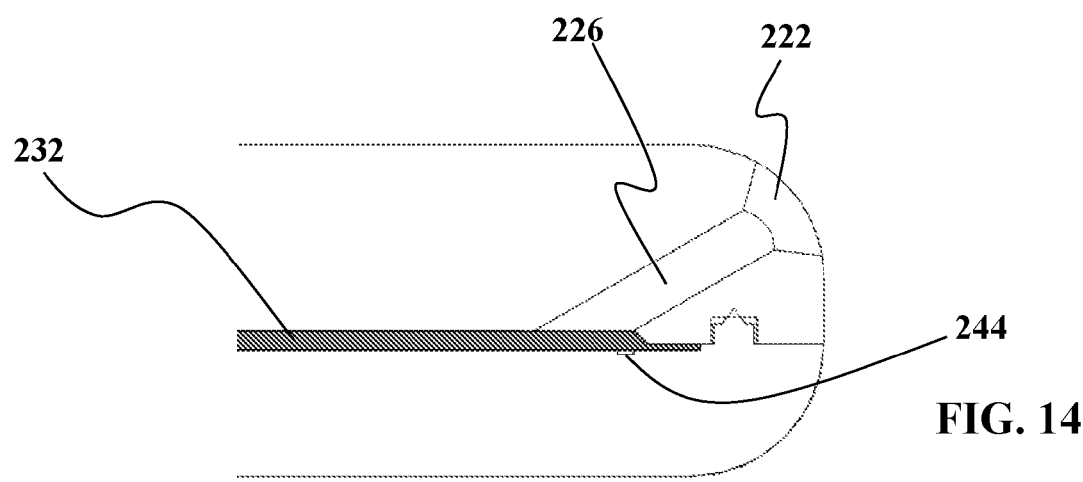
FIGS. 14-19 show cross-sectional views of various configurations for sample inlet openings and channels according to embodiments herein.

Referring now to FIG. 14, a cross-sectional view of one embodiment of a sample inlet channel will now be described. As seen in FIG. 14, the inlet channel 226 directs sample from inlet 222 towards the separator 232. The angled orientation of channel 226 relative to the plane of the separator 232 allows for sample to be placed onto the planar surface of the separator and not relying purely on lateral pulling. The angled cross-sectional shape also increases the area of sample contact to be greater than merely the lateral cross-section of the channel.

Figure 15:
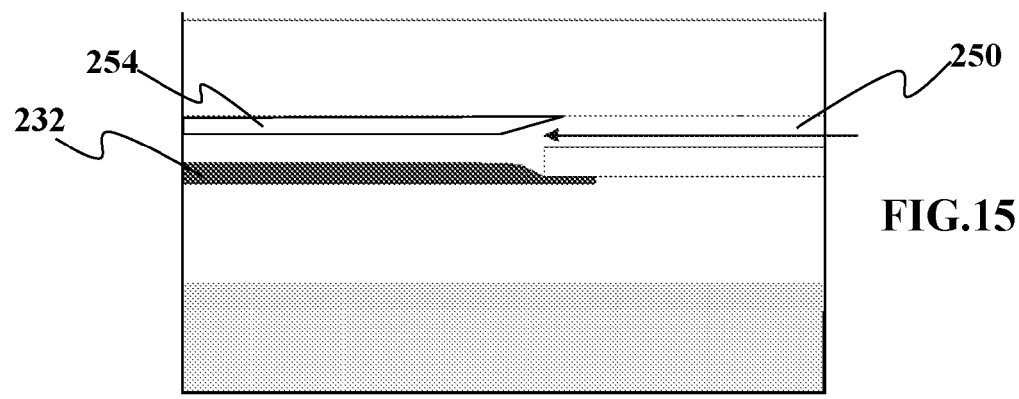
Figure 16:
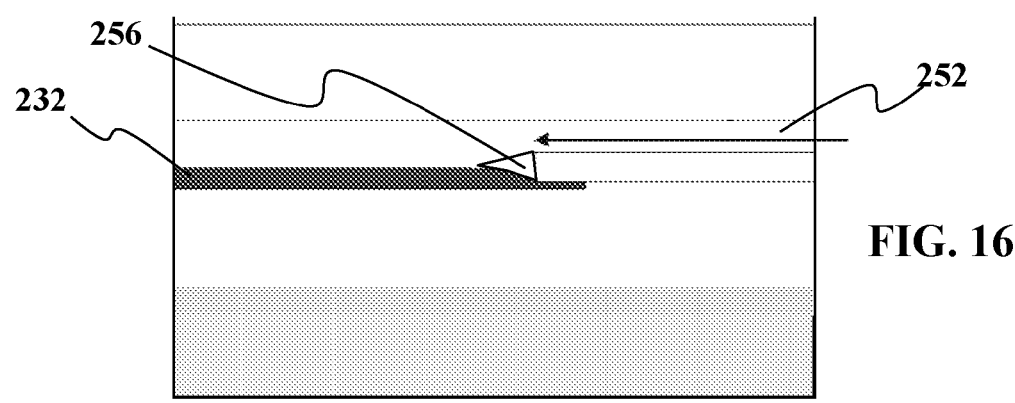

FIGS. 15 and 16 also show other embodiments wherein sample inlet channels 250 and 252 that have sample channel transition features 254 and 256 that minimize detrimental effects due to change in channel dimension. These transitions features may be configured to reduce dimension in one axis (feature 254) or minimize a sudden change in dimension (feature 256) by gradually transitioning the change in dimension over a longer and/or wider area. It should be understood that some embodiments may combine the use of features 254 and 256. Other embodiments herein may also have these features or others that use embody the concepts described herein to minimize detrimental impact of certain channel features. Inlet channel desirably leads to direct contact with the membrane, which in one non-limiting example, is without an intermediary reduction in capillary forces, which can stop the blood flow and prevent distribution.

Figure 17:
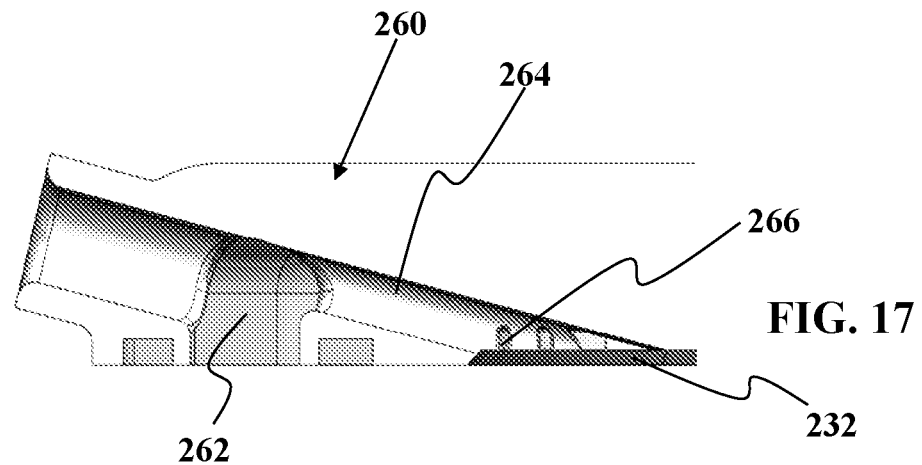
Figure 18:
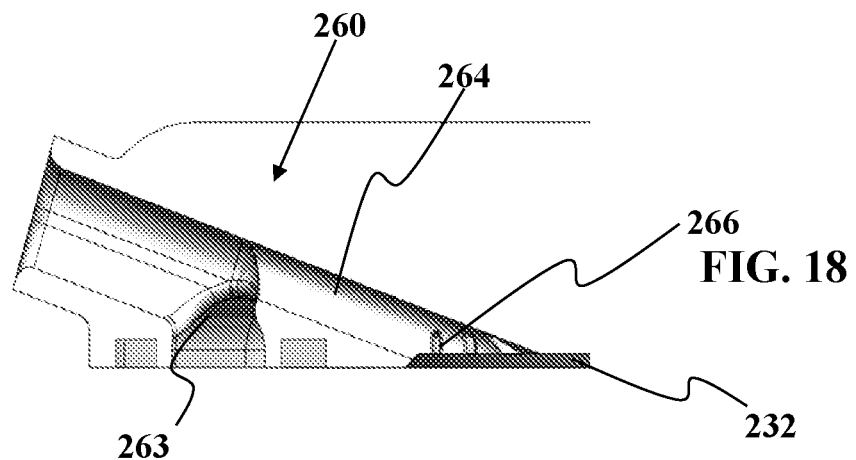
Figure 19:
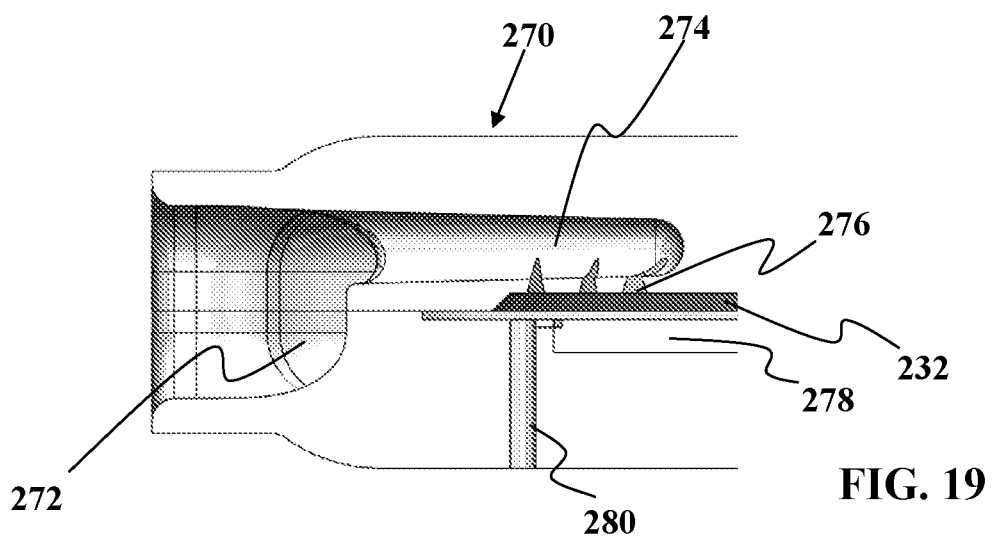

Referring now to FIGS. 17 to 19, other configurations for sample inlet channels according to embodiments herein will now be described. FIG. 17 shows an angled sample inlet channel 260 that has a "splitter" configuration wherein at least one opening of channel 262 couples with the inlet channel 260 to direct a portion of the sample to channel 262. This can be particularly useful in configurations such as but not limited to that shown in FIG. 10 wherein one portion of the sample will be treated to separate formed components from the liquid portion of the sample while other portions of the sample are not treated in the same manner and thus progress down one or more other pathways.

In this non-limiting example, the opening for channel 260 is at least as large as if not larger than the cross-sectional shape of the inlet channel 260. The sample continues in a second portion 264 of the inlet channel 260 to reach the separator 232. The openings 266 of a distributor for the separator 232 can be located at the end portion of the channel 260. As seen in this non-limiting example, the second portion 264 of channel 260 is smaller in cross-sectional area than an initial portion of the channel 260. FIG. 17 also shows that the channel 260 is directing sample at an upper portion of the channel profile to the second portion 264 while the opening for channel 262 collect at least sample in the lower portion of the channel profile. A higher entry point can help with lengthwise blood distribution along the length of the separator by delaying and reducing initial penetration of the separator by the sample as it flows into the distribution volume.

FIG. 18 shows yet another embodiment of the sample inlet channel wherein the opening for channel 263 is now configured to interface only a smaller portion of the channel 260. As seen in FIG. 18, the opening 263 of the channel intersects only a lower portion of the channel profile for channel 260. This can useful to customize the volume of sample that is directed towards each channel.

FIG. 19 shows yet another embodiment wherein the inlet channel 270 connects to the second channel 272 and has a significantly larger cross-sectional profile relative to the second portion 274 of the inlet channel. The second portion 274 is configured to draw sample from an upper portion of the cross-sectional profile of the inlet channel. The openings 276 for the sample distributor draw from the lower portion of the portion 274 to distribute sample over the separator 232. A collector 278 will draw liquid sample from the separator 232. At least one vent 280 can be coupled to the separator 232 to provide a controlled inlet of external atmosphere to facilitate the pull of liquid device. In one non-limiting example, vent 280 may allow at least some venting to occur during the dynamic stage of extraction, in which a pressure differential or other motive force is applied to draw the liquid portion of the sample into at least one collection container. Optionally, the vent 280 may be separated from the collector 278 by the separator 232 to provide a controlled inlet. The vent 280 may couple to compressed portion of the separator 232. The vent 280 may couple to normal portion of the separator 232.

Figure 20:
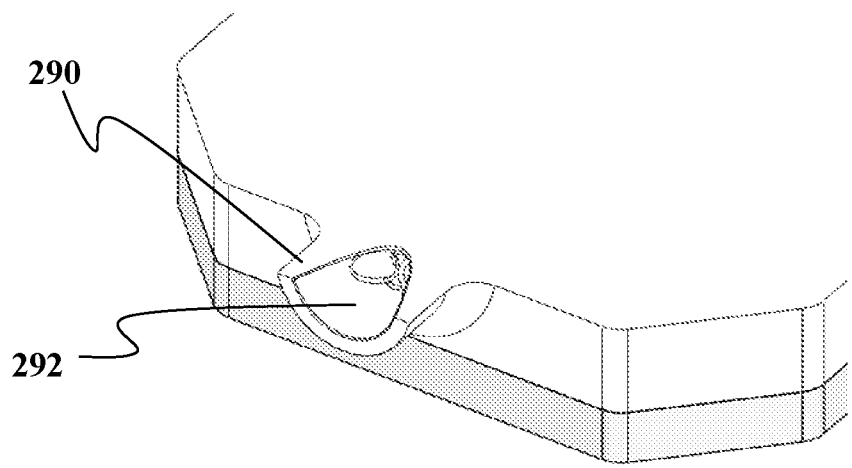
FIGS. 20-21 show views of various configurations for sample inlets according to embodiments herein.
Figure 21:
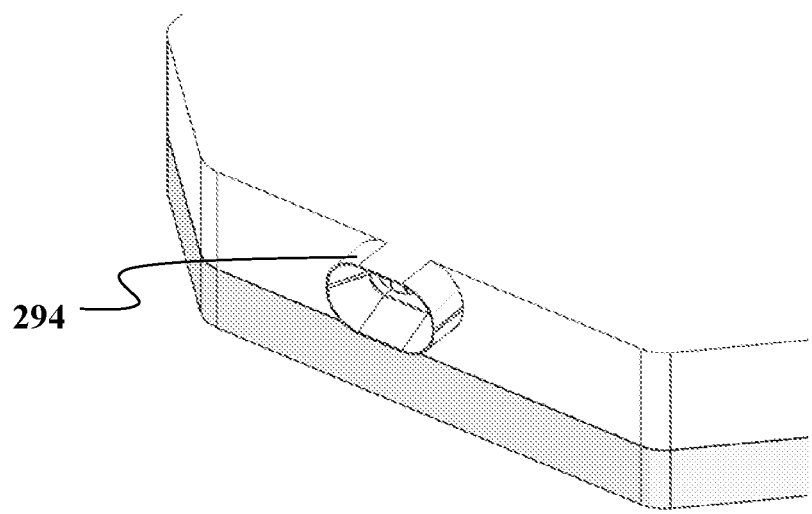

Referring now to FIGS. 20 and 21, various shapes can be configured for use to engage a subject for sample collection according to embodiments herein. FIGS. 20 and 21 both show protrusions for use on collection devices as described herein. FIG. 20 shows a protrusion 290 that is shaped in a scoop or spoon configuration having both vertical and horizontal portions of the opening 292 in the protrusion accessible to the user to collect sample. The opening 292 may lead to a single or multiple pathways in the device.

FIG. 21 shows one embodiment of a protrusion 294 that extends away from the body of the device so that the user is provided a visual cue as to where the contact the device to the subject to collect sample. The opening may be funnel shaped to assist in sample collection and in engagement with the skin of the patient. The protrusion 294 has an opening that may lead to a single or multiple pathways in the device. It should be understood that some embodiments may have protrusions that are shaped to be convex or concave to facilitate engagement of the device protrusion with bead or droplet of bodily fluid sample on the subject. The protrusion may be coated with hydrophilic and/or hydrophobic material to push or pull the sample in a desired direction.

Figure 22:
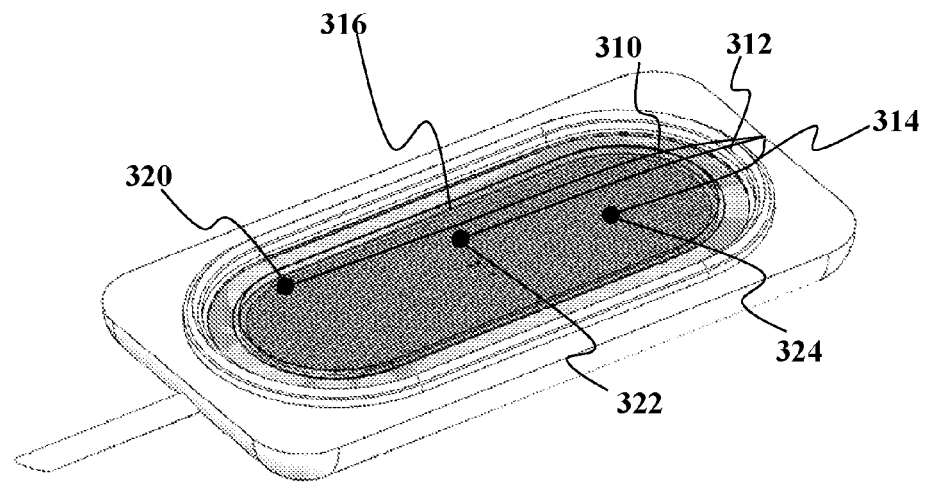
FIGS. 22-28 show various patterns for sample distribution pathways according to embodiments herein.
Figure 23:
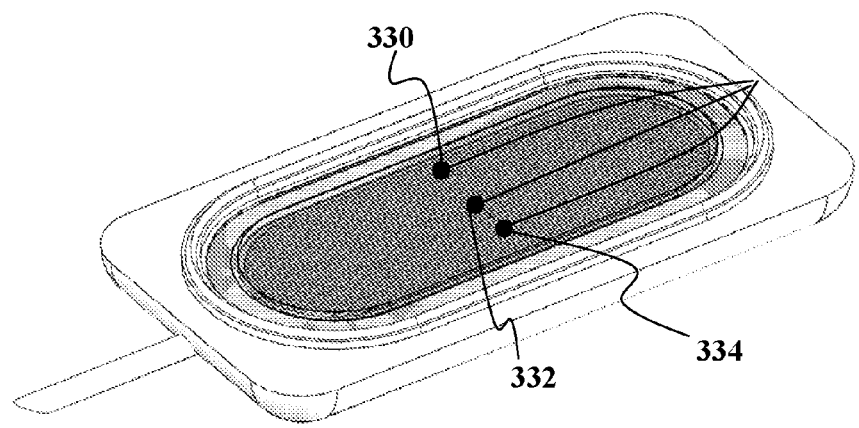
Figure 24:
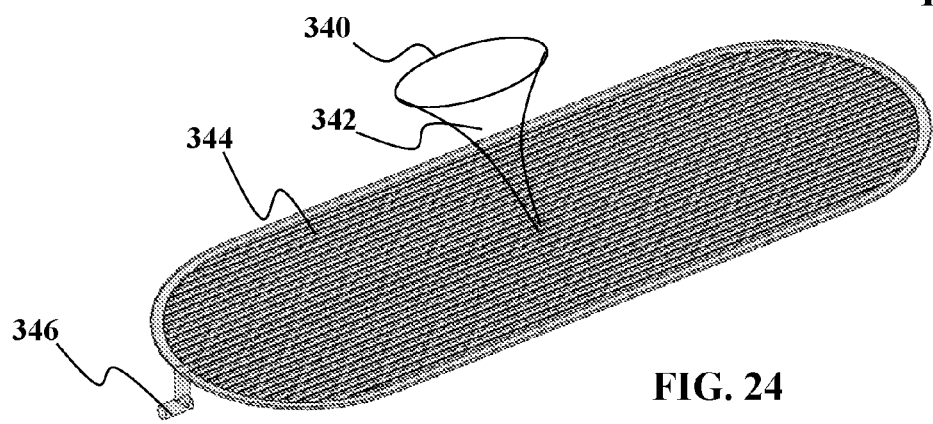

Referring now to FIGS. 22 to 24, it should also be understood that sample can be delivered to one or more different locations on the sample separator according to at least one embodiment herein. As seen in FIGS. 19 to 21, some embodiments may deliver sample to one end of the separator, away from a central portion of the separator. Optionally, some embodiments as seen in FIGS. 22 to 23, deliver sample from an inlet at one end to one or more openings closer to the center of the separator. The sample may be delivered both at the one end and at locations closer to the center.

For example, FIG. 22 shows embodiments of inlet tubes 310, 312, and 314 for use in delivering sample from an inlet on a periphery of the device to one or more locations along a central area of the separator 316. The locations 320, 322, and 324 may be openings or other structures that allow the inlet tubes 310, 312, and 314 to deliver sample to the desired location on the separator 316. FIG. 22 shows that these locations may be distributed over various locations on the separator 316. FIG. 23 shows an embodiment wherein the locations 330, 332, and 334 are located in a line near the central area of the separator. Optionally, some embodiments may use single or multiple combinations of one or more of the structures in FIGS. 19 to 24 to provide a desired sample distribution pattern over the separator. It should be understood that the embodiments herein can deliver the sample directly onto the separator, onto network of distributor channels over the separator, or a combination of the foregoing.

FIG. 24 shows a still further embodiment wherein the inlet is not located at either end of the collection device, but instead has an inlet that is substantially centrally located as seen in FIG. 24. This embodiment shows that the inlet 340 leads to a channel 342 that feeds to a central portion of the separator 344. FIG. 24 is a simplified drawing showing primarily only the separator 344 and an outlet port 346 that draws liquid portion of the sample away from the separator after processing.

Figure 25:
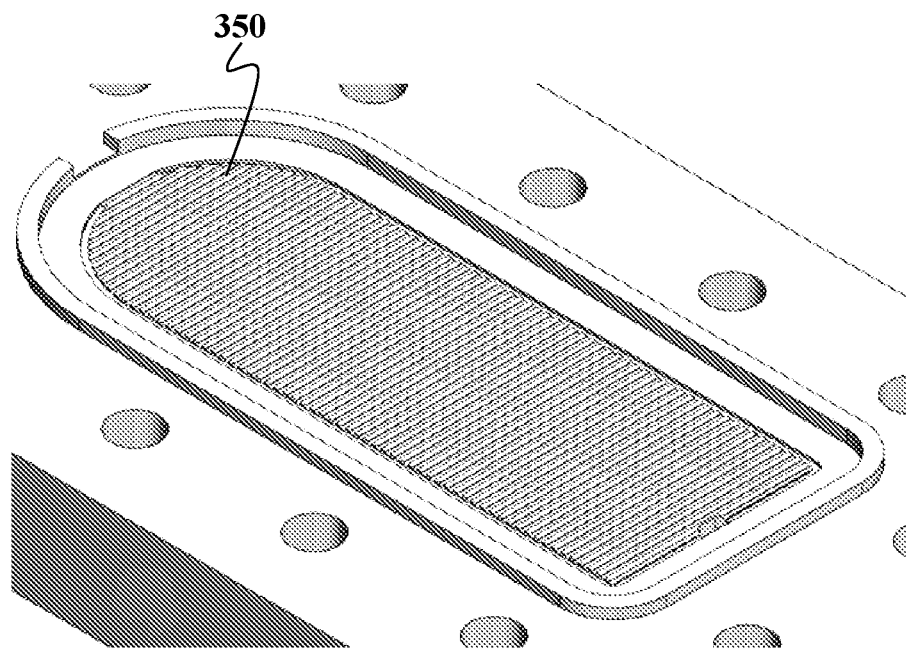
Figure 26:
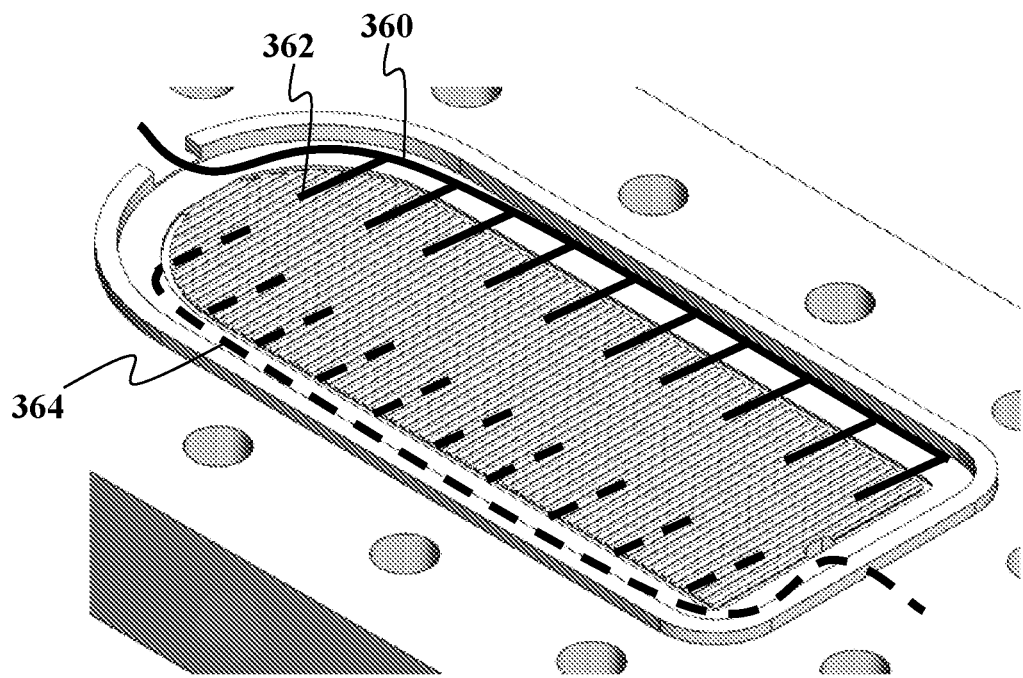

Referring now to the embodiments of FIGS. 25 and 26, it should be understood that the distribution of the channels of the distributor is not limited to the patterns, sizes, or shapes disclosed in the previous figures. As seen in FIG. 25, one embodiment may align all of the channels 350 orthogonal to the longitudinal axis of the device and/or separator. In the embodiment of FIG. 25, this results in a greater number of channels 350, but each has a shorter length. Optionally, the orientation of the channels is not limited to orthogonal to the longitudinal axis of the device. Other angles relative to the longitudinal axis of the device and/or the separator are not excluded. Optionally, some embodiments may use different patterns over different portions of the separator. Optionally, some embodiments can use a combination of patterns over the same area.

It should also be understood that this same or similar pattern of channels can also be implemented on the collector that is used on the opposite side of separator. Optionally, the distributor can use one channel pattern and the collector can use a different channel pattern.

Optionally, some of the sideways capillaries 350 on the collector uses a non-vented configuration. Some of these sideways capillaries 350 demonstrated a different extraction behavior as blood separates. Lengthwise capillaries tend to extract from back of device first, then towards the front. Sideways capillaries 350 extract first towards the middle of the separator and outwards towards front and back of device, which can be used to create a more even extraction process across the separator.

As seen in FIG. 26, some embodiments may also use a configuration having a manifold 360 having a plurality of outlets 362 that can distribute sample over the separator and/or into the distributor. Some embodiments can have shorter or longer outlets 362, depending on the pattern that one desires to deliver sample to the separator and/or distributor. It should also be understood that some embodiments may more than one manifold 360 that delivers sample to the separator and/or distributor. For example, one embodiment may have another manifold 360 deliver sample along the other longitudinal edge of the separator.

FIG. 26 also shows in phantom a potential pattern for a collection manifold 364 for use on the opposite side of the separator for sample collection. This manifold 364 would typically not be used on the same side as the distribution manifold 360 but would instead be on an opposite side of the separator.

Figure 27:
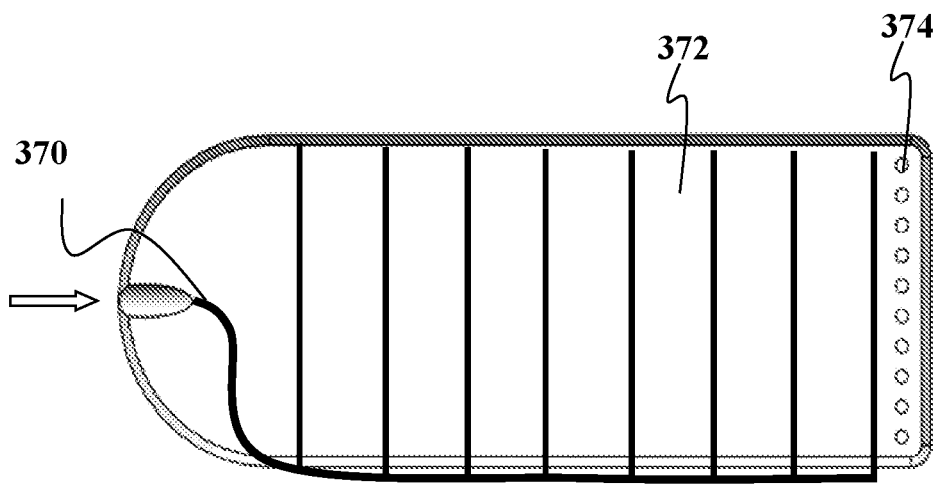

Referring now to FIG. 27, a still further embodiment is shown with a patterned manifold 370 with channels that distribute sample along various locations over the separator 372. FIG. 27 shows that there may be a plurality of vents that allow for gas or air in the separator 372 or other part of the manifold to escape as sample fills the area. It should also be understood that although the manifold 370 is shown with a distribution pattern of substantially same length channels 374, such channels can be pattern to have same, different, repeating, or other patterns of size, length, contact area with the separator, or other dimension to provide a desired performance. It should also be understood that the manifold 370 can be used to directly distribute sample onto the separator or it may opt to deliver sample in a pattern to a distributor which then further distributes the sample over the separator. Some embodiments of the manifold 370 uses tubes with openings at select locations to allow sample to exit. Some embodiments can use channels with at least one open side to distribute sample along a certain length of the separator and/or distributor.

Figure 28:
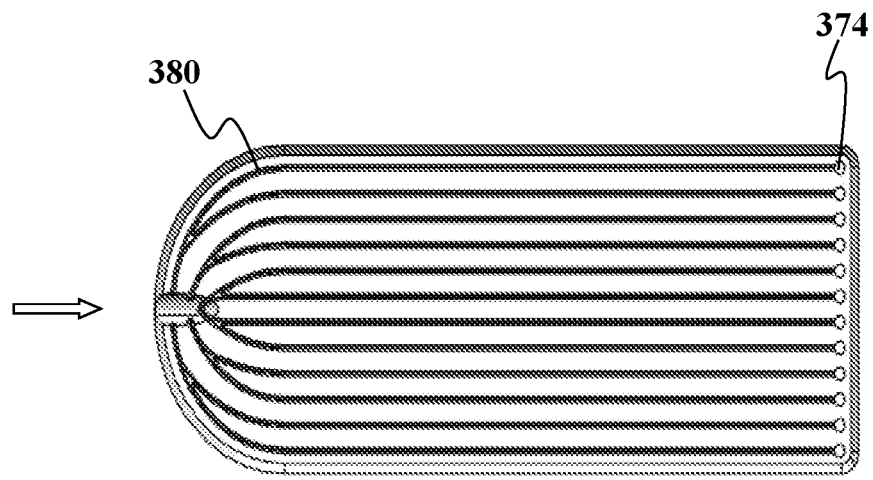

Referring now to FIG. 28, yet another embodiment of a manifold 380 is shown. This can be as a distributor that has twelve channels that distribute sample over the separator. As seen, the channel pattern of manifold 380 initially has six channels leading away from a single inlet channel, and those six channels are each split once to achieve twelve channels.

Figure 29:
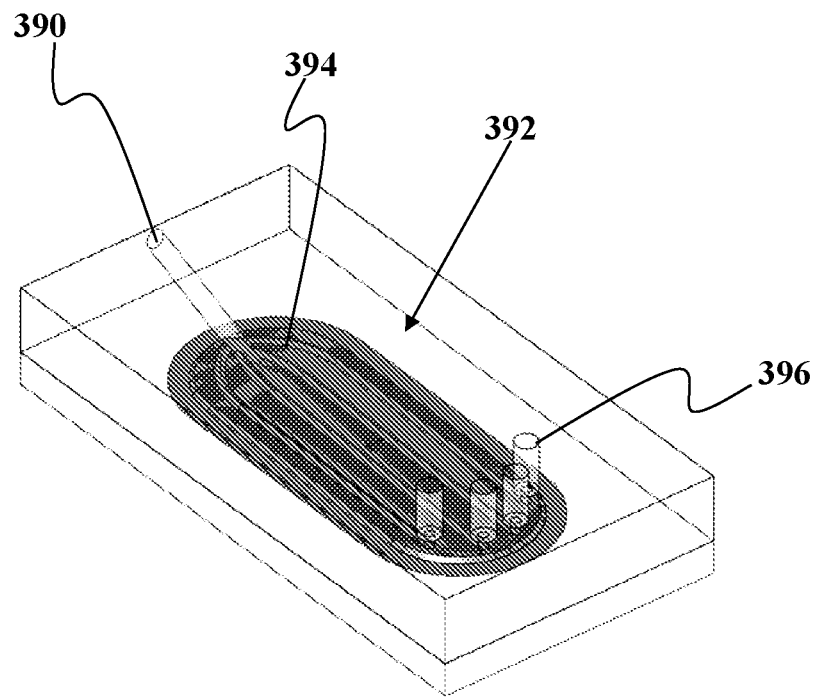
FIGS. 29-30 show various views of a device according to one embodiment described herein.
Figure 30:
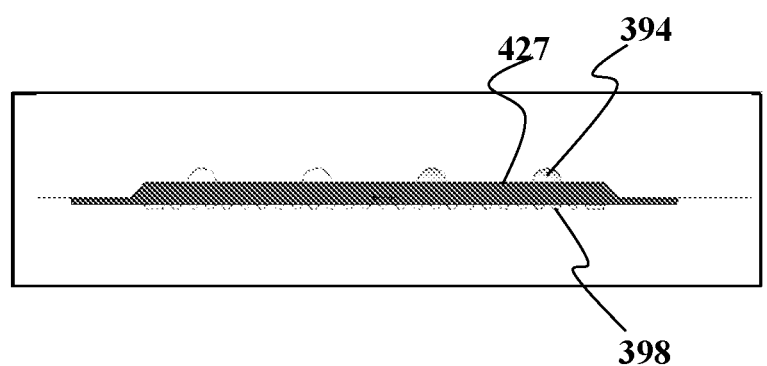

Referring now to FIGS. 29 to 34, still other embodiments showing different combinations of inlet channels and distributors are shown. FIGS. 29 and 30 show a single inlet 390 having a circular cross-sectional shape leading to a multi-channel distributor 392 with channels 394, with each of the channels coupled to its own vent 396, similar to that shown for FIG. 12. It should be understood, however, that embodiments where vents are shared are not excluded. FIG. 30 shows the cross-sectional shape of the channels 394 and their size relative to the capillary channels 398 of the liquid sample collector.

Figure 31:
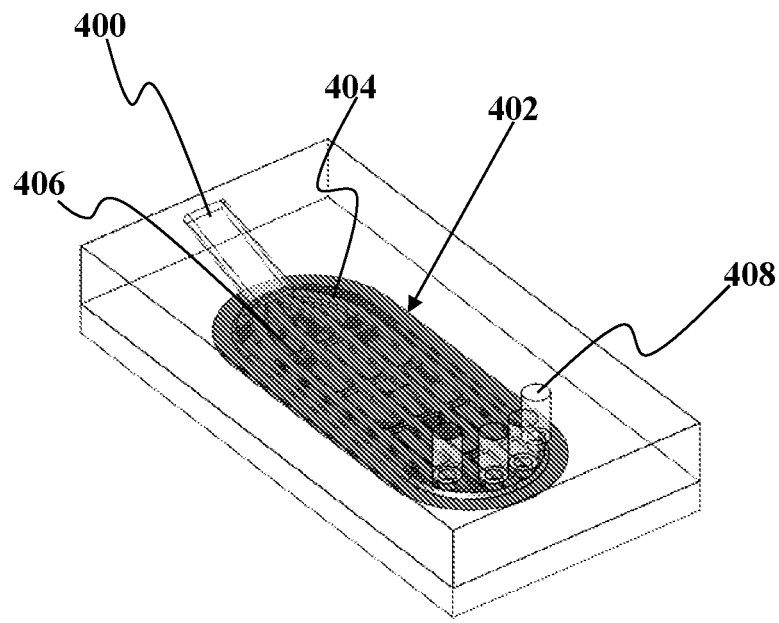
FIGS. 31-32 show various views of a device according to one embodiment described herein.
Figure 32:
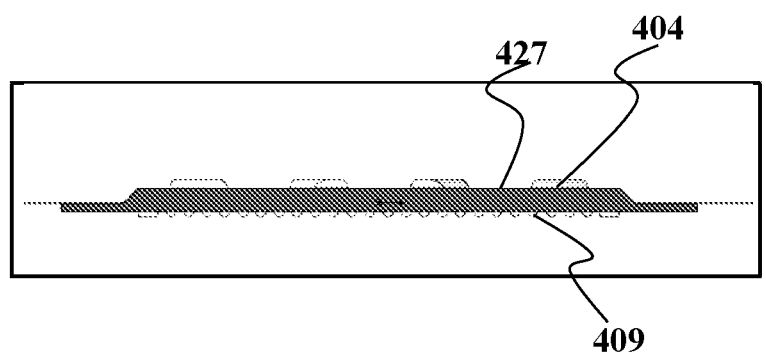

FIGS. 31 and 32 show at least one embodiment of an inlet channel 400 having a low aspect ratio in terms of channel height to width. The narrow height, wide inlet channel 400 leads to a multi-channel distributor 402, wherein the channels 404 also have low height to width aspect ratios and also have intersecting connectors 406 that provide connector pathways between the channels to form a grid or other pattern. In this particular embodiment, the connectors 406 are pathways with narrower cross-sectional areas that of the channels 404. Each of the channels 404 is coupled to its own vent 408, but it should be understood that embodiments where vents are shared are not excluded. The low aspect ratio of the channels 404 are more clearly shown in FIG. 32 along with their cross-sectional area relative to the cross-sectional area of the channels 409 of the collector.

Figure 33:
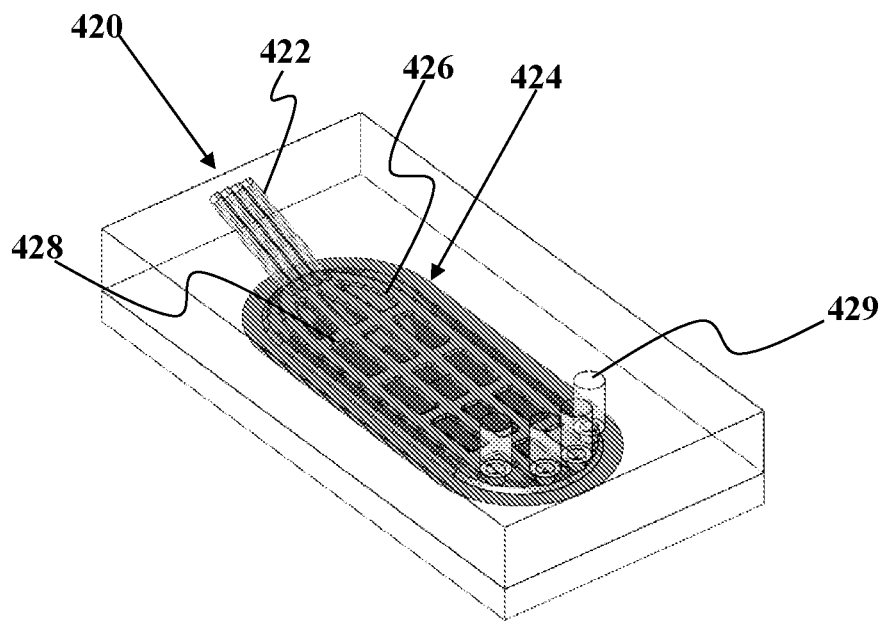
FIGS. 33-34 show various views of a device according to one embodiment described herein.
Figure 34:
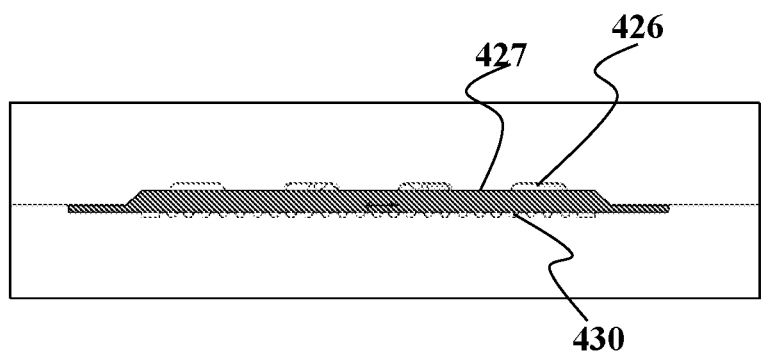

FIGS. 33 and 34 show an embodiment having an inlet 420 comprising a plurality of individual channels 422 that are co-located as the inlet 420. Once sample is collected, each of inlet channels 422 directs its portion of the sample to the distributor 424, which in this case is a multi-channel distributor, wherein the channels 426 have intersecting connectors 428 that provide connector pathways between the channels to form a grid or other pattern. In this particular embodiment, the connectors 428 are pathways with at least the same or greater cross-sectional area than that of the channels 426. Each of the channels 426 is coupled to its own vent 429, but it should be understood that embodiments where vents are shared are not excluded. The low aspect ratio of the channels 426 are more clearly shown in FIG. 34 along with their cross-sectional area relative to the cross-sectional area of the channels 430 of the collector. As seen in FIGS. 29-34, the separators are shown with its upper surface in contact at location 427 with a wall surface of the device so that there is no gap. Some embodiments may have the separator under compression to maintain this contact and to account for any variation due manufacturing tolerances. This contact may also be true for the surfaces below the separator. By way of non-limiting example, this vertical compression of the separator to overcome any manufacturing tolerances can be applied to any of the embodiments discussed or suggested herein.

Figure 35:
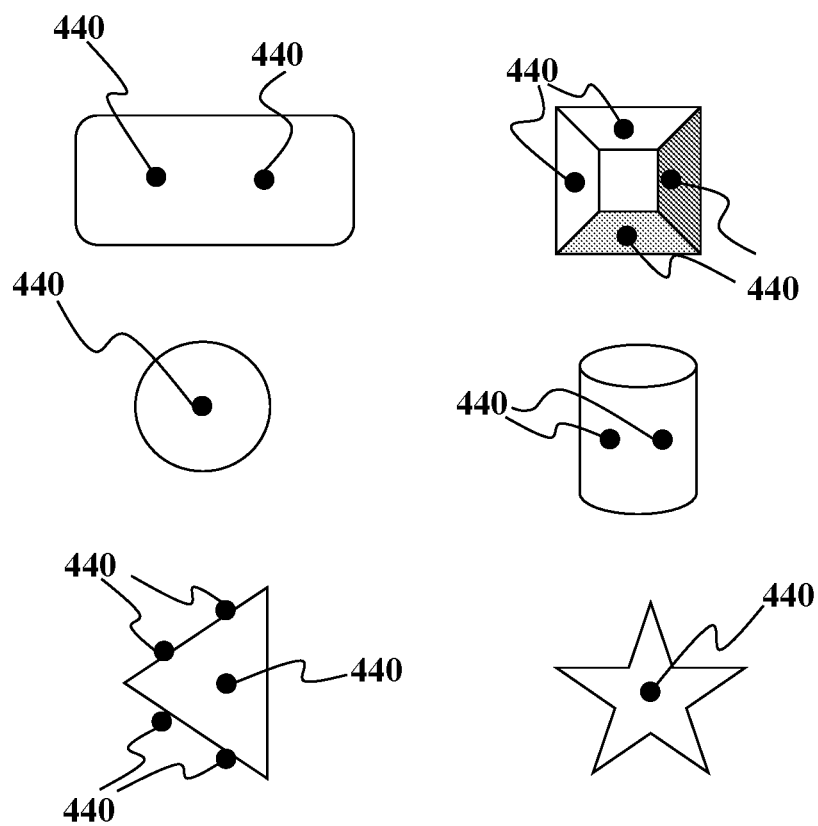
FIG. 35 shows various views of geometric configuration for the separator according to embodiments described herein.

Referring now to FIG. 35, it should be understood that the separator shown in the embodiments up to this point have been rectangular, race track, oval, or some combination of the foregoing. FIG. 35 shows that other shapes are not excluded and that the separator may be material shaped such as but not limited to elliptical, triangular, quadrilateral (e.g., square, rectangular, trapezoidal, parallelogram), pentagonal, hexagonal, heptagonal, octagonal, square, circular, star, other two dimensional patterns, or single or multiple combinations of the foregoing. It should also be understood that the separator may be configured to be in certain three dimensional configurations such as but not limited to tubular, cylindrical, disc, pyramid, mesa, or the like can also be adapted for use herein. By way of non-limiting example, some inlet locations 440 for sample distribution are shown for some embodiments. These are merely exemplary and other positioning of the number and location of inlets 440 are not excluded.

Sample Flow Over Separator

Figure 36:
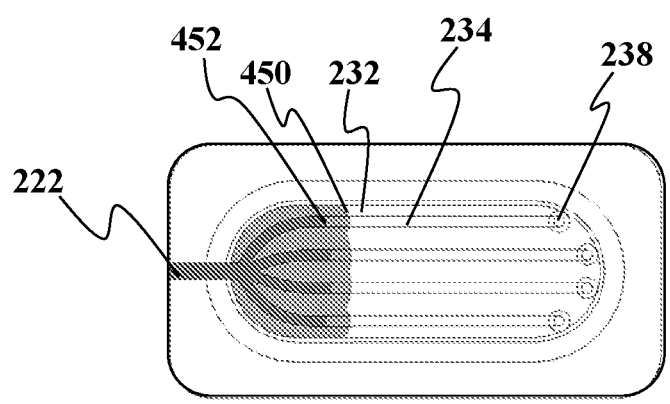
FIGS. 36-38 show one non-limiting example of sample inlet flow over the separator according to embodiments described herein.
Figure 37:
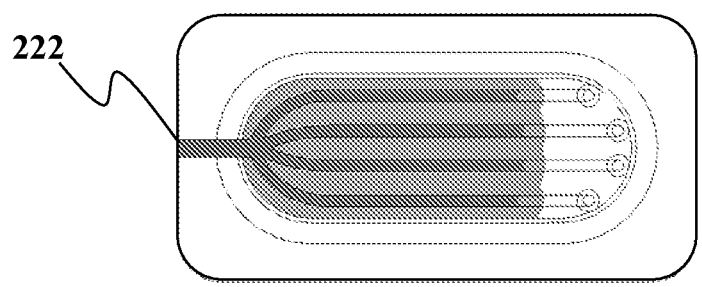
Figure 38:
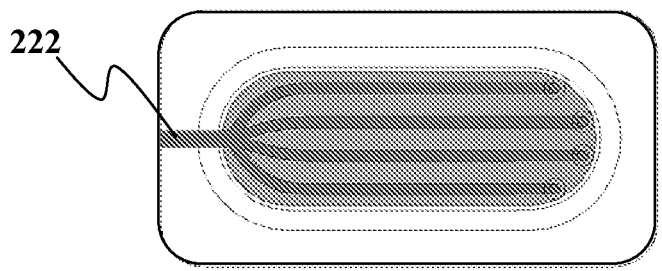

Referring now to the non-limiting examples of FIGS. 36 to 38, it should be understood that configuration wherein the channels 234 are open on one side to separator 232 allows for a multi-mode sample propagation pattern wherein at least a first portion is propagating laterally within the separator and a second portion is propagating through the channels 234 of the distributor over the separator 232. In this non-limiting example, the multi-mode sample propagation shows a leading edge 450 that is ahead of the sample in the channels at filled surface 452, which can exhibit a meniscus type shape as seen in FIG. 36. The sample continues to fill the separator 232 with the multi-mode sample propagation pattern as seen in FIG. 37 until the fill is completed as seen in FIG. 38, when sample is filled in the channels to reach the vents 238. In some embodiments, the volume of sample in the channels is greater than that in the separator 232 and this may account for part of the reason that the leading edge in the separator 232 may be moving ahead of that in the channels 234.

Sample Collection from Separator

Figure 39:
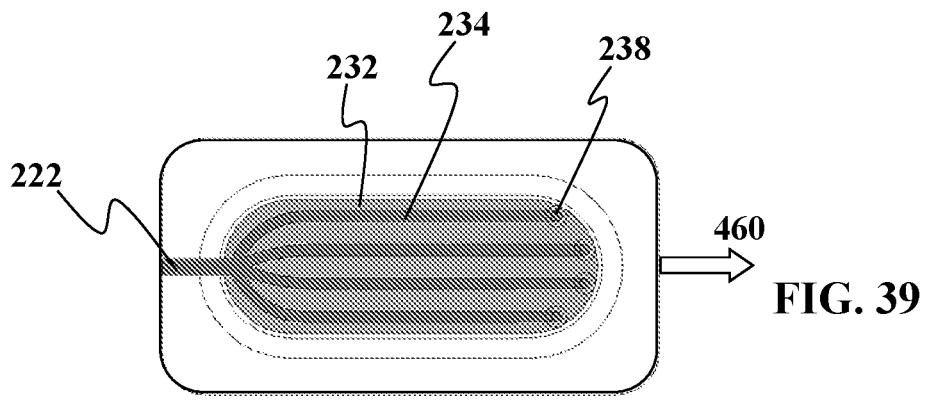
FIGS. 39-42 show one non-limiting example of sample outlet flow from the separator according to embodiments described herein.

Referring now to the non-limiting examples of FIGS. 39 to 42, at least one non-limiting example of sample flow during separation will now be described. Although not shown in the illustrations, at the point when the device is in the minimum fill condition as seen in FIG. 39, the sample is ready to be engaged by a force to draw sample more completely through the separator 232. In non-limiting example, there has already been some liquid sample that has traversed though the thickness of the separator 232 and has been pulled by capillary pressure from the capillary channels 240 of collector 242 to fill at least some of those channels and "prime" the channels with liquid that can then be used as part of the system to complete processing of the remaining sample held in the channels of the distributor above the separator 232. As indicated by arrow 460, a pulling force such as but not limited to full or partial vacuum in a sealed container like a vacutainer can be used to start moving liquid only sample into the container. As long as there is no "meniscus" break or if such breaks are recoverable, the sample still in the separator 232 or above it will begin to be drawn though the device.

Figure 40:
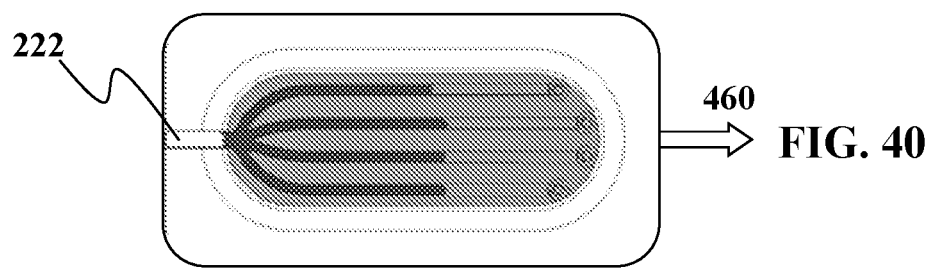
Figure 41:
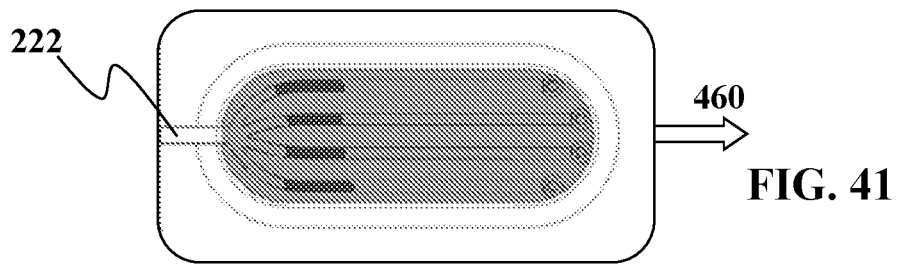
Figure 42:
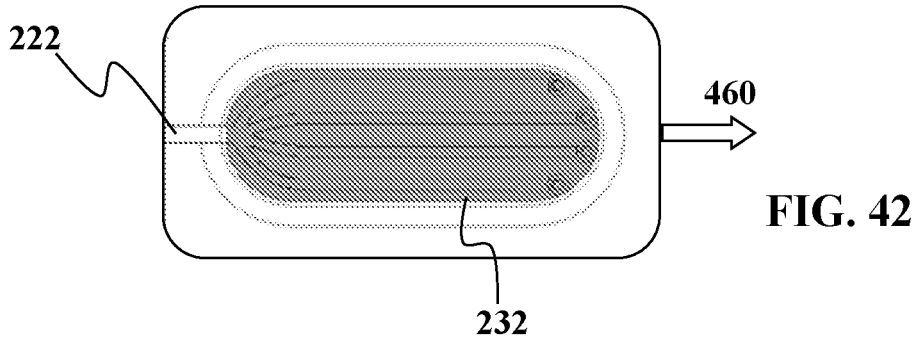

As seen in FIG. 40, the pull of liquid in the direction of arrow 460 on the underside of the separator 232 will also create a pull that draws sample laterally toward and/or downward into the separator 232. It is often desirable that this flow be without destructive trauma to formed components trapped in the separator 232, as the release of material from inside these formed components into the sample is generally undesirable. FIG. 40 shows that some sample that was in the inlet 222 has been drawn into the channels 234. Sample has begun to drain into the separator 232 in the channels 234 closest to the edge near the pulling force indicated by arrow 460. FIG. 41 also shows that the sample continues to be drawn downward and in the direction of arrow 460, there is also movement of sample further away from the inlet 222. FIG. 42 shows that upon completion of the separation process, form components such as but not limited to red blood cells that have been size-excluded from the sample remain and leave a light red color on the separator 232.

Figure 43:
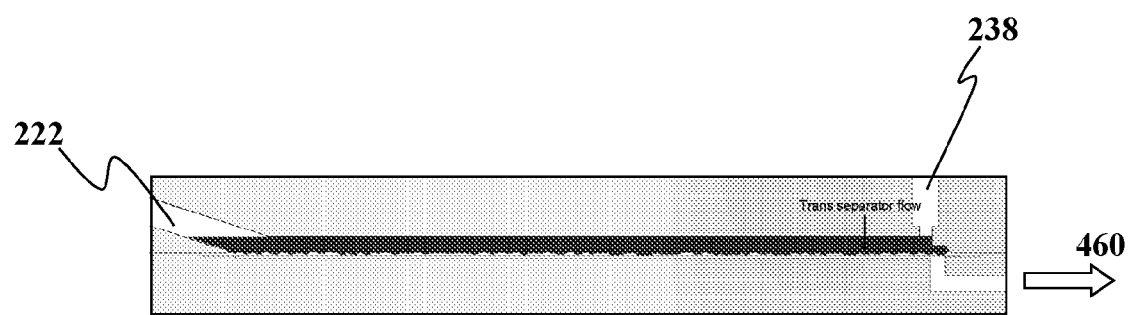
FIGS. 43-44 show side cross-sectional views of embodiments described herein.
Figure 44:
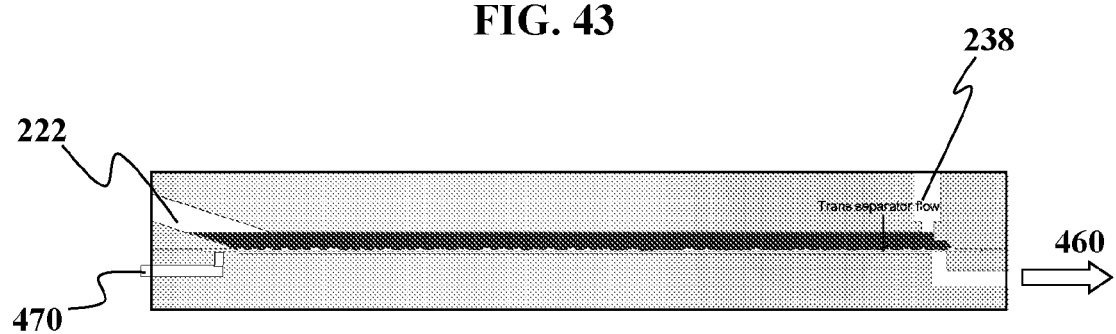

Referring now to FIGS. 43 and 44, a side cross-sectional view is shown of various embodiments of a sample collection and sample separation device. FIG. 43 shows that maximum trans separator pressure occurs closest to the end of the device where the outflow 460 is occurring. The further away from the area of outflow 460, the lesser the trans pressure across the separator. This gradient can explain in part the flow pattern seen in FIGS. 39-42.

As the separator beings to become clogged with formed components near the extraction end at arrow 460, flow has an increasing lengthwise component. Lengthwise intra separator flow increases shear stress on RBCs, and this trauma leads to greater hemolysis, even at lower pressures. Shorter, wider separator exhibit this effect in a manner that is less pronounced, while the effect is more pronounced in separators of greater lengths.

Referring now to FIG. 44, one embodiment herein comprises at least one or more vents 470 on the back side/collector side of the collector that decouples filtration from extraction. By providing a controlled inlet, the excessive force conditions that may cause excess shear stress it relieved by the controlled inlet from a pathway different from those occupied by the formed components, thus shifting pressure away from those components and still allowing for lateral liquid flow during extraction. In one non-limiting example, the controlled venting is balanced by having the pathway to reach the vent 470 pass through a portion of the separator 232. In one embodiment, this is a portion of the separator 232 is not filled with sample. Optionally, this is a compressed portion of the separator 232 not filled with sample. In this manner, there will be some level of venting that creates a pathway for air to enter by way of the vent to relieve the pressure put on formed components in the sample if there is no separate inlet. In one embodiment, the resistance is substantially equal to the resistance associated with venting through the separator 232 filled with sample. In one embodiment, the resistance is less than the resistance associated with venting through the separator 232 filled with sample. With the vent structure, one can extract plasma with reduced risk of hemolysis when dealing with blood samples.

Figures 45, 46:
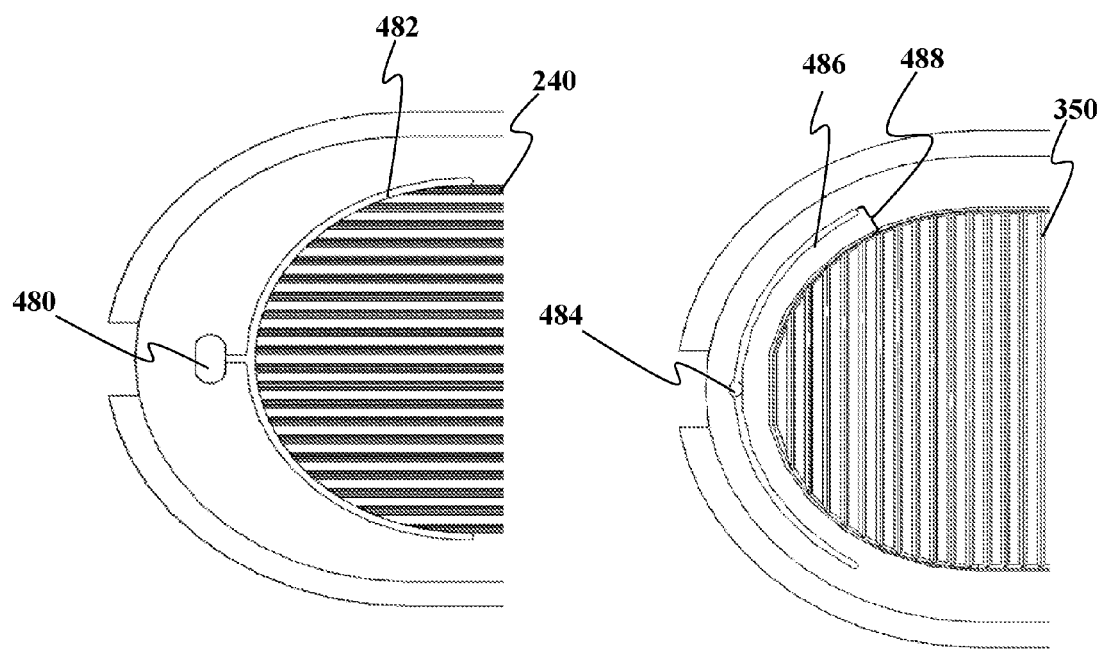
FIGS. 45-46 show top down plan views of vents according to embodiments described herein.

Referring now to non-limiting examples of FIGS. 45 and 46, top down views of vent structures in the lower half of the device is shown. FIG. 45 shows that in this embodiment, the vent 480 is coupled to a shaped pathway 482 that is configured to be in communication with the capillary channels 240 of the collector 242. Some embodiment may include a valve, porous material, mesh material, reduced diameter pathway, or other flow reducing material to control the flow of air from the vent to the interior of the collector 242. Some embodiments may also have the shaped pathway 482 be compressed with material from the separator (not shown) to slow the flow to the collector 242.

Referring now to FIG. 46, the vent 484 of this embodiment is coupled to a shaped pathway 486 that is configured to be in the area where the separator material will cover it. The coverage may be in a compressed manner. Optionally, the coverage may be without substantial compression. The communication with the capillary channels 350 of the collector are separated by a distance 488 from the shaped pathway 486 of the vent. In this manner, the pathway travels through at least that distance 488 of separator material before air from the vent is able to be in fluid communication with the channels 350.

It should be understood that although the shaped pathways 482 and 486 are shown as continuous pathways, they may optionally be a plurality of discontinuous, discrete openings linked to a common vent or having their own individual vents. In some embodiments, it is desirable to locate the vent near the end of the device distant from the end where liquid sample is being pulled from the device.

Referring now to non-limiting examples of FIGS. 47 and 48, these figures show cross-sectional views of the separator showing different percentages of saturation by the sample. As seen in FIG. 48A, the spacing of the channels of the distributor over the separator can be selected to increase separator saturation. FIG. 47A shows large channels spaced farther apart yields lower saturation that a combination of smaller channels spaced closer together to achieve a more uniform saturation pattern in the material.

As seen in the top down view in FIG. 47B, directed wetted area 490 as compared to indirectly wetted area 492 can be configured to increase overall saturation of the separator. The directly wetted surface area in FIG. 47B relative to total surface area is about 30%. Channel SA/V=DWA/V=5.0 for FIG. 47B.

FIG. 48B shows directed wetted area 492 as compared to indirectly wetted area 496 can be configured to increase overall saturation of the separator. The directly wetted surface area in FIG. 48B relative to total surface area is about 60%. Channels in the new configuration have a larger ratio of directly wetted surface area (DWA) to volume V, and nearly twice the directly wetted area as a fraction of total surface area (SA), wherein V is the volume of the separator. This results in a more effective wetting of the membrane; takes in more liquid per surface area. Channel SA/V=DWA/V=6.3 for FIG. 48B. In one embodiment, the desired range of channel surface area relative to the surface area of the separator on that side of the separator is in the range of about 35% to 70%. Optionally, the desired range of channel surface area relative to the surface area of the separator on that side of the separator is in the range of about 40% to 70%. Optionally, the desired range of channel surface area relative to the surface area of the separator on that side of the separator is in the range of about 50% to 60%. In one embodiment, the ratio of Channel SA/V which is also DWA/V is in the range of about 5 to 8. Optionally, the ratio of Channel SA/V which is also DWA/V is in the range of about 6 to 8. Optionally, the ratio of Channel SA/V which is also DWA/V is in the range of about 5.5 to 7. Optionally, the ratio of Channel SA/V which is also DWA/V is in the range of about 6 to 7.

Figure 49:
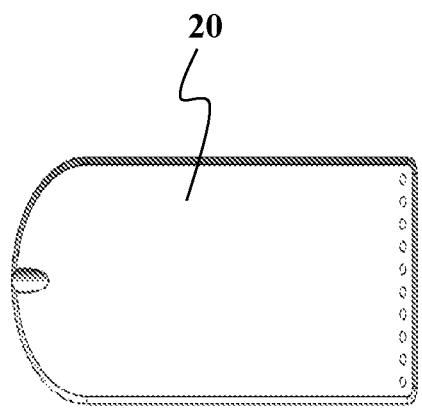
FIGS. 49-51 show top down plan views of various distribution channel patterns over the separator according to embodiments described herein.
Figure 50:
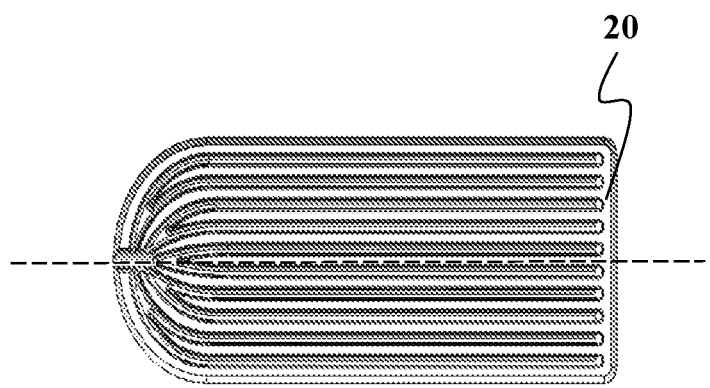
Figure 51:
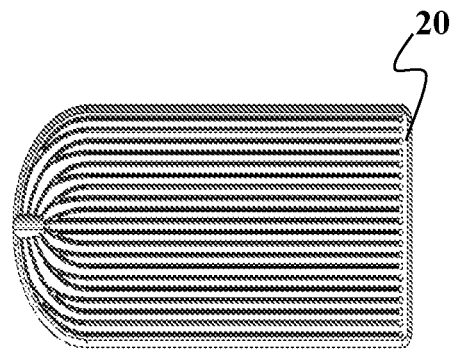

Referring now to non-limiting examples of FIGS. 49 to 51, various patterns of channels for distribution over the separator are shown. FIG. 49 shows an embodiment wherein there are no channels over the separator 20. FIG. 50 shows an embodiment with ten channels. Although distributed symmetrically about a longitudinal axis of the separator, it should be understood that other embodiments where channel size, distribution, or length are not symmetrical about the longitudinal axis may be used. FIG. 51 shows an embodiment with twenty two distribution channels.

Figure 52:
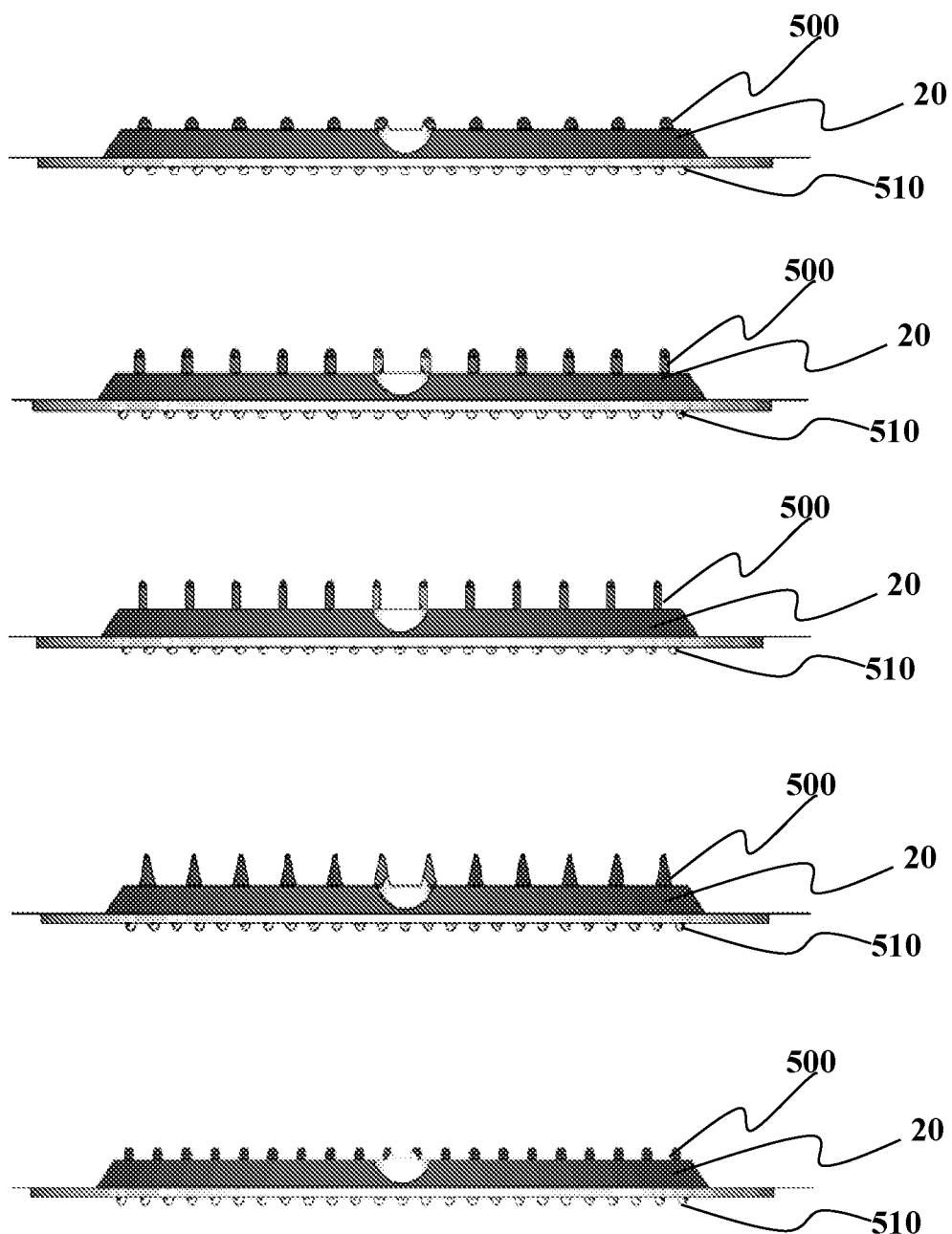
FIG. 52 shows cross-sectional views of various channel patterns and shapes over and under the separator according to embodiments described herein.

FIG. 52 shows a plurality of cross-sections of the device showing the distributor, separator, and collector. As seen, the channels 500 of the distributor can be of various cross-sectional shapes such as but not limited to elliptical, triangular, quadrilateral (e.g., square, rectangular, trapezoidal, parallelogram), pentagonal, hexagonal, heptagonal, octagonal, square, circular, star, other two dimensional patterns, oval, half-oval, half-circular, polygonal, or single or multiple combinations of the foregoing. The lengthwise pathway shape can also be configured such as to distribute sample in a desired manner over the separator. The channels 510 of the collector can be of various cross-sectional shapes such as but not limited to elliptical, triangular, quadrilateral (e.g., square, rectangular, trapezoidal, parallelogram), pentagonal, hexagonal, heptagonal, octagonal, square, circular, star, other two dimensional patterns, oval, half-oval, half-circular, polygonal, or single or multiple combinations of the foregoing. In one embodiment, the channels shapes of the distributor and the collector may be the same or different. Some embodiment of the distributor may have different shaped and/or sized channels in the distributor to provide a certain desired sample distribution pattern. Some embodiment of the collector may have different shaped and/or sized channels in the collector to provide a certain desired sample collection pattern.

Figure 53:
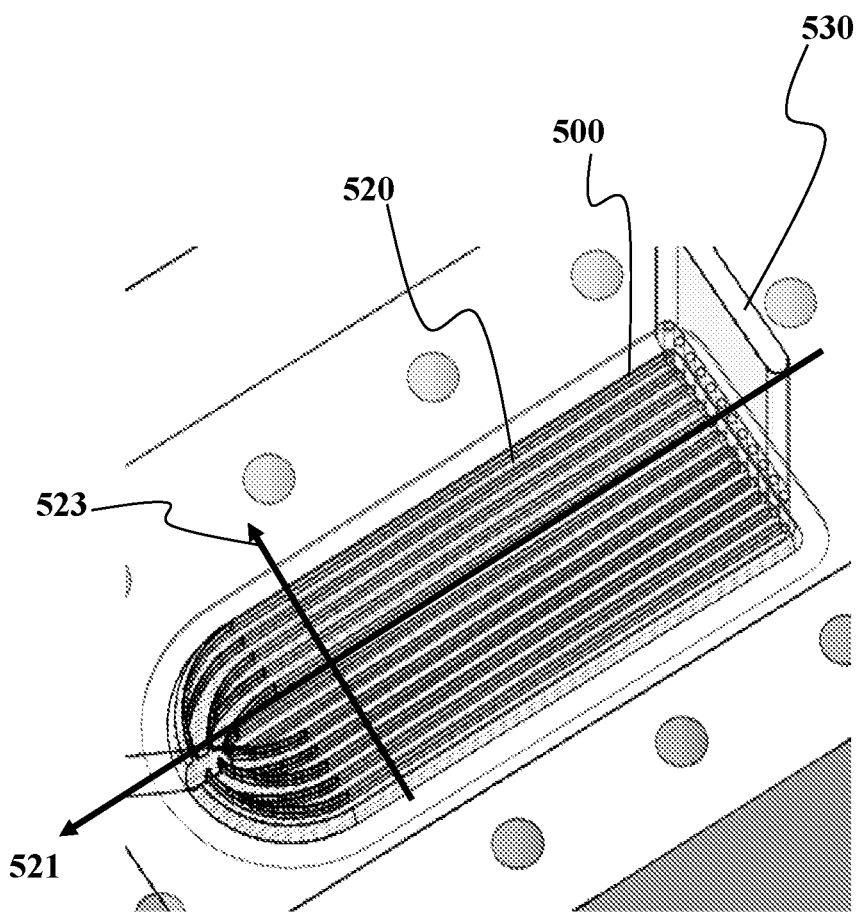
FIGS. 53-55 show non-limiting examples of various aspect ratios of the separator according to embodiments described herein.
Figure 54:
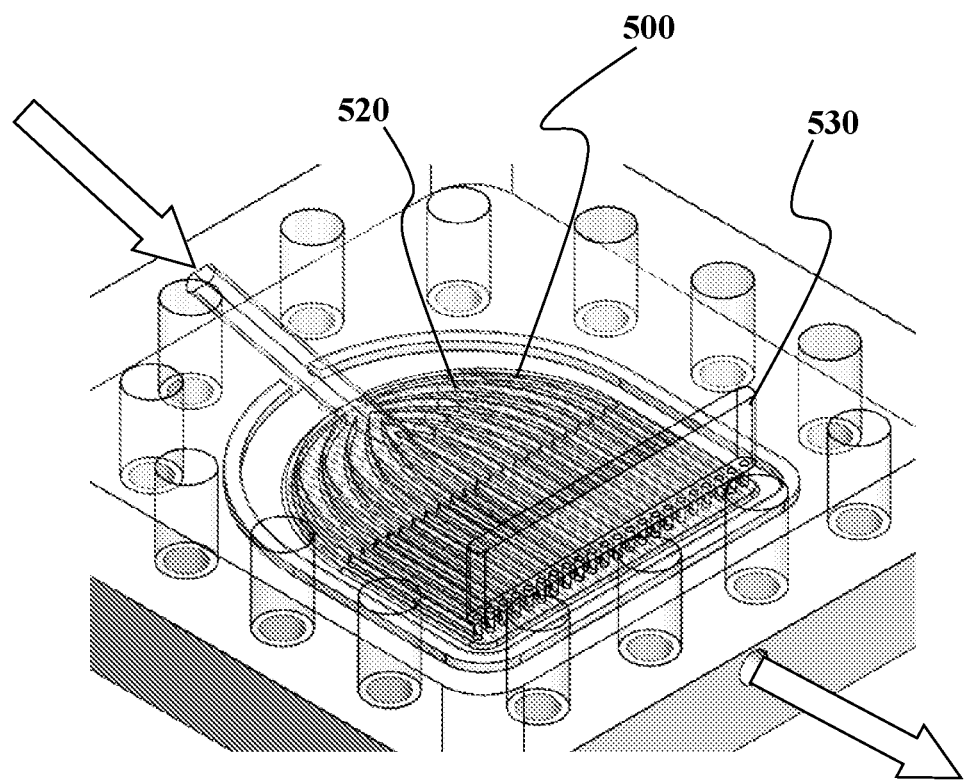
Figure 55:
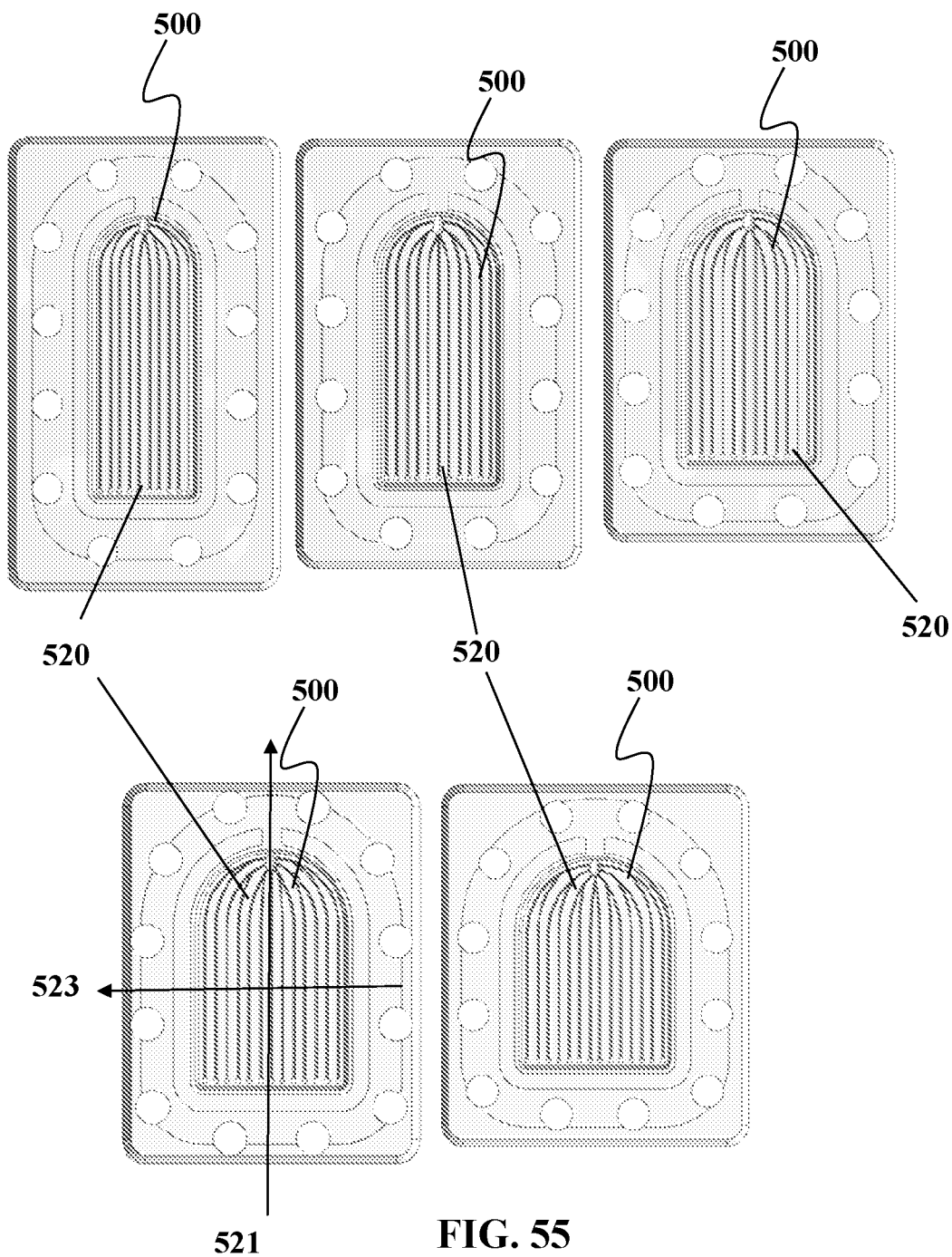

FIGS. 53 to 55 show various non-limiting examples of different aspect ratios for the separators for use with the device. FIGS. 53 and 55 also show different aspect ratios for the distributor used with such a device. In one embodiment, the separator has a configuration where the aspect ratios, defined as the length of the separator 520 (lengthwise along the direction of flow, toward the extraction port as indicated by arrow 521) divided by its width along arrow 523 are in the range of about 1:1 to 3:1. Optionally, the aspect ratio may be in the range of 1:1 to 5:1. Optionally, some embodiments may have aspect ratios in the range of 5:1 to 1:1. It should be understood that in these figures, the channels 500 are shown over the separator 520. A common vent 530 which is shown in FIGS. 53 and 54 can be also adapted for use with other embodiments described herein. FIG. 55 shows a plurality of different aspect ratios for the separator 520 and the distributor having channels 500.

Figure 56:
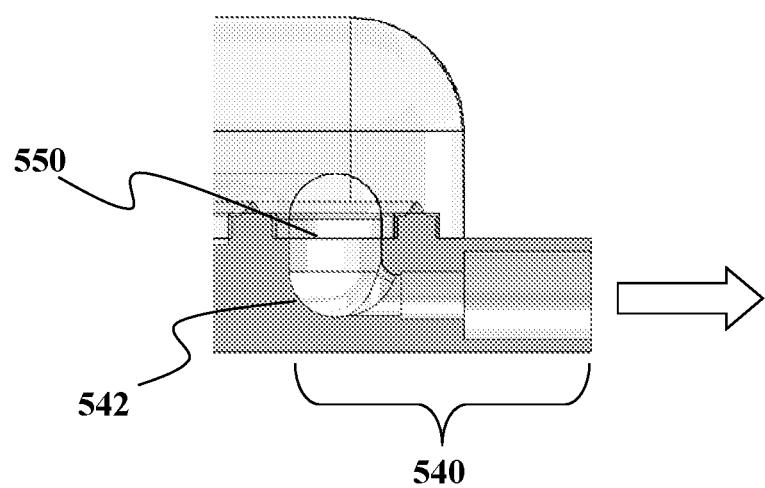
FIG. 56 shows a side cross-sectional view of one non-limiting example of an exit pathway according to embodiments described herein.

FIG. 56 shows one example of an exit conduit 540 below the collector 550 that shows a round inner surface 542 in the 90 degree elbow that transitions directions of sample flow out of the device from a vertical to a lateral flow.

Figure 57:
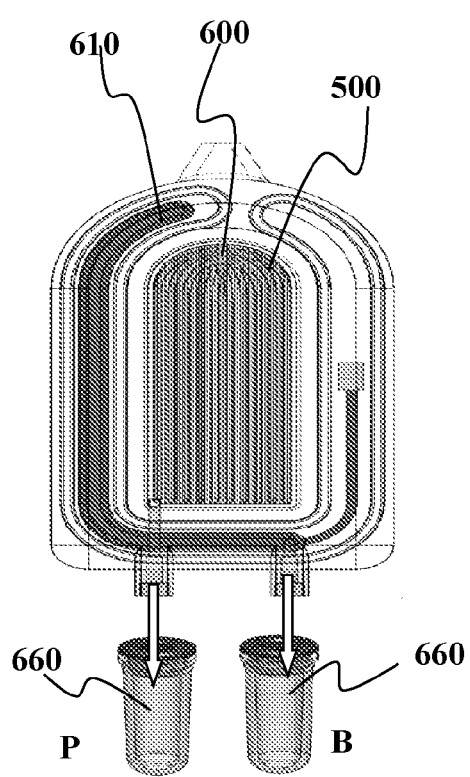
FIGS. 57 to 59 show views of non-limiting examples of devices having at least two sample pathways according to embodiments described herein.
Figure 58:
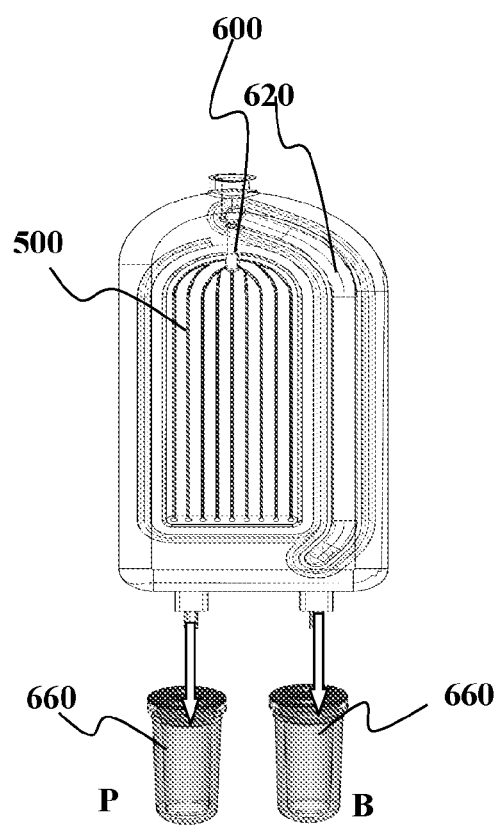
Figure 59:
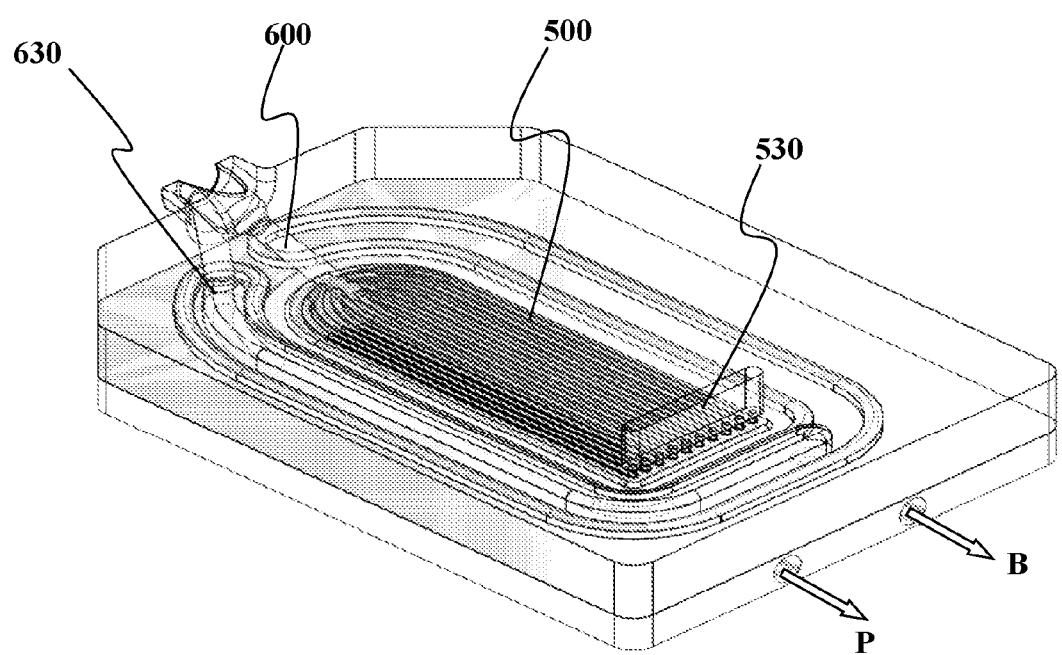

FIGS. 57 to 59 show that in addition to the pathway 600 for separation of formed components from the sample, some embodiments of the device are also configured to allow for other pathways 610, 620, or 630 that collect sample for treatment in a different manner. As seen in the figures, these pathways can be shaped and sized so that they can contain a desired amount of sample therein. Some embodiment may be configured so that the pathlength is such that the fill times for both the formed component separated sample and the un-separated sample are substantially the same. In this manner, a single indicator can be used to alert the user that sufficient fill has been achieved in both pathways.

FIGS. 57 to 59 also show that the output of the devices may be into containers 660. In one non-limiting example, the container may be but is not limited to a sealed container with piercable septum or cap, wherein the interior or the container is under full, partial, or some level of vacuum pressure therein to pull at least a certain volume of liquid sample into the container when it is fluidically engaged by the needle of the outlet tube or needle of the devices described herein. Optionally, the container may take the form of a test tube-like device in the nature of those marketed under the trademark "Vacutainer" by Becton-Dickinson Company of East Rutherford, N.J. The output of one device may be both blood (B) and plasma (P). Optionally, the output can be viewed as a) separated liquid-only sample and b) other sample output. Optionally, the output can be viewed as a) separated liquid-only sample (and any formed components smaller than the size exclusion limit) and b) other sample output. One or more of the pathways may be treated, coated, or otherwise prepared to deliver a material into the sample such as but not limited to an anti-coagulant, ethylenediaminetetraacetic acid (EDTA), citrate, heparin, or the like. Some may have two or more the pathways treated with the same or different material.

FIG. 59 shows a still further embodiment showing a Y-split to separate sample to go in to both pathways. It should be understood that although this indication of fill level in one or more of the pathways may be by way of a visual indication. It should also be understood that other indication methods such as but not limited to audio, vibratory, or other indication methods may be used in place of or in combination with the indication method. The indicator may be on at least one of the collection pathways. Optionally, indicators are on all of the collection pathways. It should be understood that the devices herein can be configured to have three or more pathways and are not limited to only two pathways.

For any of the embodiments herein, there can be container(s) such as but not limited to container 660 for use in drawing liquid sample that has gone through or will be drawn through the separator. In some embodiments, this is a two phase process, where there is an initial filling phase of sample into the separator using a first motive force and then a second phase using a second motive force to complete the sample separation process. The at least two different motive forces can be sensitive to timing in that it may be undesirable to activate the second motive force until a sufficient volume of sample has been metered into one or more of the pathways or until a sufficient fill allows for drawing of sample into the container without a meniscus break during the draw process under the second motive force. Suitable methods, devices, features, indicators, or the like can be found in U.S. Patent Application Ser. No. 61/786,351 filed Mar. 15, 2013, fully incorporated herein by reference for all purposes. Unified holders for multiple containers 660, shipping units, additional pieces for attaching/sliding/integrating the containers 660 and/or their holders to the sample collection/separation device, frits, and other adapter channels structures can also be found in U.S. Patent Application Ser. No. 61/786,351 filed Mar. 15, 2013.

Figure 60:
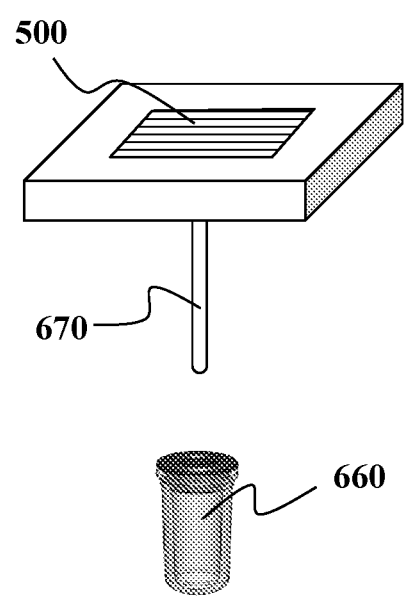
FIG. 60 shows yet another configuration of a device according to embodiments herein.

FIG. 60 shows a still further embodiment wherein the output tube, needle, channel, or other structure 670 can be oriented to exit from a bottom part of the device. It can be orthogonal to the plane or at other angles. Some embodiments may have both bottom and side exiting output structures 670. Some embodiments may have multiple output structures 670 in side and/or bottom surfaces.

In one embodiment, the collection and/or separation pathways such as but not limited to channels may also have a selected cross-sectional shape. Some embodiments of the pathways may have the same cross-sectional shape along the entire length of the pathway. Optionally, the cross-sectional shape may remain the same or may vary along the length. For example, some embodiments may have one shape at one location and a different shape at one or more different locations along the length of the pathways. Some embodiments may have one pathways with one cross-sectional shape and at least one other pathway of a different cross-sectional shape. By way of non-limiting example, some may have a circular, elliptical, triangular, quadrilateral (e.g., square, rectangular, trapezoidal), pentagonal, hexagonal, octagonal, or any other cross-sectional shape. The cross-sectional shape may be the same for the body, support, and base, or may vary. Some embodiments may select a shape to maximize volume of liquid that can be held in the pathways for a specific pathway width and/or height. Some may have one of the pathways with one cross-sectional shape while another pathway has a different cross-sectional shape. In one embodiment, the cross-sectional shape of the pathway can help maximize volume therein, but optionally, it can also optimize the capillary pulling forces on the blood. This will allow for maximized rate of filling. It should be understood that in some embodiments, the cross-sectional shape of the pathway can directly affect the capillary forces. By way of non-limiting example, a volume of sample can be contained in a shallow but wide pathway, or a rounded pathway, both containing the same volume, but one might be desirable over the other for filling speed, less possibility of air entrapment, or factors related the performance of the pathway.

Although the pathways may have any shape or size, some embodiments are configured such that the pathway exhibits a capillary action when in contact with sample fluid. In some instances, the pathway may have a cross-sectional area of less than or equal to about 10 $mm^2$, 7 $mm^2$, 5 $mm^2$, 4 $mm^2$, 3 $mm^2$, 2.5 $mm^2$, 2 $mm^2$, 1.5 $mm^2$, 1 $mm^2$, 0.8 $mm^2$, 0.5 $mm^2$, 0.3 $mm^2$, or 0.1 $mm^2$. The cross-sectional size may remain the same or may vary along the length. Some embodiments may tailor for greater force along a certain length and then less in a different length. The cross-sectional shape may remain the same or may vary along the length. Some pathways are straight in configuration. Some embodiments may have curved or other shaped path shapes alone or in combination with straight portions. Some may have different orientations within the device body. For example, when the device is held substantially horizontally, one or more pathways may slope downward, slope upward, or not slope at all as it carries fluid away from the initial collection point on the device.

In some embodiments the inner surface of the pathway and/or other surfaces along the fluid pathway such as but not limited to the sample inlet to the interior of a sample collection vessel may be coated with a surfactant and/or an anti-coagulant solution. The surfactant provides a wettable surface to the hydrophobic layers of the fluidic device and facilitate filling of the metering pathway with the liquid sample, e.g., blood. The anti-coagulant solution helps prevent the sample, e.g., blood, from clotting when provided to the fluidic device. Exemplary surfactants that can be used include without limitation, Tween, TWEEN®20, Thesit®, sodium deoxycholate, Triton, Triton®X-100, Pluronic and/ or other non-hemolytic detergents that provide the proper wetting characteristics of a surfactant. EDTA and heparin are non-limiting anti-coagulants that can be used. In one non-limiting example, the embodiment the solution comprises 2% Tween, 25 mg/mL EDTA in 50% Methanol/50% H20, which is then air dried. A methanol/water mixture provides a means of dissolving the EDTA and Tween, and also dries quickly from the surface of the plastic. The solution can be applied to the pathway or other surfaces along the fluid flow pathway by any technique that will ensure an even film over the surfaces to be coated, such as, e.g., pipetting, spraying, printing, or wicking.

It should also be understood for any of the embodiments herein that a coating in the pathway may extend along the entire path of the pathway. Optionally, the coating may cover a majority but not all of the pathway. Optionally, some embodiments may not cover the pathway in the areas nearest the entry opening to minimize the risk of cross-contamination, wherein coating material from one pathway migrates into nearby pathways by way of the pathways all being in contact with the target sample fluid at the same time and thus having a connecting fluid pathway.

Although embodiments herein are shown with two separate pathways in the sample collection device, it should be understood that some embodiments may use more than two separate pathways. Optionally, some embodiments may use less than two fully separate pathways. Some embodiments may only use one separate pathway. Optionally, some embodiments may use an inverted Y-pathway that starts initially as one pathway and then splits into two or more pathways. Any of these concepts may be adapted for use with other embodiments described herein.

Optionally, one or more of the pathways may be coated with a material to be incorporated into the sample. Optionally, it is desirable to fill the separator as quickly as possible relative to the other pathway in order to allow for maximum pre-filtration via the passive mechanisms described above. Thus, in one embodiment, one of the pathways fills first before the unfiltered/separated pathway fills. In one embodiment, the sample volume in one pathway is greater than the sample volume in the other pathway. In one embodiment, the sample volume in one pathway is greater by 1× than the sample volume in the other pathway.

Optionally, a cap (not shown for ease of illustration) may attach to the collection device using any technique known or later developed in the art. For instance, the cap may be snap fit, twist on, friction-fit, clamp on, have magnetic portions, tie in, utilize elastic portions, and/or may removably connect to the collection device body. The cap may form a fluid-tight seal with the collection device body. The cap may be formed from an opaque, transparent, or translucent material.

Optionally, the collection device body of the sample collection and separation device may be formed in whole or in part from an optically transmissive material. By way of non-limiting example, the collection device body may be formed from a transparent or translucent material such as but not limited to Poly(methyl methacrylate) (PMMA), Polyethylene terephthalate (PET), Polyethylene Terephtalate Glycol-modified (PETG or PET-G), or the like. Optionally, only select potions of the body are transparent or translucent to visualize the fluid collection channel(s). Optionally, the body comprises an opaque material but an opening and/or a window can be formed in the body to show fill levels therein. The collection device body may enable a user to view the channels within and/or passing through the device body. The channels may be formed of a transparent or translucent material that may permit a user to see whether sample has traveled through the channels. The channels may have substantially the same length. In some instances a support may be formed of an opaque material, a transparent material, or a translucent material. The support may or may not have the same optical characteristics of the collection device body. The support may be formed from a different material as the collection device body, or from the same material as the collection device body.

The collection device body may have any shape or size. In some examples, the collection device body may have a circular, elliptical, triangular, quadrilateral (e.g., square, rectangular, trapezoidal), pentagonal, hexagonal, octagonal, or any other cross-sectional shape. The cross-sectional shape may remain the same or may vary along the length of the collection device body. In some instances, the collection device body may have a cross-sectional area of less than or equal to about 10 cm$^2$, 7 cm$^2$, 5 cm$^2$, 4 cm$^2$, 3 cm$^2$, 2.5 cm$^2$, 2 cm$^2$, 1.5 cm$^2$, 1 cm$^2$, 0.8 cm$^2$, 0.5 cm$^2$, 0.3 cm$^2$, or 0.1 cm$^2$. The cross-sectional area may vary or may remain the same along the length of the collection device body 120. The collection device body may have a length of less than or equal to about 20 cm, 15 cm, 12 cm, 10 cm, 9 cm, 8 cm, 7 cm, 6 cm, 5 cm, 4 cm, 3 cm, 2 cm, 1 cm, 0.5 cm, or 0.1 cm. The collection device body may have a greater or lesser length than the cap, support or base, or an equal length to the cap, support, or base. There may be variations and alternatives to the embodiments described herein.

Figure 61:
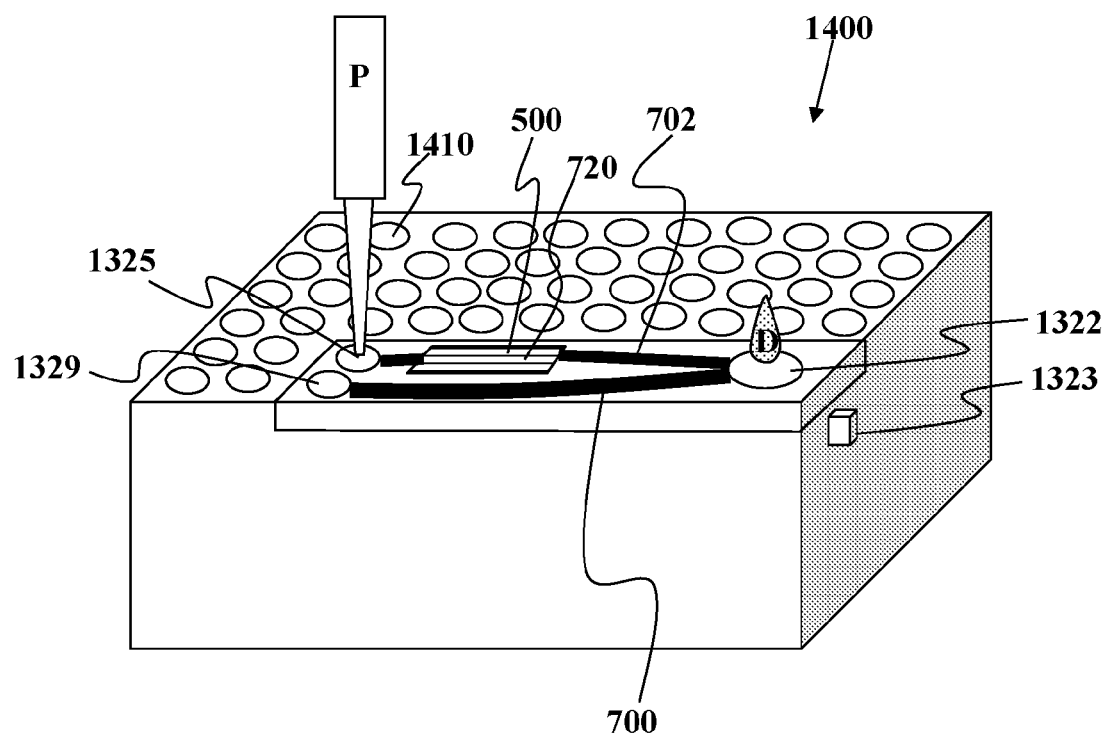
FIG. 61 shows one non-limiting example of a cartridge having a sample collector and sample separator according to embodiment herein.

Referring now to FIG. 61, a still further embodiment of a sample collection and sample separation device will now be described. This embodiment shows a cartridge 1400 with a sample collection and sample separation device 1402 integrated therein having one or two pathways 700 and 702. It should be understood that the device 1402 may be integrally formed with the cartridge. Optionally, it may be a separate unit that this is removable from the cartridge. Optionally, it may be a separate unit that this is added to the cartridge after sample has been collected from the subject. Optionally, it may be a separate unit that this is added and/or attached to the cartridge and sample is collected from the subject after the unit it added and/or attached to the cartridge.

In this non-limiting example, there is a collection location 1322 and one or more sample openings 1325 and 1329 where sample collection at location 1322 can then be accessed such as but not limited to handling by a pipette tip (not shown). The sample from droplet D will travel along pathway 1326 as indicated by arrow towards the openings 1325 and 1329, where the sample in the opening and any in the pathways 1324 and/or 1326 leading towards their respective openings 1325 and 1329 are drawn into a sample handling system such as but not limited to a pipette P. In some embodiments, particularly for the pathway 702 with separation member and the distributor channel 500, a vacuum or suction by the sample handling device can be used to fully draw sample though the separator 720 and complete the separation process. As indicated by arrows near the pipette P, the pipette P is movable in at least one axis to enable transport of sample fluid to the desired location(s). Although only a single pipette P is shown in FIG. 61 for ease of illustration, it should be understood that other embodiments may use a plurality of pipettes to engage one or more items associated with the cartridge. In this embodiment, the cartridge 1400 can have a plurality of holding containers 1410 for reagents, wash fluids, mixing area, incubation areas, or the like. Optionally, some embodiments of the cartridge 1400 may not include any holding containers or optionally, only one or two types of holding containers. Optionally, in some embodiments, the holding containers may be pipette tips. Optionally, in some embodiments, the holding containers are pipette tips that are treated to contain reagent(s) on the tip surface (typically the interior tip surface although other surfaces are not excluded). Optionally, some embodiments of the cartridge 1400 may include only the sample collection device 1402 without the tissue penetrating member or vice versa. A suitable device for use with cartridge can be found in U.S. patent application Ser. No. 13/769,798, filed Feb. 18, 2013. It should be understood that some embodiments may be configured to have only one of the above pathways in the sample collection and/or sample separation device. Some may have more than two of the pathways. Some may have more than one separator per pathway. Some may have multiple pathways each with one or more separators. Some embodiments may use the sample handling device such as but not limited to the pipette P to draw sample towards or onto the separator and then use the pipette to draw sample out of the underside or other side of the processor after the sample has been or has begun to be separated.

It should be understood that other cartridge configuration are not excluded. Some embodiments may directly incorporate the separator and/or distributor and/or collector into and integrated as part of the cartridge body.

Figure 62:
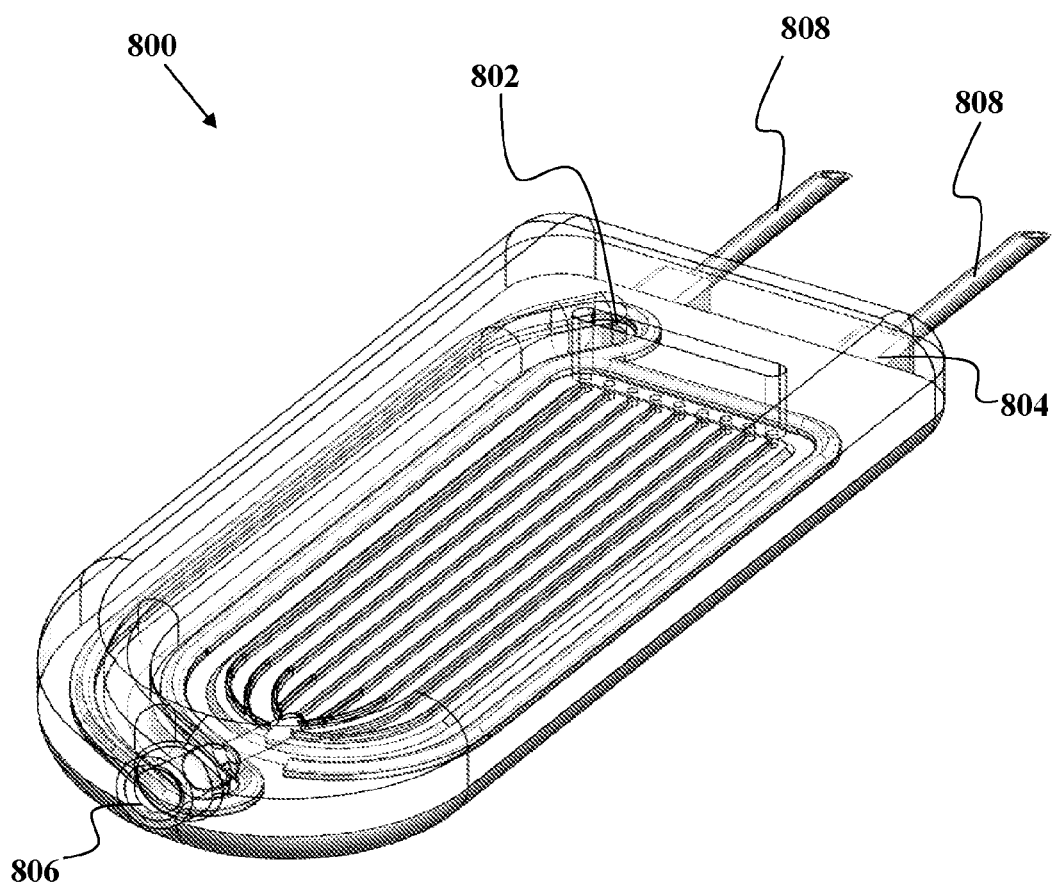
FIGS. 62 to 77 show still further embodiments as described herein.

Referring now to FIG. 62, a perspective view is shown of a still further embodiment showing a device such as a fluid circuit portion 800 with extraction ports 802 and 804. The embodiment of FIG. 62 uses a single inlet 806 to direct portions of the sample to two different pathways, wherein at least one portion passes through a formed component separation member.

Figure 63:
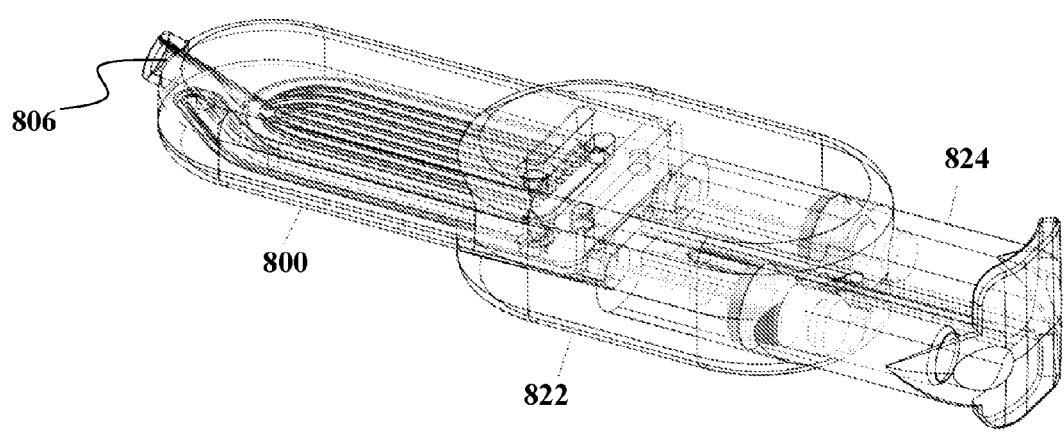

Referring now to FIG. 63, a perspective view is shown of a still further embodiment showing a device with fluidic circuit portion 800, a housing portion 822, and a sample container unit 824. As seen in FIG. 63, this non-limiting sample shows housing portion 822 coupling the fluidic circuit portion 800 with the sample container unit 824. The housing portion 822 allows for the sample container unit 824 to be coupled to the same fluidic circuit portion 800 but still have the sample container unit 824 movable between a first position (as shown in FIG. 63) and a second position.

In one embodiment, an inlet port centered along a midline of the fluidic circuit with an entry point on to the formed component separation member that is off-center relative to the midline of the formed component separation member.

In one embodiment, a vent channel of a curved configuration is coupled to a vent channel with a curved portion and an intersection linear (bent or straight) portion. The vents, in this non-limiting example are collection features that are on the side of the separation member were fluid, but not formed components, can exit the membrane.

Figure 64:
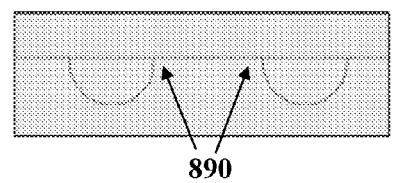
Figure 65:
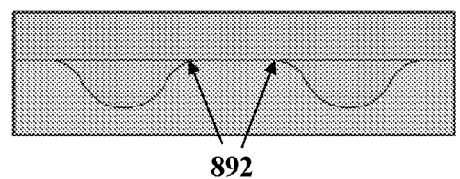
Figure 66:
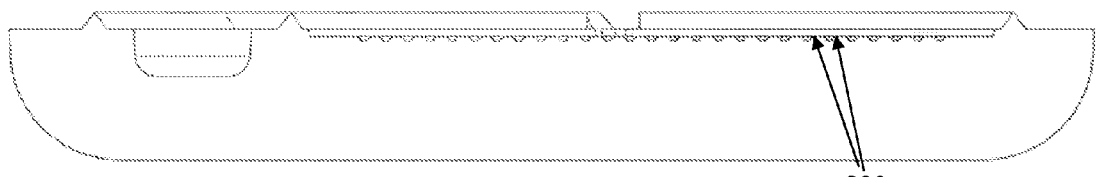

Referring now to FIGS. 64 to 67, various embodiments of the cross-sectional shapes of the capillary structure. FIG. 64 shows structures with sharp corners 890 while FIG. 65 shows an embodiment with radii or rounded corners 892.

Figure 67A:
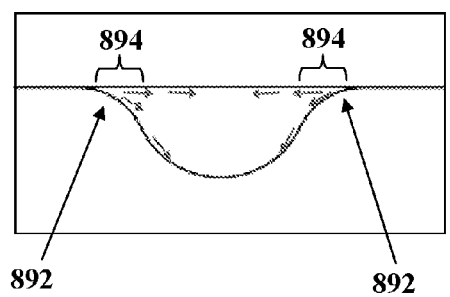
Figure 67B:
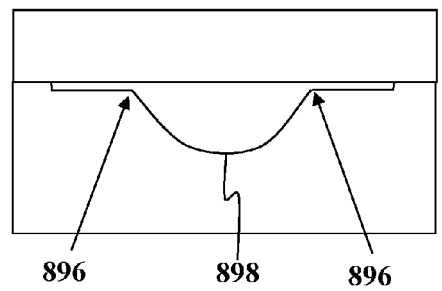

As more clearly seen in the non-limiting example of FIG. 67A, tangency and curvature of the rounded corners 892 may provide continuous liquid contact to assist with fluid flow out of a separation member such as but not limited to a membrane and into an opposing portion of the fluid circuit such as but not limited to the capillary flow structure. It should be understood that the round corners 892 creates at least one transition region 894 which can assist drawing or leaching of fluid from one region towards the fluid collection structures in the device. In some embodiments, this drawing or leaching of fluid out of the separation member can be desirable. By contrast, the embodiments with a sharp corner 890 which opens directly the capillary structure with a transition region diminishes the assistance that may come from have the closely spaced area associated with the tangency and curvature provided by rounded corners 892. Optionally as seen in FIG. 67B, some embodiments may have a sharp corner 896 but further include at least one transition region that may provide continuous liquid contact to assist with fluid flow out of the separation member. Optionally, some embodiments may have at least one increased width region between the capillary structure 898 and the transition region 894.

Optionally in one non-limiting example, the capillary structure may be formed of or have a surface treated to create a hydrophilic fluidic structure. In one non-limiting example, the structure can be made of a hydrophilic material such as but not limited Polyethylene terephthalate glycol-modified (PET-G) which has a small wetting angle and is a hydrophilic material which can draw fluid toward the back side of the membrane. Optionally, some embodiments may use cellulose acetate, cellulose acetate butyrate, or other suitable material.

Plasma collection vent: more plasma without hemolysis; distributors also are; capillary structures on the back side membrane. The other vent (blood side/distributor vents) is shown on the top side of the separation device that coupled to vent 915. Alternate plasma extraction methods are provided wherein different motive force, other than vacuum in a container, are used to draw fluid away from the separation membrane. In one embodiment, inlet flow control features may be used in the sample container to control the rate and/or amount of motive force applied to filtered sample and/or sample about to be filtered. It should be understood that hemolysis will corrupt the sample for many assays and is thus generally undesirable. Optionally, some embodiments may go without a dual channel inlet and use a single channel. Some embodiments may have an opening over the membrane, instead of at one end.

Optionally, this embodiment can have a passive, always open vent instead of a valve.

Optionally, some alternate extraction methods may include: providing a much higher extraction vacuum (crimp opening to meter pull forces, wherein the crimp results in a 5 to 10 micron wide opening in the tube, almost a cold weld when cutting so as to form a flow regulator). It should be understood that high vacuum in the container or from was another source was high enough to collect a desired liquid volume, but the initial spike from the high vacuum will cause excess pull on the form components that creates hemolysis when the sample is a blood sample. In one embodiment, there is at least 70% of theoretical fluid recovery. In one embodiment, there is at least 80% of theoretical fluid recovery. In one embodiment, there is at least 90% of theoretical fluid recovery.

For the final steps, the amount of friction can provide sufficient mechanical resistance from rapidly pushing sample vessel rapidly into the holder. The friction can be from the plunger, an external guide, and/or other component to provide a controlled movement between a first position and a second position. Other mechanical mechanism can be used to regulate speed that the user pushes it on. On the non-separator side, in one non-limiting example, there is no plunger. One embodiment may use deflected point needle that is anti-coring and also provides a side opening needle tip. In one-nonlimiting example, the anti-coring is desirable to prevent coring of the frit, which may introduce undesirable frit parts into the sample. The needle pierces through the frit. It should be understood that the frit is sized to cover or at least substantially cover the opening of the needle pointed tip opening.

In this non-limiting example, the plunger may have a harder portion in the center while a circumferential portion is softer for liquid seal performance.

Optionally, the capillary channels with fluid therein can also settle a bit before being engaged to be extracted. This delayed fill of the non-separator side ensures that the separator side has filled and had some settling time before being engaged to the sample collection unit for fluid transfer into the sample collection unit. In one embodiment, 80 microliters of whole blood results in 16 to 20 microliters of plasma.

Figure 68:
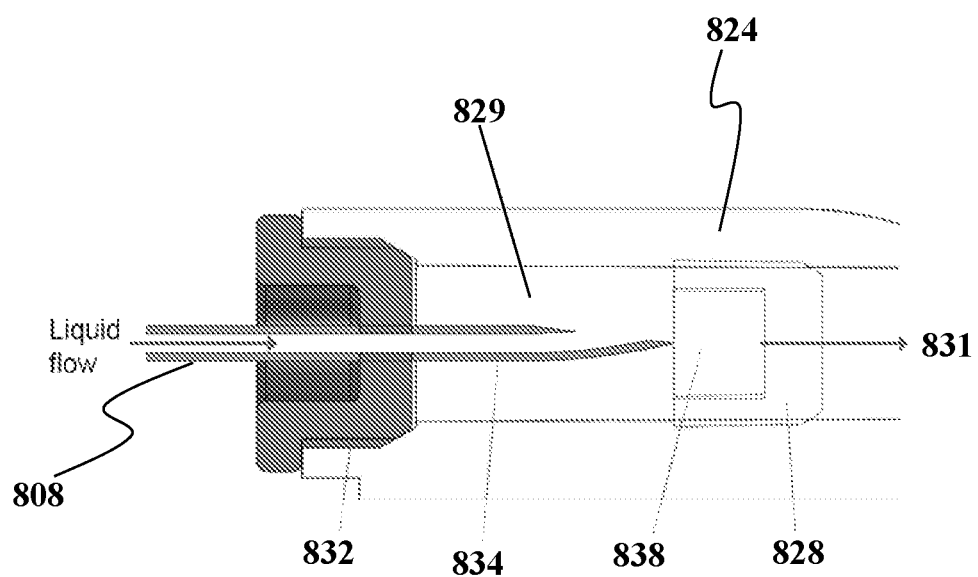

Referring now to FIG. 68, a cross-sectional view is shown of one non-limiting example wherein an inlet channel 808 is shown penetrating one non-limiting example of a sample container unit 824. As seen in FIG. 68, the movement of the plunger 828 of the sample container unit 824 can be used to create a motive force such as but not limited to at least a partial vacuum to draw liquid from the channel 808 into the sample container unit 824. In this non-limiting example, as the plunger is displaced as shown by arrow 831 in FIG. 68, this increases the interior volume 829 of the sample container unit 824 between the cap portion 832. It should be understood that, in one non-limiting example, there may be no sample in the sample container unit 824 until the motive force is provided to overcome any inherent capillary force of the channel 808 which brings the sample fluid into but not out a needle end 834 of the channel 808, In one non-limiting example, extracting fluid from the channel 808 may involve using one or more additional motive forces. It should be understood that this configured described herein may be similar to a reverse plunger. Optionally, some embodiments may use a conventional plunger, in place of or in combination with the structures herein, to provide motive force to draw sample into the sample container.

FIG. 68 also shows that, in at least one embodiment, the channel 808 may have a pointed distal end 834. Still further embodiments may have the channel 808 be of a non-coring design so as not to introduce any cored portion or debris of the cap 832 into the collected fluid. Regardless of whether a non-coring, conventional, or other shaped channel 808, it should be understood that some embodiments of plunger 828 may have a hardened core portion 838 that can withstand force input from the channel 808. As seen in FIG. 68, at least some embodiments will have a compliant material between the hardened core portion 838 and the side walls of the sample container so as to provide at least a sufficient fluid seal as the plunger 828 is moved from at least a first position to at least a second position.

Figure 69:
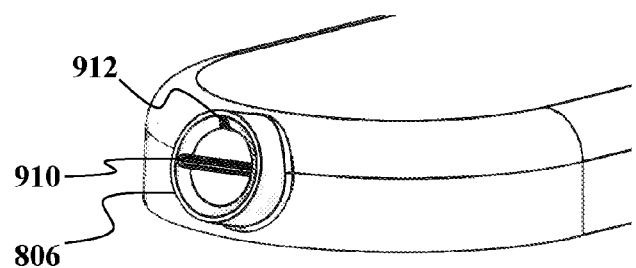
Figure 70:
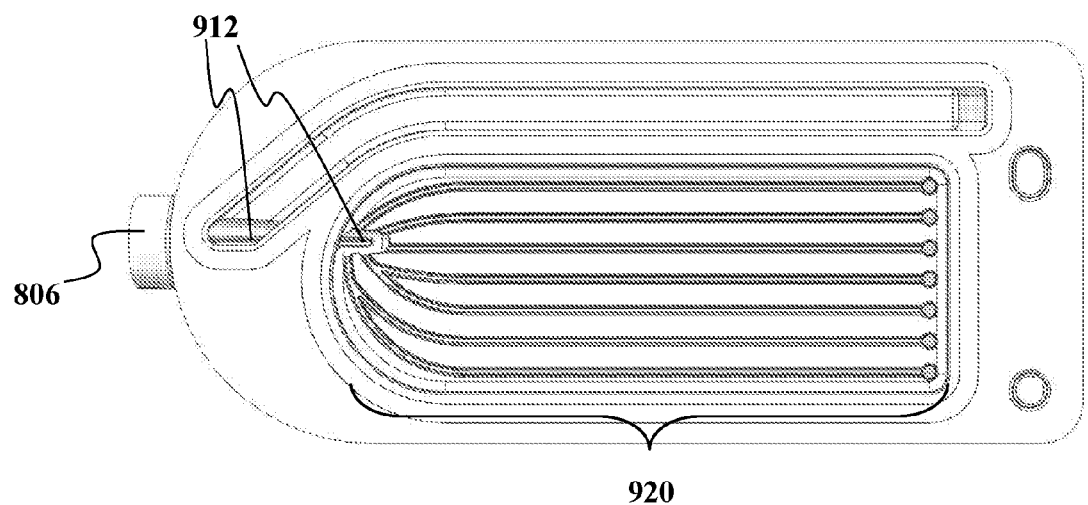
Figure 73:
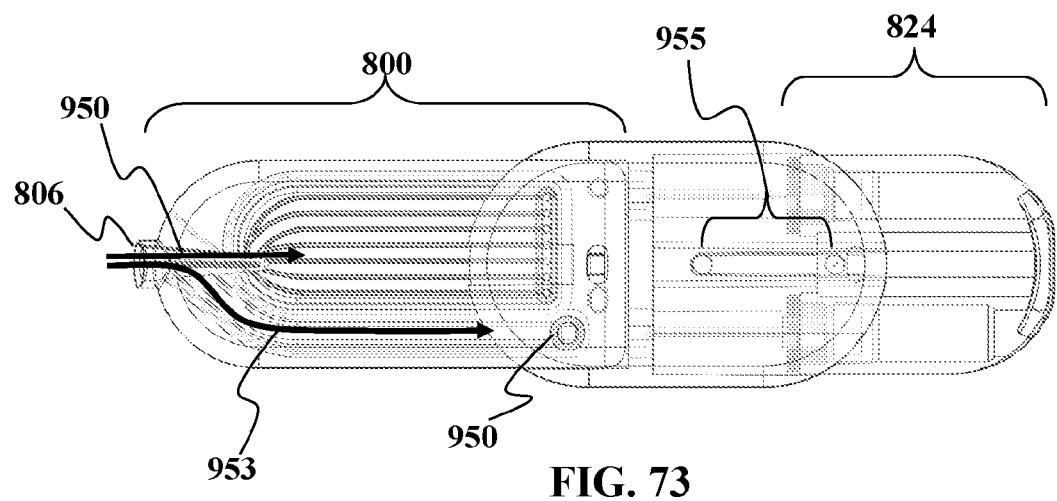

Referring now to the non-limiting examples of FIGS. 69 and 70, inlet design of inlet 806 may include flow guide structures 910 and 912 such as one or more small capillary channels in the sides of the inlet 806 encourage flow to enter pathway leading to the separation member, rather than the pathway without the separation member. As seen in FIG. 73, the flow guide structures 910 and 912 are located as positions along the inlet 806 that have surfaces that extend toward the separation component 920. In one non-limiting example, the fluid guide structures 910 and 912 are not along the bottom surface of the inlet, which may be where the other channel connects to the inlet. In one non-limiting example, the fluid guide structures 910 and 912 are not positioned along a surface of the inlet where the other channel connects to the inlet. Although FIG. 69 shows that the inlet 806 has at least two flow guide structures 910 and 912, it should be understood that some embodiments may only have a single flow guide structure. Optionally, some embodiments may have more than two flow guide structures. Optionally, some embodiments may have a single structure at the inlet 806 but forks into two or more structures as the fluid flows deeper into the inlet. Optionally, some embodiments may have a plurality of fluid guide structures wherein at least two of the structures merge together so that there are fewer guide structures as the fluid flow deeper into the structure. It should be understood that some embodiments may take a plurality of guide structures and merge them all into one guide structure.

Figure 71:
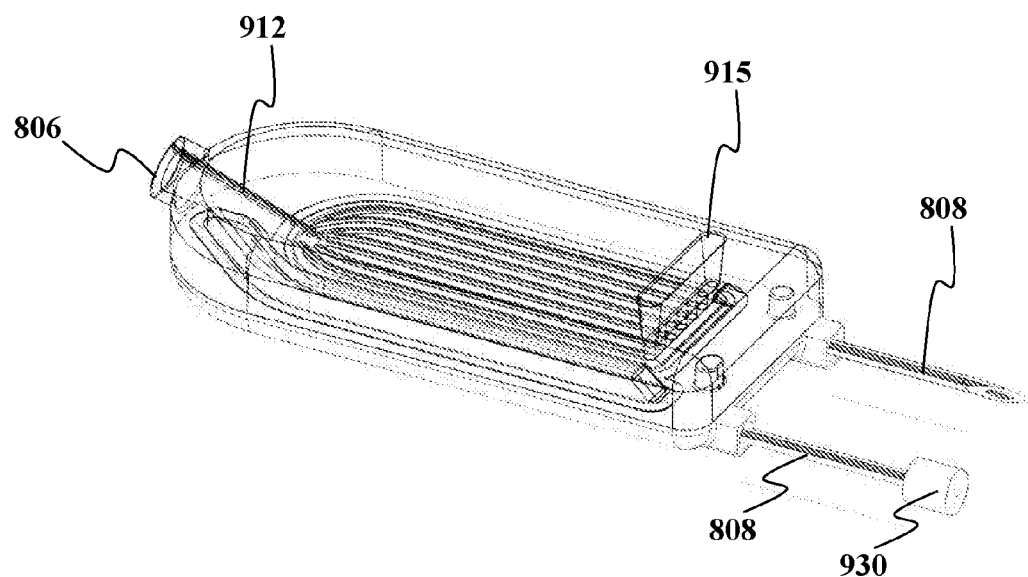

FIG. 71 shows a still further embodiment wherein at least one stop structure 930 such as but not limited to a frit is included on at least one of the extraction channels 808. In the non-limiting example of FIG. 71, the stop structure 930 is included on the channel 808 coupled to the non-separation member pathway, which may flow more freely and thus have a different flow resistance than the other pathway which passes through the separation member. Venting of the non-separation member pathway channel allows filling via capillary flow. In this embodiment, the channel 808 is vented through a pointed end of a needle, wherein an air porous frit such as but not limited to one of Porex or similar porous material, is coupled to a tip of needle, still allowing air through, but with more resistance. In this manner, filling on the non-separation member pathway side is slowed down so that separation member pathway can fill first. Other techniques for slowing flow along one pathway are not excluded and may be used alone or in combination with the stop structure 930 discussed herein. FIG. 71 also shows that in this embodiment, a combined vent 915 can be used to provide a vent path for the various vents associated with the sample distributor over the fluid entry surface of the separation member.

Furthermore, fill metering can be done using an indicator 950 (see FIG. 73) on the non-separation member pathway, because due to its lagging indicator quality due to a slower fill, if a fill level is reached on the non-separation member pathway, due to the slower, fill a user can safely conclude that the other pathway has already completed its fill process due to the slower fill in the non-separation member pathway. FIG. 73 also shows that there are at least two fluid flow paths within the device as indicated by arrows 951 and 953. FIG. 73 also shows that there may be guide 955, such as but not limited a guide member in a slot, that may act as a visual indicator that the movement of the sample collection unit 824 is complete and may optionally provide sufficient resistance to encourage a controlled rate of movement of the collection unit 824 so that the flow will be sufficient to minimize hemolysis of formed components in the sample.

Figure 72A:
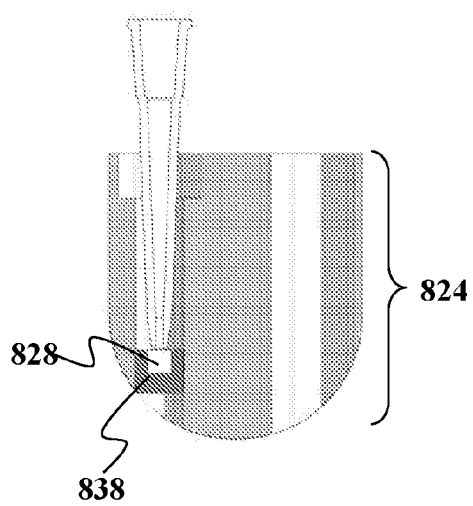

Referring now to FIG. 72A, it should also be understood that structures without a penetration tip, such a pipette tip, can also be adapted for use with certain embodiments of the sample container. FIG. 72A also shows that in at least some embodiments, the plunger 828 is only in one vessel and not in all of the vessels defined by the sample container unit. FIG. 72A may also be shown with the top plug 832 removed to allow for sample extraction using a pipette tip that is shaped to reach a bottom interior portion of the vessel being emptied.

Figure 72B:
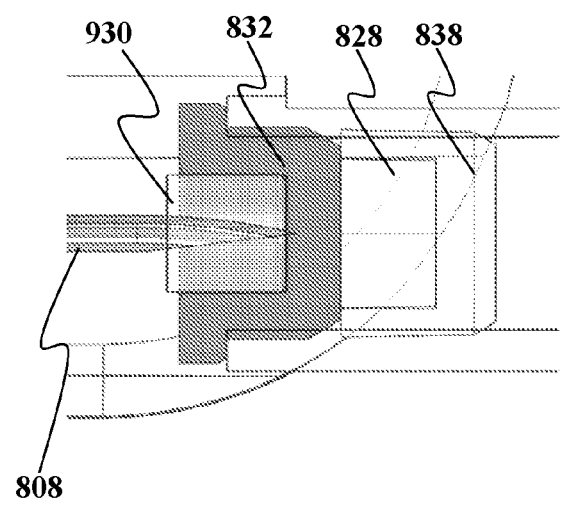

Referring now to the non-limiting example of FIG. 72B, the various initial positions are shown for a stop structure 930 on the channel 808 and that non-coring tip of the channel 808 has engaged a plug 832 of the container unit 824.

Figure 74:
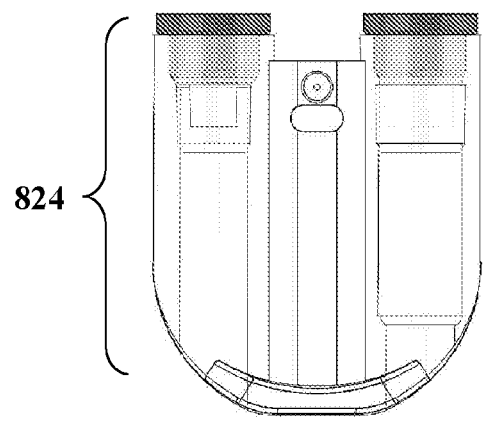

Referring now to FIG. 74, this non-limiting example shows a sample container unit 824 with one sample container sized larger to accommodate a pressure drop volume, that is the volume to which air on the plasma side of the formed member separation membrane (including inside the sample container unit) expands due to the pressure drop across the membrane.

Figure 75:
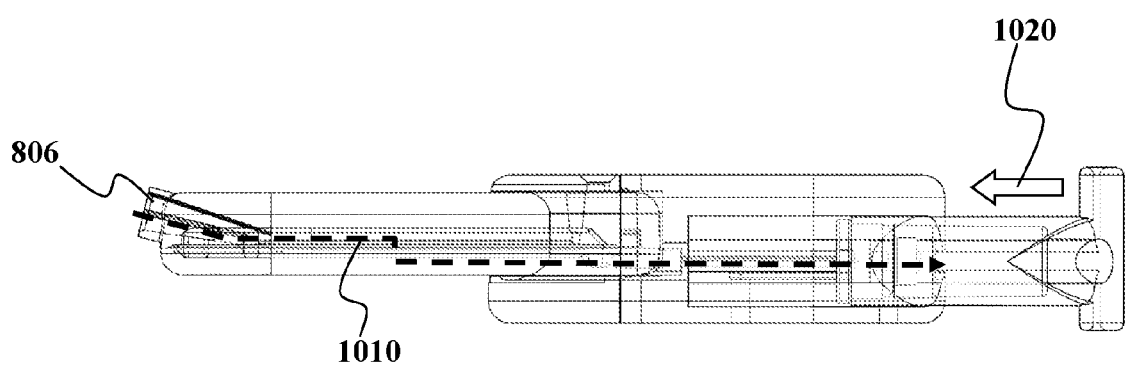

FIG. 75 shows a side view of the device wherein the sample flow pathway indicated by arrow 1010 shows that sample enters at an angle, flows along one plane, downward to a different plane and is drawn laterally out at the lower plane. Movement of the sample collection unit 824 is indicated by arrow 1020, wherein in this embodiment, movement of the sample collection unit 824 provides motive force to draw sample substantially free of formed components into the sample collection unit. Although many of the embodiments shown herein use linear movement of the sample collection unit 824, it should be understood that embodiments using rotary motion to provide the motive force or rotary motion translated into linear motion to provide the desired movement to draw sample into the sample container.

Some embodiments of the collection unit may have a cross-sectional shape with an asymmetry, a protrusion, or other feature that serves as a keying feature for orienting the SCU in any receiving device or structure.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, with any of the above embodiments, it should be understood that some embodiments may handle other types of samples and necessarily biological samples. Although many illustrations are shown with only a single inlet port, it should be understood that some embodiments may have at least two inlet ports. In some embodiments, both inlet ports are on the same end of the device. Optionally, some embodiments may have inlet ports on the same surface of the device. Optionally, at least the two inlets are adjacent to each other. Optionally, there are at least three inlet ports. Optionally, at least two inlet ports are each defined by at least one capillary tube. In this embodiment where each inlet has its own capillary tube, at least one tube directs fluid to a non-separation pathway while a second tube directs fluid to a separation pathway. Optionally, some embodiments may combine inlets formed by capillary tubes with inlet(s) associated with a non-capillary pathway. Some embodiments may have the inlet along a centerline axis of the device. Optionally, some embodiments may have the inlet aligned off the centerline. Optionally, some embodiments may orient the inlet to be along or parallel to the axis of the centerline of the device. Optionally, some embodiments may orient the inlet along an axis that is at an angle to the plane of the device. Optionally, instead of having the inlet at one end of the separation device, it should be understood that some embodiments may have the inlet directly over at least one portion of the separation device. In this manner, the opening may direct fluid onto the membrane with a minimal amount of travel in a lateral tube or pathway.

Figure 76:
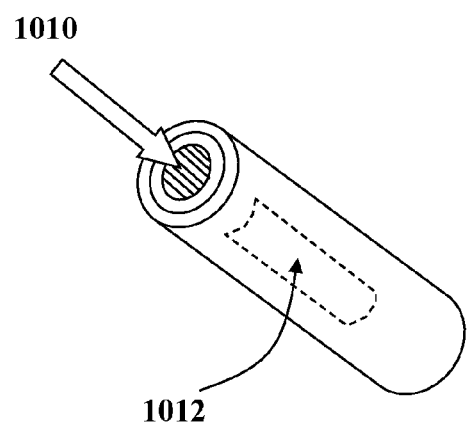

Optionally, some embodiments may be configured with a co-axial design such as shown in FIG. 76. One embodiment may have sample enter along an inner lumen for an inside-out type filtration as indicated by arrow 1010. Optionally, some embodiments may use an outside-in type filtration if the separation membrane is located in the inner lumen and sample fluid enters from a surface opening (shown in phantom) as indicated by arrow 1012 or from an inlet on one end of the device.

Figure 77:
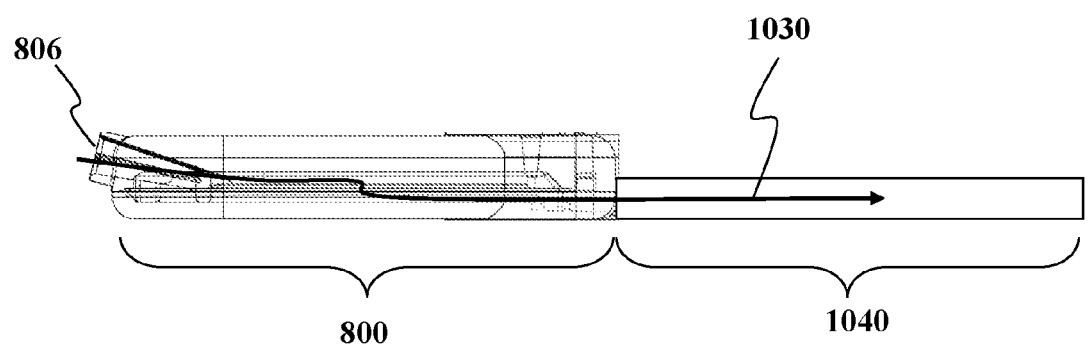

Optionally as seen in FIG. 77, some embodiments may have a portion 800 such as the fluid circuit portion that includes the separation member fluidly coupled to a second portion 1040. Optionally, it may be configured not to include the non-separation pathway. Optionally, it may be configured to include the non-separation pathway. Some embodiments may have this combination of portion 800 with portion 1040 in a test strip configuration. Some embodiments may have this combination of portion 800 with portion 1040 in a lateral flow device configuration. Some embodiments may have a unibody structure or other merged structure that is formed to provide support to both portions 800 and 1040. Motive force can be provided to move the sample as indicated by arrow 1030 which flow out or the fluid circuit of portion 800 and that the fluid portion of the sample, substantially free of the formed components, can enter a second region 1040 which may be but is not limited to an analytical region. In some embodiments, the second region 1040 also provides a motive force such as but not limited to wicking force associated with such material in at least a portion of the second region 1040.

Optionally, it should be understood that some embodiments may have at least one formed component separation pathway for use in a non-diagnostic device. By way of non-limiting example, the device may be for sample collection, where no diagnosis occur on the device. Optionally, it should be understood that some embodiments may have at least one formed component separation pathway and at least one non-separation pathway for use in a non-diagnostic device. Optionally, it should be understood that some embodiments may have at least two formed component separation pathway and at least one non-separation pathway for use in a non-diagnostic device. Optionally, it should be understood that some embodiments may have at least one formed component separation pathway and at least two non-separation pathways, all for use in a non-diagnostic device. Of course, some alternative embodiments may have one or more pathways for use for diagnosis. Optionally, some embodiments may use this type of separation device with lateral flow strip wherein the fluid, after formed component separation, may be moved such as but not limited to wicking or other capillary flow onto a second region such as but not limited to an analyte-detecting region on a device such as but not limited to a test strip for analysis.

Optionally, some embodiments may provide a vibration motion source, such as but not limited to one built into the device and/or in an external device use to process the sample container, to assist in fluid flow within device, during the collection, or post-collection. Some embodiments may use this vibration to assist flow or to remove any air pockets that may be created, such as but not limited to when doing a top-down fill. Optionally, some embodiments may provide more periodic or pulse type force to assist in fluid flow.

It should be understood that although many components herein are shown to be in alignment in the same plane or parallel planes, some embodiments may be configured to have one or more component in a plane angled to or orthogonal to a plane of the fluid collection circuit in portion 800. The fluid collection circuit in portion 800 does not need to be a flat planar device and may be in a curved configuration. Optionally, some embodiments may have it a cone configuration. Optionally, some embodiments may have it device with a polygonal cross-sectional shape. As seen, the fluid collection circuit in portion 800 is not limited to a planar shape.

It should also be understood that in many embodiments, the portion 800 may be made of a transparent material. Optionally, the portion 800 may be made of a translucent material. Optionally, portions of the portion 800 may be covered with paint or other opaque material, be formed of an opaque material, or the like such that only portions that may contain fluid are transparent or translucent so as to provide an indicator of fill level. Such an embodiment may have all or only a portion of the fluidpath visible to the user. In one non-limiting example, bar codes, color-coding, visual information, instructions, instructions for use, fill-indicator, advertising, child-appealing aesthetics, texturing, texturing for grip purpose, texturing for contour, texturing to provide feedback such as orientation of the front of the device, or other coating may be used hereon.

Optionally, some embodiments may include an intermediary structure between the fluid circuit in portion 800 and the sample collection unit 824. This intermediary structure can be in the fluid pathway and provide certain function such as but not limited to introducing a material into the collected fluid such as but not limited to anti-coagulant. Optionally, the intermediary structure in the fluid path may provide another route, such as switch or connection pathway, to add additional sample or other liquid material into the collected fluid.

Optionally, some embodiments may have disposable portion(s) and reusable portions, wherein the reusable portions can be mated with the disposable portion(s) to form another collection device. By way of non-limiting example, a reusable portion may be one that does not directly contact the sample fluid or filtered fluid.

Although embodiments herein show the separation member as part of a handheld device, it should be understood that other embodiments may incorporate the device as part of a non-handheld benchtop device, a non-portable device, or the like and the disclosures herein are not limited to handheld or disposable units. Some embodiments may also include features for collection sample from a plurality of sample processing devices. In this manner, an increased amount of filtered sample can be collected, simply by using more devices for use with more samples which in one embodiment may all be from one subject. Optionally, samples in multiple devices may be from multiple subjects.

As used herein, the terms "substantial" means more than a minimal or insignificant amount; and "substantially" means more than a minimally or insignificantly. Thus, for example, the phrase "substantially different", as used herein, denotes a sufficiently high degree of difference between two numeric values such that one of skill in the art would consider the difference between the two values to be of statistical significance within the context of the characteristic measured by said values. Thus, the difference between two values that are substantially different from each other is typically greater than about 10%, and may be greater than about 20%, preferably greater than about 30%, preferably greater than about 40%, preferably greater than about 50% as a function of the reference value or comparator value.

As used herein, a "surfactant" is a compound effective to reduce the surface tension of a liquid, such as water. A surfactant is typically an amphiphilic compound, possessing both hydrophilic and hydrophobic properties, and may be effective to aid in the solubilization of other compounds. A surfactant may be, e.g., a hydrophilic surfactant, a lipophilic surfactant, or other compound, or mixtures thereof. Some surfactants comprise salts of long-chain aliphatic bases or acids, or hydrophilic moieties such as sugars. Surfactants include anionic, cationic, zwitterionic, and non-ionic compounds (where the term "non-ionic" refers to a molecule that does not ionize in solution, i.e., is "ionically" inert). For example, surfactants useful in the reagents, assays, methods, kits, and for use in the devices and systems disclosed herein include, for example, Tergitol™ nonionic surfactants and Dowfax™ anionic surfactants (Dow Chemical Company, Midland, Mich. 48642); polysorbates (polyoxyethylenesorbitans), e.g., polysorbate 20, polysorbate 80, e.g., sold as TWEEN® surfactants (ICI Americas, New Jersey, 08807); poloxamers (e.g., ethylene oxide/propylene oxide block copolymers) such as Pluronics® compounds (BASF, Florham Park, N.J); polyethylene glycols and derivatives thereof, including Triton™ surfactants (e.g., Triton™ X-100; Dow Chemical Company, Midland, Mich. 48642) and other polyethylene glycols, including PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, sucrose monostearate, sucrose monolaurate, sucrose monopalmitate, PEG 10-100 nonyl phenol series, PEG 15-100 octyl phenol series, and poloxamers; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; phosphocholines, such as n-dodecylphosphocholine, (DDPC); sodium dodecyl sulfate (SDS); n-lauryl sarcosine; n-dodecyl-N,N-dimethylamine-N-oxide (LADO); n-dodecyl-β-D-maltoside (DDM); decyl maltoside (DM), n-dodecyl-N,N-dimethylamine N-oxide (LADO); n-decyl-N,N-dimethylamine-N-oxide, 1,2-diheptanoyl-sn-glycero-3-phosphocholine (DHPC); 1,2-dilauroyl-sn-glycero-3-phosphocholine (DLPC); 2-methacryloyloxyethyl phosphorylcholine (MPC); 1-oleoyl-2-hydroxy-sn-glycero-3-[phospho-RAC-(1-glycerol)] (LOPC); 1-palmitoyl-2-hydroxy-sn-glycero-3-[phospho-RAC-(1-glycerol)] (LLPG); 3-[(3-cholamidopropyl) dimethylammonio]-1-propanesulfonate (CHAPS); n-Octyl-N,N-dimethyl-3-ammonio-1-propanesulfonate; n-Decyl-N,N-dimethyl-3-ammonio-1-propanesulfonate; n-Dodecyl-N,N-dimethyl-3-ammonio-1-propanesulfonate; n-Hexadecyl-N,N-dimethyl-3-ammonio-1-propanesulfonate; Tetradecanoylamidopropyl-dimethylammonio-propanesulfonate; Hexadedecanoylamidopropyl-dimethylammonio-propanesulfonate; 4-n-Octylbenzoylamido-propyl-dimethylammonio Sulfobetaine; a Poly(maleic anhydride-alt-1-tetradecene), 3-(dimethylamino)-1-propylamine derivative; a nonyl phenoxylpolyethoxylethanol (NP40) surfactant; alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins, including lecithin, lysolecithin, phosphatidylcholine, phosphatidylethanolamine, phosphatidylglycerol, phosphatidic acid, phosphatidylserine; lysolecithins and hydrogenated lysolecithins; phospholipids and derivatives thereof; lysophospholipids and derivatives thereof, including lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof; alkylmaltosides; alkylthioglucosides; lauryl macrogolglycerides; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and combinations thereof.

Figure 78:
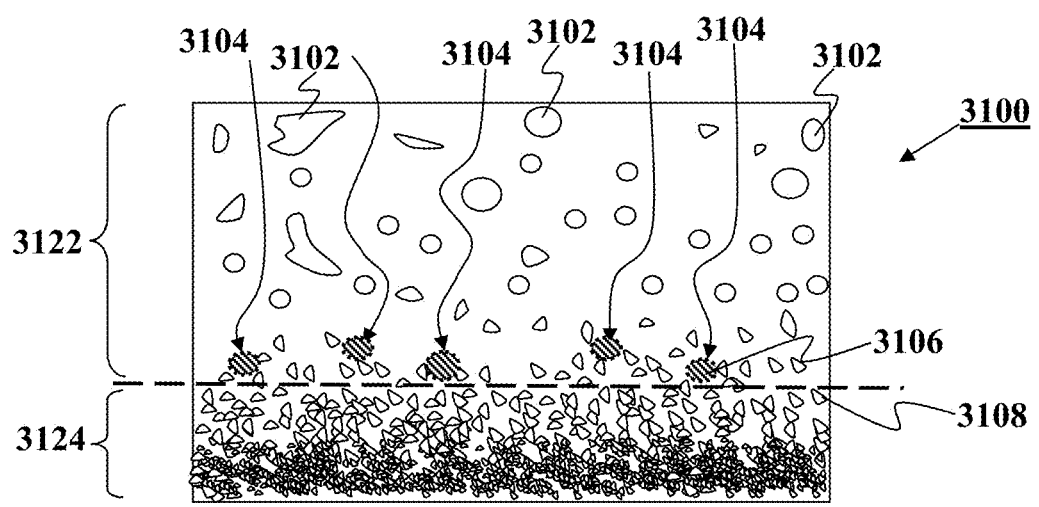
FIG. 78 shows a side, cross-sectional view of a separation material according to one embodiment described herein.

Referring now to FIG. 78, one embodiment of a filtering device such as but not limited to a bodily fluid separation material 3100 will now be described. FIG. 78 shows a side cross-sectional view of the separation material 3100, showing cross-sections of the structures 3102 of the separation material. By way of non-limiting example, the separation material 3100 may be a size-exclusion barrier such as but not limited to a porous membrane with size-exclusion properties. Other embodiments may use other types of size-exclusion barrier(s). In one embodiment described herein, the structures 3102 are fibers in the separation material with their cross-sectional views shown in FIG. 78. Optionally, the structures 3102 are mesh portions of the separation material. Optionally, the structures 3102 are pore walls or pore-defining structures of the separation material. Optionally, the structures 3102 may be a percolating network of connected fibers, elongate members, or the like. Some embodiments may combine one or more of the foregoing to form the separation material. Although the descriptions herein are written in the context of a separation material, other filter materials or structures in sheet-like or other shapes are not excluded material. FIG. 78 shows that for the present embodiment, formed components 3106 such as but not limited to red blood cells, white blood cells, platelet, or other formed components of the bodily fluid can enter the separation material 3100 in a variety of directions, including from a top-down manner, and will continue to pass through the separation material until the component reaches a size-constrained area where the spacing becomes too small for the formed component 3106 to proceed any further. In this embodiment, operating under the principle of size exclusion, the formed component 3106 will then be constrained in the separation material 3100 while liquid portions and/or those components not size excluded can continue to pass through the separation material. In one non-limiting example, arrows 3104 show movement of formed components through the separation material 3100 of FIG. 78. Other movement, such as but not limited to lateral, side-ways, and/or diagonal movement, is not excluded.

Referring still to the embodiment of FIG. 78, the dotted line 3120 shows that in this embodiment, there are at least two regions 3122 and 3124 for the separation material 3100. It should be understood that other embodiments can have even more regions. In this current embodiment, the region 3122 comprises a formed component capture region. In some specific embodiments as will be discussed in more detail below, it may be an anti-hemolytic, formed component capture region. By way non-limiting example, the region 3124 comprises a pass-through region that has structural elements spaced closely enough that formed components of the bodily fluid sample cannot completely pass through that region 3124. In at least some embodiments, the sizing and/or spacing of elements is selected such that the size-restriction technique of separation material components prevents the formed components from continuing through the separation material. This filters out the formed components from the liquid components of the bodily fluid.

In one embodiment, because region 3122 can be configured to be a formed component capture region, structures in the region 3122 will have more potential direct contact with the formed components 3106 and be in contact with them for a longer period of time, relative to structures in the second region 3124. Due at least in part to the greater direct contact physically and temporally, it may be desirable in it at least some embodiments described herein to treat the structures 3102 of the region 3122 to minimize undesirable breakdown, spoilage, or other detrimental effect that may result from the formed components being captured in the region 3122. In one non-limiting example, the structures 3102 may be coated with an anti-hemolytic coating to prevent breakdown of red blood cell when the bodily fluid being processed is blood. One embodiment of an anti-hemolytic coating may be an NTA coating. Optionally, other anti-hemolytic treatments in layer or other form may use material such as but not limited to n-Octyl-β-D-Glucopyranoside (OG), cell lipid bilayer intercalating material, phosphate ester containing at least two ester linkages comprising fatty hydrocarbon groups, tri-2-ethylhexylphosphate, di-2-ethylhexylphthalate, dioctylterephthalate, anti-hemolytic surfactant(s), a surfactant such as but not limited to polysorbate 80 mixed with any of the foregoing, and/or other anti-hemolytic material. Other anti-hemolytic material used with embodiments herein includes but is not limited to one or more of the following: anti-coagulants, proteins (such as but not limited to BSA, HSA, Heparin, Casein, etc.), surfactants (such as but not limited to Tween, Silwet, SDS, etc.), sugars (such as but not limited to sucrose, trealose, etc.), and/or the like.

In one embodiment, the region 3124 may be configured to be a liquid pass-through region positioned after the bodily fluid has passed through region 3122. Although FIG. 78 illustrates region 3124 to be next to region 3122, it should be understood that embodiments having intermediate region(s) and/or space between the regions are not excluded. By way of non-limiting example, the pass-through region 3124 may be configured not have direct contact with the formed components. Optionally, only structures 3108 defining part of the upper portion of the region 3124 may be in contact with any formed components 3106. Optionally, only structures 3108 defining part of the upper surface of the region 3124 may be in contact with any formed components 3106. In one embodiment, the region 3124 may be have a selected structure size, spacing, and/or other property that prevents formed components 3106 from passing through the region 3124 so as to enable a size restriction filtering technique for removing formed components from the bodily sample.

In at least some embodiments, because the formed components are not in direct contact with the region 3124 or are only in minimal contact with region 3124, the separation material of region 3124 may not be coated with the material used in the region 3122. Optionally, region 3124 may be selective coated with the materials used in region 3122 in a manner such as but not limited to only those portions that might still be in contact with formed components may be coated, which others portions of region 3122 are uncoated. Optionally, at least some embodiments may have some or all of region 3124 coated with a material different from that of the region 3122. Optionally, at least some embodiments may have some or all of region 3124 covered with the material of region 3122 and then adding a second layer of the second material over the material of region 3122. In one non-limiting example, this second material may be selected to prevent the first material leaching or otherwise entering the bodily fluid when the liquid passes through the region 3124. In at least some embodiments, the portions of region 3124 covered with the material of region 3122 is covered with the second material while other areas of region 3124 are substantially or at least partially uncovered by either material. By way of example and not limitation, some embodiments may use Heparin and/or other anti-coagulant as the material for the second layer. Optionally, the material for the second layer may be a material that is already in the bodily fluid sample. By way of non-limiting example, the material may be EDTA if the bodily fluid sample has already been or will be treated with EDTA. Optionally, for the second layer, some embodiments may use inert materials alone or in combination with any of the other materials listed herein.

Figure 79:
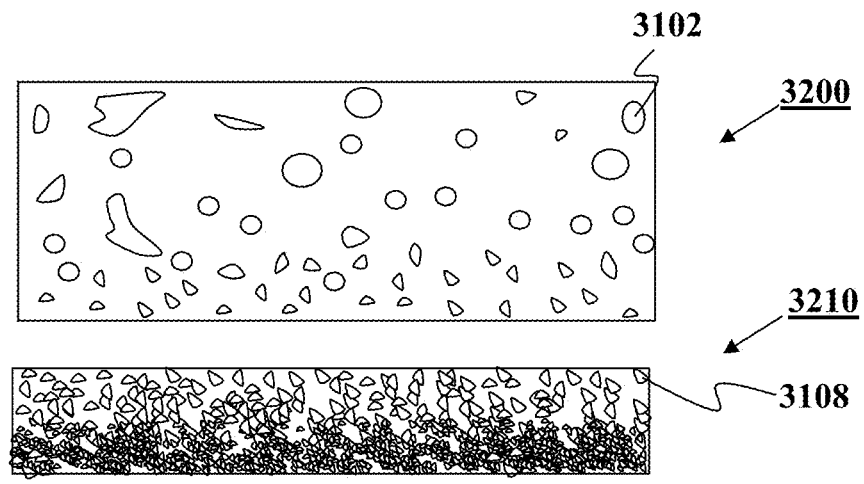
FIG. 79 shows an exploded side, cross-sectional view of separation materials according to one embodiment described herein.

Referring now to FIG. 79, a still further embodiment will now be described. This embodiment shows a first separation material 3200 and a second separation material 3210. Although only two separation materials are shown, it should be understood that other embodiments having additional separation materials above, between, and/or below the separation materials shown in FIG. 79 are not excluded. It should also be understood that one or more of the separation materials 200 and 210 can, within the separation materials themselves, each have additional regions therein for different properties.

As seen in the embodiment of FIG. 79, the separation material 200 functions as a capture region similar to the capture region 3122 of the embodiment of FIG. 78. In the current embodiment, the separation material 3210 functions as a pass-through region similar to region 3124 of the embodiment of FIG. 78.

Figure 80:
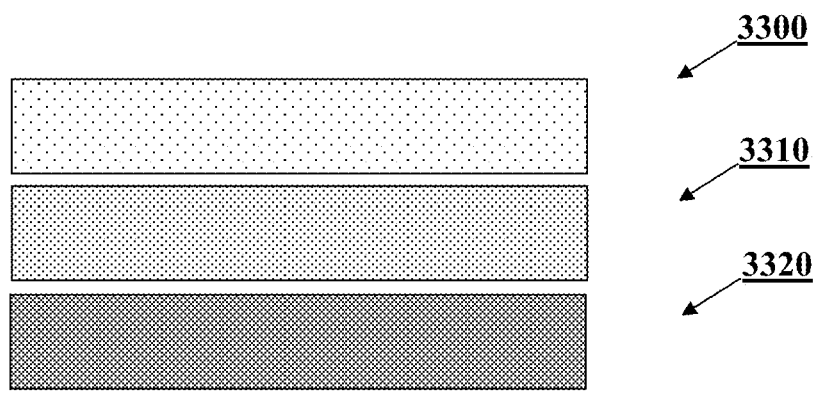
FIG. 80 is schematic of a multi-layer separation material according to one embodiment described herein.

Referring now to FIG. 80, this embodiment shows a tri-layer filter assembly with a first layer 3300, a second layer 3310, and a third layer 3320. For ease of illustration, the layers are shown to be similar in thickness, but configurations where all three are of different thicknesses, or only are of different thicknesses are not excluded. Embodiments with additional layers are also not excluded. Layers can also be formed of different materials.

It should be understood that any of the layers 3300, 3310, or 3320 can be configured as a capture region, a pass-through region, or neither. In one non-limiting example, at least the upper two layers 3300 and 3310 are capture regions. They can have similar capture capabilities, or optionally, one can be configured to be preferential capture of components while the other layer has preferential capture of components in a different size and/or shape regime. In another non-limiting example, at least the upper two layers 3300 and 3310 are captures regions, but only one of them is coated with a material to prevent degradation of the formed component(s). Optionally, both of them are coated with a material to prevent degradation of the formed component(s). Another embodiment may have two layers such as layers 3310 and 3320 that are both configured as pass-through layers. In one embodiment, neither of the layers 3310 or 3320 have structures that are coated with a material to prevent degradation of the formed component(s). Optionally, at least one of the layers 3310 or 3320 has structures that are coated with a material to prevent degradation of the formed component(s). Optionally, some embodiments have both of the layers 3310 or 3320 have structures that are coated with a material to prevent degradation of the formed component(s).

Separation Material Treatment

By way of example and not limitation, in order to be able to use separation materials for producing plasma suitable for a greater range of assays, several separation material treatment methods have been identified. Some of these techniques may involve treatment of separation materials after they are formed. Some of the techniques may involve forming the separation materials in a way that does not involve additional treatment after separation material formation. Optionally, some techniques may use both separation material formation and post-formation treatment to create a desired configuration.

Figure 81:
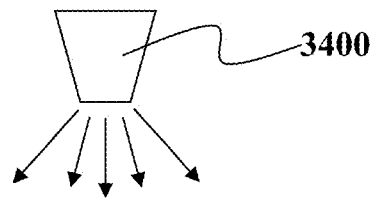
FIGS. 81 and 82 illustrate methods according to embodiments described herein.
Figure 81:
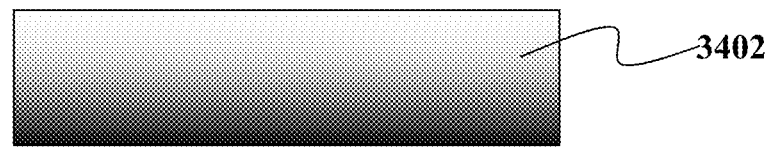

1. Separation material wash: In one embodiment described herein, by controlled washing of the coated plasma separation material by water and/or buffer solutions, most of the hemolysis-preventing agents can be removed. FIG. 81 shows that a washing mechanism, such as but not limited to a nozzle 3400 directing washing fluid (as indicated by the arrows) towards the target separation material 3402, can be used to reduce at least some of the coating off of the separation material. This can create a preferential change in the amount of coating in selected areas of the separation material. One example may show removal or at least reduction of coating on one side of the separation material. Optionally, some may direct the wash fluid to wash coating off of an interior region of the separation material. Other configurations where portions of coating are removed from other select areas are not excluded.

Figure 82:
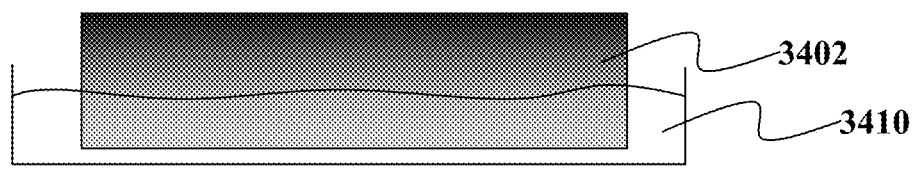

In one embodiment described herein, a carefully controlled washing is desirable so as to not completely remove the hemolysis preventing agent—which would result in hemolysis. In contrast, insufficient wash will result in sufficient amount of the hemolysis preventing agent leaching into the plasma and causing hemolysis. Thus, in one non-limiting example, a reduced amount of coating, or coating in interior portions of the separation material can be acceptable. Optionally, as seen in FIG. 82, some embodiments may also use a bath 3410 of wash fluid that preferentially removes coating material from certain areas of the separation material. Optionally, spray washing and bath soaking, or vice versa, may be combined for use on a separation material. This processing may occur sequentially or simultaneously.

2. Custom separation material coating: In another embodiment described herein, both coated and uncoated versions of the plasma separation material can be coated using a custom formulation which is compatible with assay chemistries. The coating may contain one or more of the following: proteins, surfactants, sugars, organic and inorganic salts, anti-coagulants, etc. In one non-limiting example, the coating could be applied to an initially uncoated separation material to prevent hemolysis. Optionally, an initially coated separation material may be further coated to prevent assay interfering substances from leaching into the bodily fluid from the separation material.

3. Charge Neutralization: In one embodiment described herein, separation material surface charge can be neutralized to prevent retention of small, oppositely charged ions. For example, the separation material with NTA coating has a negatively-charged surface, which can be neutralized to prevent retention of positively charged $Ca++$ ions. Optionally, if a coating has a positively-charged surface and is in turn attracting negatively charged ions in a detrimental manner, the member will be treated to neutralize the undesired charge condition.

4. Other techniques and/or materials may also be used to create a filter such as a separation material that has anti-hemolytic qualities on the capture surfaces of the filter and non-leaching qualities on other surfaces of the filter. Some embodiments may combine one or more of the foregoing techniques on a separation material. By way of non-limiting example, one embodiment may have coated and uncoated regions on a separation material along with having been treated to achieve charge neutralization before, during, and/or after coating.

EXAMPLES

Using a dynamic wash technique, asymmetric membranes were washed with high performance liquid chromatography (HPLC) grade water and then tested. In one non-limiting example, the membrane has a pore volume of 2 µL per 10 $mm^2$ of membrane. The pore loading is defined as the ratio of the total volume of blood to the pore volume. For a blood volume of 40 µL with membrane surface area of 100 $mm^2$, this corresponds to a pore loading of 2×. The wash procedure comprised pre-mounting membrane in a fixture for filtration. In this particular example, about 600 uL of water is directed through the membrane and then the water is discarded. This wash process of directing water through the membrane was repeated, which in this particular example, involved repeating the wash five (5) times. After washing, the membranes are allowed to dry. Filtration of the dynamically washed membranes were then tested.

Washing by way of soaking ("static wash") rather than the flow-through technique ("dynamic wash") can create differences in the performance of the resulting membrane. In at least some static washed membranes, anti-hemolytic is preferentially removed from the large pore region. In at some dynamic wash membranes, anti-hemolytic is preferentially removed from the small pore region. This asymmetry in coating material may be desirable when the formed blood components contact the membrane where the pores are larger while only plasma contacts the smallest pores. Hemolysis prevention happens only in the regions where RBCs can enter or be contacted (i.e. the large pore region). It is not possible to hemolyze plasma and thus coating the small pore region with anti-hemolytic does not result in noticeable performance benefit. As noted herein, the excess anti-hemolytic may have adverse impact on assay results for the assays sensitive to excess anti-hemolytic coating.

In static wash, diffusion dominates removal of anti-hemolytic. In some embodiments of the membrane, large pores may be ~50× bigger than small pores. Mass diffusion rate is proportional to cross sectional flow area. Thus diffusion rate of anti-hemolytic away from membrane on large pore side may be ~2500× greater than on small pore side. Thus, without being bound to any particular theory, total removal should be much greater on large pore side, where the RBCs contact the membrane.

In dynamic wash, shear dominates removal of anti-hemolytic. Shear increases dramatically with decreasing diameter. Without being bound to any particular theory, total removal should be greater in small pore regions, where shear is most significant.

In yet another embodiment, the coating on the membrane can be a material that provides a negative charge. Without being bound to any particular theory, a negative charge repels formed blood component that have a negative polarity, and thereby reduces mechanical trauma inflicted on such formed blood components via contact with the membrane during filtration. Some embodiments may use formulations with negatively charged substances to coat all or optionally selective areas on the membrane. One embodiment may use casein 0.5%, Tween 20 1.35%, sucrose 5%, 15 minute soak time. Optionally, one embodiment may use Li-Heparin 50 mg/mL, sucrose 5%. Optionally, one embodiment may use Li-Heparin 50 mg/mL, Tween 80 1.35%, sucrose 5%. Optionally, one embodiment may use Casein 1.0%, Tween 20 2.70%, sucrose 5%. Optionally, one embodiment may use Li-Heparin 100 mg/mL, Tween 20 2.70%, sucrose 5%.

While the teachings has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, with any of the above embodiments, it should be understood that the fluid sample may be whole blood, diluted blood, interstitial fluid, sample collected directly from the patient, sample that is on a surface, sample after some pre-treatment, or the like. Although the embodiments herein are described in the context of an anti-hemolytic coating, it should be understood that these embodiments may also be configured for use with other types of coatings, including but not limited to other coatings which may undesirably mix into the bodily fluid upon prolonged fluid exposure. Other material used with embodiments herein may include but is not limited to one or more of the following: anti-coagulants, proteins (BSA, HSA, Heparin, Casein, etc.), surfactants (Tween, Silwet, SDS, etc.), sugars (sucrose, trealose, etc.)

Although the embodiments herein are described in the context of capturing formed components such as blood cells or platelets, it should be understood that these embodiments can also be adapted for use with fluid containing other solid, semi-solid, or formed components or particles. Although the embodiments herein are described in the context of separation material, it should be understood that these embodiments can also be adapted for use other filter materials such as meshes, porous layers, or other layer like materials or structures.

In one embodiment described herein, a bodily fluid separation material is provided comprising a formed component capture region and a bodily fluid pass-through region. The pass-through region has structures with a reduced liquid leaching quality relative to than the capture region, wherein during separation material use, bodily fluid enters the capture region prior to entering the pass-through region. Optionally, a bodily fluid pass-through region has a reduced amount of liquid leaching material relative to than the capture region.

In another embodiment described herein, a bodily fluid separation material is provided comprising an anti-hemolytic and formed component capture region; and a bodily fluid pass-through region having less anti-hemolytic material than the capture region, wherein during separation material use, bodily fluid enters the capture region prior to entering the pass-through region.

In yet embodiment described herein, a bodily fluid separation material is provided comprising a first filter region of the separation material having an anti-hemolytic coating and mesh spacing sized to constrain formed blood components therein; a second filter region of the separation material having mesh spacing smaller than mesh spacing of the first filter region and configured to have an amount of anti-hemolytic coating less than that of the first region.

In a still further embodiment described herein, a bodily fluid separation material is provided comprising a percolating network of structures wherein a first region of the percolating network with an anti-hemolytic coating on structures in the region, said structures sized and spaced to allow formed blood components to enter the first region but constraining blood components therein from passing completely through the first region; and a second region of the percolating network with a reduced anti-hemolytic coating on structures sized and spaced to prevent formed blood components from entering the second region, wherein bodily fluid passes through the first region prior to reaching the second region.

It should be understood that embodiments herein may be adapted to include one or more of the following features. For example, the separation material may be an asymmetric separation material. Optionally, the anti-hemolytic material on the separation material comprises single and/or double alkyl chain N-oxides of tertiary amines (NTA). Optionally, the first region comprises a first separation material layer and the second region comprises a second separation material layer. Optionally, the separation material comprises a first separation material coupled to a second separation material. Optionally, the separation material comprises at least two separate separation materials. Optionally, there may be at least another region of the separation material between the first region and the second region. Optionally, the first region of the separation material may be in fluid communication with the second region. Optionally, the first region may be spaced apart from the second region.

In yet another embodiment described herein, a method is provided for forming a bodily fluid separation material. The method comprises coating the separation material with an anti-hemolytic coating on a first region and a second region of the separation material; reducing anti-hemolytic effect of the second region of the separation material relative to the first region, wherein when the separation material is in operation, bodily fluid passes through the first region prior to reaching the second region.

It should be understood that embodiments herein may be adapted to include one or more of the following features. For example, the method may include reducing the anti-hemolytic effect by washing off at least a portion of the anti-hemolytic coating on the second region. Optionally, washing off comprises directing solvent through the separation material. Optionally, washing off comprises soaking only a portion of the separation material in a solvent. Optionally, reducing the anti-hemolytic effect comprises adding another coating of a different material over the anti-hemolytic coating on the second region. Optionally, reducing the anti-hemolytic effect comprises treating the separation material to bring its electrical charge state to a neutral state and thus reduce the attraction of ions that increase the anti-hemolytic effect.

In yet another embodiment described herein, a method is provided for forming a bodily fluid separation material. The method comprises coating at least a first region of the separation material with an anti-hemolytic coating; not coating at least second region of the separation material with the anti-hemolytic coating. Optionally, some embodiments have a bilayer structure based on a substantially even coating of anti-hemolytic material, but instead has a region of substantially greater pore size than another region. Although the material may be asymmetric, it is a not a linear gradient, but instead has a rapid change in pore size at an inflection point when pore size is graphed in depth from top of the layer to bottom of the layer.

Additionally, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a size range of about 1 nm to about 200 nm should be interpreted to include not only the explicitly recited limits of about 1 nm and about 200 nm, but also to include individual sizes such as 2 nm, 3 nm, 4 nm, and sub-ranges such as 10 nm to 50 nm, 20 nm to 100 nm, etc. . . .

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited. The following applications are fully incorporated herein by reference for all purposes: U.S. Pat. Nos. 8,088,593; 8,380,541; U.S. patent application Ser. No. 13/769,798, filed Feb. 18, 2013; U.S. patent application Ser. No. 13/769,779, filed Feb. 18, 2013; U.S. Pat. App. Ser. No. 61/766,113 filed Feb. 18, 2013, U.S. patent application Ser. No. 13/244,947 filed Sep. 26, 2011; PCT/US2012/57155, filed Sep. 25, 2012; U.S. application Ser. No. 13/244,946, filed Sep. 26, 2011; U.S. patent application Ser. No. 13/244,949, filed Sep. 26, 2011; and U.S. Application Ser. No. 61/673,245, filed Sep. 26, 2011, U.S. Patent Application Ser. No. 61/786,351 filed Mar. 15, 2013, U.S. Patent Application Ser. No. 61/948,542 filed Mar. 5, 2014, U.S. Patent Application Ser. No. 61/952,112 filed Mar. 12, 2014, U.S. Patent Application Ser. No. 61/799,221 filed Mar. 15, 2013, U.S. Patent Application Ser. No. 61/697,797 filed Sep. 6, 2012, and U.S. Patent Application Ser. No. 61/733,886 filed Dec. 5, 2012, the disclosures of which patents and patent applications are all hereby incorporated by reference in their entireties for all purposes.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Any feature, whether preferred or not, may be combined with any other feature, whether preferred or not. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. For example, a reference to "an assay" may refer to a single assay or multiple assays. Also, as used in the description herein and throughout the claims that follow, the meaning of "in" includes "in" and "on" unless the context clearly dictates otherwise. Finally, as used in the description herein and throughout the claims that follow, the meaning of "or" includes both the conjunctive and disjunctive unless the context expressly dictates otherwise. Thus, the term "or" includes "and/or" unless the context expressly dictates otherwise.

What is claimed is:

1. A device for use with a formed component liquid sample, the device comprising:
   a housing having a first opening, a second opening, and a third opening;
   a separation material in the housing;
   a sample distributor in the housing positioned adjacent a first surface of the separation material;
   a sample collector in the housing positioned adjacent a second surface of the separation material;
   a first channel in the housing coupled to the first opening;
   a second channel in the housing fluidically coupling the first channel to the second opening; and
   a third channel in the housing fluidically coupling the first channel to the sample distributor;
   wherein the first channel and second channel define an unfiltered fluid pathway between the first opening and the second opening that does not pass through the separation material;
   wherein the first channel, the third channel, the sample distributor, the separation material, and the sample collector define a filtered fluid pathway between the first opening and the third opening.

2. The device of claim 1 wherein the sample distributor is in direct contact with at least one portion of the first surface of the separation material.

3. The device of claim 2 wherein the separation material has first filter region and a second filter region of the separation material having pore spacing smaller than pore spacing of the first filter region.

4. The device of claim 2 wherein the sample distributor comprises a plurality of distributor channels arranged in a pattern wherein at least portions of the channels are parallel to one another.

5. The device of claim 4 wherein each of the distributor channels is fluidically coupled to the third channel.

6. The device of claim 5 further comprising a plurality of vents, wherein each of the distributor channels is coupled to one of the vents.

7. The device of claim 1 wherein at least a first portion of separation material in the housing is under compression and at least a second portion of separation material in the housing is under less compression than the first portion.

8. The device of claim 1 wherein the separation material comprises an asymmetric porous membrane.

9. The device of claim 1 wherein the separation material comprises a mesh.

10. The device of claim 1 wherein at least a portion of the separation material comprises a polyethersulfone.

11. The device of claim 1 wherein at least a portion of the separation material comprises an asymmetric polyethersulfone.

12. The device of claim 1 wherein at least a portion of the separation material comprises polyarylethersulfone.

13. The device of claim 1 wherein at least a portion of the separation material comprises an asymmetric polyarylethersulfone.

14. The device of claim 1 wherein at least a portion of separation material comprises a polysulfone.

15. The device of claim 1 wherein the separation material comprises an asymmetric polysulfone.

16. The device of claim 1 wherein the separation material comprises a polysulfone membrane.

* * * * *